(12) United States Patent
Berling et al.

(10) Patent No.: US 12,290,542 B2
(45) Date of Patent: May 6, 2025

(54) COMPOSITIONS COMPRISING CANNABIS AND MUSHROOM EXTRACTS, AND USES THEREOF

(71) Applicant: Cookies Creative Consulting & Promotions, Inc., Downey, CA (US)

(72) Inventors: Parker Berling, San Francisco, CA (US); Tony M. Verzura, San Francisco, CA (US); Kevin Hall, San Francisco, CA (US)

(73) Assignee: Cookies Creative Consulting & Promotions, Inc., Downey, CA (US)

( * ) Notice: Subject to any disclaimer, the term of this patent is extended or adjusted under 35 U.S.C. 154(b) by 0 days.

(21) Appl. No.: 18/597,236

(22) Filed: Mar. 6, 2024

(65) Prior Publication Data

US 2024/0252569 A1    Aug. 1, 2024

Related U.S. Application Data

(63) Continuation of application No. 18/343,563, filed on Jun. 28, 2023, now Pat. No. 11,951,142, which is a continuation of application No. PCT/US2021/065708, filed on Dec. 30, 2021.

(60) Provisional application No. 63/132,878, filed on Dec. 31, 2020.

(51) Int. Cl.
| | |
|---|---|
| *A61K 36/07* | (2006.01) |
| *A61K 31/00* | (2006.01) |
| *A61K 31/015* | (2006.01) |
| *A61K 31/56* | (2006.01) |
| *A61K 36/062* | (2006.01) |

(52) U.S. Cl.
CPC ............ *A61K 36/07* (2013.01); *A61K 31/015* (2013.01); *A61K 31/56* (2013.01); *A61K 31/658* (2023.05); *A61K 36/062* (2013.01)

(58) Field of Classification Search
None
See application file for complete search history.

(56) References Cited

U.S. PATENT DOCUMENTS

| | | | |
|---|---|---|---|
| 3,033,690 | A | 5/1962 | Tarvin et al. |
| 7,258,862 | B2 | 8/2007 | Mahajna et al. |
| 7,700,368 | B2 | 4/2010 | Flockhart et al. |
| 8,481,085 | B2 | 7/2013 | Musty et al. |
| 9,359,625 | B2 | 6/2016 | Winnicki et al. |
| 9,744,200 | B1 | 8/2017 | Tucker et al. |
| 10,159,908 | B2 | 12/2018 | Thomas |
| 10,555,914 | B1 | 2/2020 | Metcalf |
| 2008/0031977 | A1 | 2/2008 | Musty et al. |
| 2016/0000754 | A1* | 1/2016 | Stamets .............. A61K 31/05 549/287 |
| 2018/0078874 | A1 | 3/2018 | Thomas |
| 2018/0193403 | A1 | 7/2018 | George et al. |
| 2018/0200224 | A1 | 7/2018 | Stamets |
| 2019/0151771 | A1 | 5/2019 | Thomas |
| 2020/0048214 | A1 | 2/2020 | Thomas et al. |
| 2020/0048215 | A1 | 2/2020 | Thomas et al. |
| 2020/0080021 | A1 | 3/2020 | Thomas |
| 2020/0246404 | A1 | 8/2020 | Yucel et al. |
| 2020/0330378 | A1 | 10/2020 | Friedman |
| 2020/0352206 | A1 | 11/2020 | Wagner-Salvini |
| 2023/0338447 | A1 | 10/2023 | Berling et al. |

FOREIGN PATENT DOCUMENTS

| | | |
|---|---|---|
| WO | WO-2015065544 A1 | 5/2015 |
| WO | WO-2016200438 A1 | 12/2016 |
| WO | WO-2020136593 A1 | 7/2020 |
| WO | WO-2020188577 A1 | 9/2020 |

OTHER PUBLICATIONS

Bartlett et al., "Understanding the Oral Mucosal Absorption and Resulting Clinical Pharmacokinetics of Asenapine," AAPS PharmSciTech vol. 13(4), pp. 1110-1115 (2012).
Caglarirmak et al., "The nutrients of exotic mushrooms (*Lentinula edodes* and *Pleurotus* species) and an estimated approach to the volatile compounds," Food Chemistry 105(3): 1188-1194 (Dec. 2007).
Eubanks et al.,"A Molecular Link Between the Active Component of Marijuana and Alzheimer's Disease Pathology," Molecular Pharmaceutics 3(6): 773-777 (2006).
Gery et al., "Chaga (*Inonotus obliquus*), a Future Potential Medicinal Fungus in Oncology? A Chemical Study and a Comparison of the Cytotoxicity Against Human Lung Adenocarcinoma Cells (A549) and Human Bronchial Epithelial Cells (BEAS-2B)," Integr. Cancer Ther. 17(3): 832-843 (Sep. 2018).
Herring et al., "Cannabinol-mediated inhibition of nuclear factor-kappaB, cAMP response element-binding protein, and interleukin-2 secretion by activated thymocytes," Journal of Pharmacology and Experimental Therapeutics December 291(3) 1156-1163 (1999).
Hoaken, "Drugs of abuse and the elicitation of human aggressive behavior," Addictive Behaviors 28: 1533-1554 (2003).
International Search Report and Written Opinion for International Application No. PCT/US2021/065708 dated Mar. 17, 2022, 21 pages.
Li et al., "Neurohealth Properties of Hericium erinaceus Mycelia Enriched with Erinacines," Behavioral Neurology Article ID 5802634, 10 pages (2018).
Marks et al., "Identification of candidate genes affecting Δ9-tetrahydrocannabinol biosynthesis in Cannabis sativa," Journal of Experimental Botany 60 (13): 3715-3726 (Jul. 2009).
McAllister et al., "Cannabidiol as a novel inhibitor of Id-1 gene expression in aggressive breast cancer cells," Mol. Cancer Ther. 6 (11): 2921-7 (Nov. 2007).

(Continued)

*Primary Examiner* — Michael V Meller
(74) *Attorney, Agent, or Firm* — Cooley LLP

(57) ABSTRACT

The present disclosure provides for compositions combining Cannabinoid Fractions and Mushroom Extract Fractions for recreational and medicinal uses. The disclosed compositions are useful for treating symptoms of anxiety, stress, pain, and promoting sleep. The pharmaceutical compositions comprise particular cannabinoid ratios and terpene profiles.

19 Claims, 37 Drawing Sheets

(56) References Cited

OTHER PUBLICATIONS

Mechoulam et al., "Cannabidiol—Recent Advances," Chemistry & Biodiversity 4(8):1678-1692 (2007).

Nicholson et al., "Effect of Delta-9-tetrahydrocannabinol and cannabidiol on nocturnal sleep and early-morning behavior in young adults," J Clin Psychopharmacol. Jun. 2004;24(3):305-13 (Jun. 2004).

Pickens, "Sedative activity of cannabis in relation to its delta'-trans-tetrahydrocannabinol and cannabidiol content," Br J Pharmacol. Apr. 1981;72(4):649-56 (1981).

Pollastro et al., "Iodine-Promoted Aromatization of p-Menthane-Type Phytocannabinoids," J Nat Prod;81(3):630-633 (Mar. 23, 2018). Epub Dec. 14, 2017.

Qu et al., "Anticancer effect of triterpenes from Ganoderma lucidum in human prostate cancer cells," Oncol Lett 14(6): 7467-7472 (Dec. 2017). Published online Oct. 9, 2017.

Russo et al., "Taming THC: potential cannabis synergy and phytocannabinoid-terpenoid entourage effects," Br J Pharmacol 163(7):1344-64 (Aug. 2011).

Salehi et al., "Therapeutic Potential of α- and β-Pinene: A Miracle Gift of Nature," Biomolecules 9(11):738 (2019).

Smiderle et al., "Anti-Inflammatory Properties of the Medicinal Mushroom Cordyceps militaris Might Be Related to Its Linear (1R3)-b-D-Glucan," PLoS One 9(10): e110266, pp. 1-11 (2014).

Taura et al., "Purification and Characterization of Cannabidiolic-acid Synthase from *Cannabis sativa* L.," The Journal of Biological Chemistry, vol. 271, No. 21, p. 17411-17416 (Issue of Jul. 19, 1996).

Tuli et al., "Pharmacological and therapeutic potential of Cordyceps with special reference to Cordycepin," 3 Biotech 4(1):1-12 (2014).

Valdeolivas et al., "Neuroprotective properties of cannabigerol in Huntington's disease: studies in R6/2 mice and 3-nitropropionate-lesioned mice," Neurotherapeutics 12(1):185-99 (Jan. 2015).

Extended European Search Report for European Application No. 21916507.3 mailed Nov. 28, 2024, 7 pages.

\* cited by examiner

Sample 1 Trial Results- Mental Focus

Sample 1 Trial Results- Function Normally

Sample 1 Trial Results- Mood Enhancement

Sample 3 Trial Results- Energy Level

Sample 3 Trial Results- Function Normally

Sample 3 Trial Results- Mood Enhancement

Sample 2 Trial Results- Falling Asleep

Sample 2 Trial Results- Sleep Length

Sample 2 Trial Results- Morning Effects

Sample 2 Trial Results– Calm

Sample 2 Trial Results- Ability to Relax

Sample 2 Trial Results- Physical Comfort

Sample 2 Trial Results- Emotional Comfort

Sample 4 Trial Results- Falling Asleep

Sample 4 Trial Results- Sleep Quality

Sample 4 Trial Results- Calm

Sample 4 Trial Results- Ability to Relax

COMPOSITIONS COMPRISING CANNABIS AND MUSHROOM EXTRACTS, AND USES THEREOF

CROSS-REFERENCE TO RELATED APPLICATIONS

This application is a continuation of U.S. application Ser. No. 18/343,563, which was filed on Jun. 28, 2023, now U.S. Pat. No. 11,951,142, which was a continuation of International Application No. PCT/US2021/065708, filed Dec. 30, 2021, which claims the benefit of priority to U.S. Provisional Application No. 63/132,878, filed on Dec. 31, 2020, each of which is hereby incorporated by reference in its entirety.

FIELD

The present disclosure generally relates to compositions and formulations thereof comprising unique combinations of cannabinoids, terpenes, and mushroom extracts and methods of making the said compositions.

BACKGROUND

Medical marijuana has over 80 active constituents with potential therapeutic benefits.

Mushrooms also contain several active ingredients associated with many health benefits and potential therapeutic properties.

The health benefits, which derive from the presence of compositions containing both medical marijuana and mushrooms have not yet been realized. As such there remains a need in the art for the production of such compositions.

SUMMARY

There is an unmet need for improved compositions for recreational and medical of cannabinoid products. The present disclosure provides compositions comprising mushroom extracts, cannabinoids, and terpenes with enhanced recreational and medicinal properties.

The compositions described herein are designed to increase bioavailability and leverage the synergies between cannabinoids (Cannabinoid Fraction), terpenes (Terpene Fraction), and mushroom extracts (Mushroom Extract Fraction) (See Russo et al. Br J Pharmacol. 2011 August; 163(7): 1344-1364.). Individual compounds within each of the aforementioned fractions exhibit nutritional, health, therapeutic, and/or medicinal properties; the combination of these formulations provides enhanced properties for recreational and medical use. Potential health, therapeutic, and/or medicinal benefits of the compositions described herein include alleviation of one or more symptoms of autoimmune disorders, asthma, chronic obstructive pulmonary disease (COPD, general lung health, anti-inflammatory, boost immunity, lower stress hormones, digestive disorders, IBS, Crohn's Disease, Parkinson Disease, Alzheimer's, insomnia, sleep aide, neuroprotective, PTSD, anxiety, MS, anti-spasmatic, antioxidants, reduce free radicals, Libido, Type-2 Diabetes, heart health, and cancer.

In some embodiments, the present disclosure provides a composition comprising: a) a Cannabinoid Fraction; b) a Mushroom Extract Fraction; and c) a Terpene Fraction.

In some embodiments, the present disclosure provides a composition comprising: a) a Cannabinoid Fraction; b) a Mushroom Extract Fraction; and c) a Terpene Fraction wherein the Cannabinoid Fraction comprises two cannabinoids selected from the group consisting of: cannabidiol (CBD), cannabigerol (CBG), cannabinol (CBN), and tetrahydrocannabinol (THC).

In some embodiments, the present disclosure provides a composition comprising: a) a Cannabinoid Fraction; b) a Mushroom Extract Fraction; and c) a Terpene Fraction, wherein the Mushroom Extract Fraction comprises at least two mushroom extracts selected from the group consisting of; *Hericium ernaceus, Cordyceps militaris, Trametes versicolor, Ganoderma lingzhi, Grifola frondosa, Lentinula edodes*, and *Inonotus obliquus*.

In some embodiments, the present disclosure provides a composition comprising: a) a Cannabinoid Fraction; b) a Mushroom Extract Fraction; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, the present disclosure provides a composition comprising: a) a Cannabinoid Fraction; b) a Mushroom Extract Fraction; and c) a Terpene Fraction, wherein the Terpene Fraction comprises alpha pinene, limonene, beta-pinene, alpha phellandrene, terpinolene, nerolidol, and nerol.

In some embodiments, the present disclosure provides a composition comprising: a) a Cannabinoid Fraction; b) a Mushroom Extract Fraction; and c) a Terpene Fraction, and a triterpene selected from the group consisting of ergosterol peroxide; cerevisterol; $3\beta.5\alpha,9\alpha$,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the present disclosure provides a composition comprising: a) a Cannabinoid Fraction; b) a Mushroom Extract Fraction; and c) a Terpene Fraction, said composition comprising Beta-D-glucans.

In some embodiments, the present disclosure provides a composition comprising: a) a Cannabinoid Fraction; b) a Mushroom Extract Fraction; and c) a Terpene Fraction; said composition comprising valerian root.

In some embodiments, the present disclosure provides a composition comprising: a) a Cannabinoid Fraction; b) a Mushroom Extract Fraction; and c) a Terpene Fraction; said composition comprising starch.

In some embodiments, the present disclosure provides a composition comprising: a) a Cannabinoid Fraction; b) a Mushroom Extract Fraction; and c) a Terpene Fraction; said composition comprising hypromellose, microcrystalline cellulose, inositol, and MCT oil.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction wherein the Terpene Fraction comprises alpha pinene, limonene, beta-pinene, alpha phellandrene, terpinolene, nerolidol, and nerol.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Cannabinoid Fraction comprises a CBD:CBG ratio of between 2:1 and 1:2 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Cannabinoid Fraction comprises a CBD:CBG ratio of about 3:4 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Cannabinoid Fraction comprises between 30-50% CBD and 40-70% CBG by weight of the Cannabinoid Fraction.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Mushroom Extract Fraction comprises a *Hericium ernaceus*:*Cordyceps militaris* ratio between 2:1 and 1:2 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Mushroom Extract Fraction comprises a *Hericium ernaceus*:*Cordyceps militaris* ratio of about 1:1 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Mushroom Extract Fraction comprises between 40-60% *Hericium ernaceus* and 40-60% *Cordyceps militaris* by weight of the Mushroom Extract Fraction.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising a Cannabinoid Fraction to Mushroom Extract Fraction ratio between 1:8 to 1:10 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction; said composition comprising a Cannabinoid Fraction to Mushroom Extract Fraction ratio of about 7:60 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction; said composition comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemicer-amide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction; said composition comprising Beta-D-glucans.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction; said composition comprising valerian root.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction said composition comprising starch.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction; said composition comprising hypromellose, microcrystalline cellulose, inositol, and MCT oil.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction.

In some embodiments, provided herein is a composition comprising: a) a Cannabinoid Fraction comprising i) 15 mg cannabidiol (CBD); ii) 20 mg cannabigerol (CBG); and b) a Mushroom Extract Fraction comprising i) 150 mg *Hericium ernaceus*; ii) 150 mg *Cordyceps militaris*; and c) a Terpene Fraction comprising alpha pinene, limonene, beta-pinene, alpha phellandrene, terpinolene, nerolidol, and nerol.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Terpene Fraction comprises alpha pinene, limonene, beta-pinene, alpha phellandrene, terpinolene, nerolidol, and nerol.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises a CBN:CBD ratio between 2:1 and 1:2 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises a CBN:CBD ratio of about 2:3 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises between 30-40% CBN and 60-70% CBD by weight of the Cannabinoid Fraction.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Mushroom Extract Fraction comprises about equal parts of *Trametes versicolor, Ganoderma lingzhi, Grifola frondosa, Lentinula edodes,* and *Inonotus obliquus* by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Mushroom Extract Fraction comprises between 10-30% *Trametes versicolor,* 10-30% *Ganoderma lingzhi,* 10-30% *Grifola frondosa,* 10-30% *Lentinula edodes,* and 10-30% *Inonotus obliquus* by weight of the Mushroom Extract Fraction.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a Cannabinoid Fraction to Mushroom Extract Fraction ratio between 1:8 to 1:10 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a Cannabinoid Fraction to Mushroom Extract Fraction ratio of about 7:60 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemicer-amide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising Beta-D-glucans.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising valerian root.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising starch.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising hypromellose, microcrystalline cellulose, inositol, and MCT oil.

In some embodiments, provided herein is a composition comprising: a) a Cannabinoid Fraction comprising i) 10 mg cannabinol (CBN); ii) 15 mg cannabidiol (CBD); and b) a Mushroom Extract Fraction comprising i) 60 mg *Trametes versicolor*, ii) 60 mg *Ganoderma lingzhi*, iii) 60 mg *Grifola frondosa*, iv) 60 mg *Lentinula edodes*, v) 60 mg *Inonotus obliquus*; and c) a Terpene Fraction comprising alpha pinene, limonene, beta-pinene, alpha phellandrene, terpinolene, nerolidol, and nerol.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, wherein the Terpene Fraction comprises alpha pinene, limonene, beta-pinene, alpha phellandrene, terpinolene, nerolidol, and nerol.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, wherein the Mushroom Extract Fraction comprises a *Hericium ernaceus:Cordyceps militaris* ratio between 2:1 and 1:2 by weight.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, wherein the Mushroom Extract Fraction comprises a *Hericium ernaceus:Cordyceps militaris* ratio of about 1:1 by weight.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, wherein the Mushroom Extract Fraction comprises between 40-60% *Hericium ernaceus* and 40-60% *Cordyceps militaris* by weight of the Mushroom Extract Fraction.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising a Cannabinoid Fraction to Mushroom Extract Fraction ratio between 1:8 to 1:11 by weight.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising a Cannabinoid Fraction to Mushroom Extract Fraction ratio of about 1:10 by weight.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising Beta-D-glucans.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising valerian root.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising starch.

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction, said composition comprising hypromellose, microcrystalline cellulose, inositol, and MCT oil.

In some embodiments, provided herein is a composition comprising a) a Cannabinoid Fraction comprising 10 mg tetrahydrocannabinol (THC); b) a Mushroom Extract Fraction comprising i) 50 mg *Hericium ernaceus*; ii) 50 mg *Cordyceps militaris*; and c) a Terpene Fraction comprising alpha pinene, limonene, beta-pinene, alpha phellandrene, terpinolene, nerolidol, and nerol.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Terpene Fraction comprises alpha pinene, limonene, beta-pinene, alpha phellandrene, terpinolene, nerolidol, nerol, myrcene, and beta caryophyllene.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises a THC:CBN ratio between 6:1 and 2:1 by weight.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises a THC:CBN ratio of about 4:1 by weight.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises between 70-90% THC and 10-30% CBN by weight of the Cannabinoid Fraction.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Mushroom Extract Fraction comprises about equal parts of *Trametes versicolor, Ganoderma lingzhi, Grifola frondosa, Lentinula edodes*, and *Inonotus obliquus* by weight.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Mushroom Extract Fraction comprises between 10-30% *Trametes versicolor*, 10-30% *Ganoderma lingzhi*, 10-30% *Grifola frondosa*, 10-30% *Lentinula edodes*, and 10-30% *Inonotus obliquus* by weight of the Mushroom Extract Fraction.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a Cannabinoid Fraction to Mushroom Extract Fraction ratio between 1:8 to 1:10 by weight.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a Cannabinoid Fraction to Mushroom Extract Fraction ratio of about 1:8 by weight.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h] beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinuila edodes*, v) *Inonotus obliquus*; and c) a Terpene Fraction, said composition comprising Beta-D-glucans.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising valerian root.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, ii) *Grifola frondosa*, iv) *Lentinula edodes*, v) *Inonotus obliquus*; and c) a Terpene Fraction, said composition comprising starch.

In some embodiments, provided herein is a composition comprising a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising hypromellose, microcrystalline cellulose, inositol, and MCT oil.

In some embodiments, provided herein is a composition comprising a) a Cannabinoid Fraction comprising i) 10 mg tetrahydrocannabinol (THC); ii) 2.5 mg cannabinol (CBN); and b) a Mushroom Extract Fraction comprising i) 20 mg *Trametes versicolor*, ii) 20 mg *Ganoderma lingzhi*, iii) 20 mg *Grifola frondosa*, iv) 20 mg *Lentinula edodes*, v) 20 mg *Inonotus obliquus*; and c) a Terpene Fraction comprising alpha pinene, limonene, beta-pinene, alpha phellandrene, terpinolene, nerolidol, and nerol.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Terpene Fraction comprises alpha pinene, limonene, beta-pinene, alpha phellandrene, terpinolene, nerolidol, and nerol.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Cannabinoid Fraction comprises a CBD:CBG ratio between 2:1 and 1:2 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Cannabinoid Fraction comprises a CBD:CBG ratio of about 3:4 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Cannabinoid Fraction comprises between 30-50% CBD and 40-70% CBG by weight of the Cannabinoid Fraction.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Mushroom Extract Fraction comprises a *Hericium ernaceus:Cordyceps militaris* ratio between 2:1 and 1:2 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Mushroom Extract Fraction comprises a *Hericium ernaceus:Cordyceps militaris* ratio of about 1:1 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, wherein the Mushroom Extract Fraction comprises between 40-60% *Hericium ernaceus* and 40-60% *Cordyceps militaris* by weight of the Mushroom Extract Fraction.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising a Cannabinoid Fraction to Mushroom Extract Fraction ratio between 3:1 to 1:1 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising a Cannabinoid Fraction to Mushroom Extract Fraction ratio of about 21:10 by weight.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising a triterpene selected from the group consisting of ergosterol peroxide; cerevisterol; 3β,5α,9α,-trihydroxy-ergosta-7,22-dien-6-one; inoterpene A; astradoric acid C; betulin; oleanolic acid; ursolic acid; hemicer-amide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising Beta-D-glucans.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising valerian root.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising starch.

In some embodiments, provided herein is a composition comprising a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction, said composition comprising hypromellose, microcrystalline cellulose, inositol, and MCT oil.

In some embodiments, provided herein is a composition comprising: a) a Cannabinoid Fraction comprising i) 450 mg cannabidiol (CBD); ii) 600 mg cannabigerol (CBG); and b) a Mushroom Extract Fraction comprising i) 250 mg *Hericium ernaceus*; ii) 250 mg *Cordyceps militaris*; and c) a Terpene Fraction comprising alpha pinene, limonene, beta-pinene, alpha phellandrene, terpinolene, nerolidol, and nerol.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Terpene Fraction comprises alpha pinene, limonene, beta-pinene, alpha phellandrene, terpinolene, nerolidol, and nerol.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises a CBN:CBD ratio between 2:1 and 1:2 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises a CBN:CBD ratio of about 2:3 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Cannabinoid Fraction comprises between 30-40% CBN and 60-70% CBD by weight of the Cannabinoid Fraction.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Mushroom Extract Fraction comprises about equal parts of *Trametes versicolor, Ganoderma lingzhi, Grifola frondosa, Lentinula edodes*, and *Inonotus obliquus* by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, wherein the Mushroom Extract Fraction comprises between 10-30% *Trametes versicolor,* 10-30% *Ganoderma lingzhi,* 10-30% *Grifola frondosa,* 10-30% *Lentinula edodes,* and 10-30% *Inonotus obliquus* by weight of the Mushroom Extract Fraction.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a Cannabinoid Fraction to Mushroom Extract Fraction ratio between 2:1 to 1:2 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a Cannabinoid Fraction to Mushroom Extract Fraction ratio of about 3:2 by weight.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising Beta-D-glucans.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising valerian root.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising starch.

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction, said composition comprising hypromellose, microcrystalline cellulose, inositol, and MCT oil.

In some embodiments, provided herein is a composition comprising: a) a Cannabinoid Fraction comprising i) 300 mg cannabinol (CBN); ii) 450 mg cannabidiol (CBD); and b) a Mushroom Extract Fraction comprising i) 100 mg *Trametes versicolor*, ii) 100 mg *Ganoderma lingzhi*, iii) 100 mg *Grifola frondosa*, iv) 100 mg *Lentinula edodes*, v) 100 mg *Inonotus obliquus*; and c) a Terpene Fraction comprising alpha pinene, limonene, beta-pinene, alpha phellandrene, terpinolene, nerolidol, and nerol.

DETAILED DESCRIPTION

I. Definitions

Figure 1:
FIG. 1 shows a picture of a *Hericium erinaceus* mushroom.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). For example, "about 100 mg" is understood to comprise 90-110 mg. When used in conjunction with a range or series of values, the term "about" applies to the endpoints of the range or each of the values enumerated in the series, unless otherwise indicated. As used in this application, the terms "about" and "approximately" are used as equivalents.

Herein, the terms "comprise", or variations such as "comprises" or "comprising", will be understood to imply the inclusion of a stated element or integer or group of elements or integers but not the exclusion of any other element or integer or group of elements or integers.

The terms "administer," "administering" or "administration" as used herein refer to either directly administering a composition described herein to a subject.

The term "carrier" as used herein encompasses materials involved in carrying or transporting a pharmaceutical agent from one organ, or portion of the body, to another organ or portion of the body.

As used herein, the term "cultivar" means a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

As used herein, the term "chemovar" means plants distinguished by the chemical compounds produced, rather than the morphological characteristics of the plant.

The term "effective amount" refers to the minimum amount of an agent or composition required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used within the context of this application, the term "purified" means extracted, isolated, and/or separated from other compounds, formulations, compositions, matter, and/or mass.

The term "reference value" or "control value" refers to a value or measurement obtained from an experimental control group (e.g., vehicle treated or untreated control values) or to a baseline value obtained from a sample or subject before treatment that is then compared to a value obtained from the sample or subject after treatment.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

The term "substantially pure" or "substantially pure active ingredient(s)" means preparations of any one of the active ingredients having a chromatographic purity (of the active ingredient) of greater than about 95% prior to its addition to the pharmaceutical composition.

As used herein, the term "winterizing" or "winterization" refers to the process by which plant lipids and waxes are removed from a *cannabis* extract. Persons have skill in the art will immediately recognize how to winterize an extract. Briefly, winterization is the dissolving the *cannabis* extract into a polar solvent (most commonly ethanol) at sub-zero temperatures. Doing so separates the waxes and lipids from the oil, forcing them to collect at the top of the mixture for easy filtration/collection. Typically, winterization is conducted by mixing ethanol and hash oil into a container and placing it into a sub-zero freezer.

II. Cannabis

*Cannabis* is a genus of flowering plants that includes three different species, *Cannabis sativa*, *Cannabis* indica and *Cannabis ruderalis*. There are 483 identifiable chemical constituents known to exist in the *cannabis* plant (Rudolf Brenneisen (2007) in Marijuana and the Cannabinoids, ElSohly, ed.; incorporated herein by reference), including at least 85 different cannabinoids and over 120 terpenes (E1-Alfy, Abir T, et al. (2010) Pharmacology Biochemistry and Behavior 95 (4): 434-42; incorporated herein by reference). The two most well-known cannabinoids produced by *Cannabis* plants are tetrahydrocannabinol (THC) and cannabidiol (CBD).

IIA. Cannabinoids

Cannabinoids are a unique family of terpeno-phenolic compounds produced by *Cannabis* plants. Typical cannabinoids isolated from *Cannabis* plants include, but are not limited to, Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinolic Acid (THCA), delta 9 Tetrahydrocannabinol (THC), Tetrahydrocannabinolic acid C4 (THCA-C4), Tetrahydrocannbinol C4(THC-C4), Tetrahydrocannabivarin (THCV), Tetrahydrocannabivarinic acid (THCVA), Tetrahydrocannabiorcolic acid (THCA-C4), Tetrahydrocannabiorcol (THC-C1), Δ7-cis-iso-tetrahydrocannabivarin, Δ8-tetrahydrocannabinolic acid (Δ8-THCA), Cannabivarinodiolic (CBNDVA), Cannabivarinodiol (CBNDV), Δ8-tetrahydrocannabinol (Δ8-THC), Δ9-tetrahydrocannabinol (Δ9-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodiolic Acid (CBNDA), Cannabinodivarin (CBDV), Cannabitriol (CBT), 10-Ethoxy-9-hydroxy-Δ6a-tetrahydrocannabinol, 8,9-Dihydroxy-Δ6a(10a)-tetrahydrocannabinol (8,9-Di-OH-CBT-C5), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, and Dodeca-2E,4E-dienoic acid isobutylamide. See Holley et al. (1975) J. Pharm. Sci. 64:892-894 and De Zeeuw et al. (9172) Science 175:778-779, each of which is herein incorporated by reference in its entirety for all purposes.

Most cannabinoids exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). Cannabinoids in their acid forms (those ending in "-A") can be converted to their non-acidic forms through a process called decarboxylation. While some decarboxylation (e.g., neutralization) of cannabinoids does occur in the plant, production of the neutral forms increase significantly post-harvest. (Sanchez and Verpoorte (2008) Plant Cell Physiol. December: 49(12)). Full decarboxylation of phytocannabinoids can be catalyzed by post-cultivation heating *cannabis* plant material or extracted cannabinoids (e.g., by combustion, vaporization, or baking in an oven).

In order to find the total amount of cannabinoids in a sample (e.g., total amount of active non-acidic cannabinoid), the total measured content of acid cannabinoid variants forms should be adjusted to account for the loss of the carboxyl group. In some embodiments, this adjustment can be made by multiplying the molar content of the acidic cannabinoid forms by the molecular weight of the corresponding decarboxylated cannabinoid. Other shorthand conversions are also available for quickly converting acidic cannabinoid content to active cannabinoid content.

For example, in some embodiments, THCA can be converted to active THC using the formula: THCA×0.877=THC. When using this approach, the maximum THC for the sample is: THCmax=(THCA×0.877)+THC. This method has been validated according to the principles of the International Conference on Harmonization. Similarly, CBDA can be converted to active CBD and the yield is determined using the yield formula: CBDA×0.877=CBD. Also, the maximum amount of CBD yielded, i.e. max CBD for the sample is: CBDmax=(CBDA×0.877)+CBD. Additionally, CBGA can be converted to active CBG by multiplying CBGA by 0.878 (CBGmax=(CBGA×0.878)+CBG).

The biosynthetic pathway of cannabinoids has been studied in great detail. According to the current model, phenolic precursors such as geranyl pyrophosphate (GPP) and polyketide, olivetolic acid (OA) are condensed by geranyl pyrophosphate olivetolate geranyl transferase (GOT) to form cannabigerolic acid (CBGA). Alternatively, GPP and divarinic acid can be condensed by GOT to form cannabigerovarinic acid (CBGVA). CBGA or CBGVA are considered to be the "primary cannabinoids" from which others can be produced.

CBGA/CBGVA is quickly transformed in plants into, for example: (1) CBCA/CBCVA by CBCA synthase; (2) THCA/THCVA by THCA synthase; or (3) CBDA/CBDVA by CBDA synthase. The genes coding for THCA synthase and CBDA synthase are found on the same B locus. Thus *cannabis* plants can be categorized into THC-CBD chemotypes based on the state of the B locus BT/BT (THC producing, chemotype I), BD/BD (CBD producing, chemotype III), and BT/BD (producing both THC and CBD, chemotype II). Additional information on the genetic regulation of cannabinoids can be found in de Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112). The BT and BD alleles are known, and can be easily detected using methods known to those skilled in the art, including Northerns, PCR, or sequencing. A representative sequence of THCA synthase is available at GenBank ID AB057805.1. A representative sequence of the CBDA synthase is available at GenBank ID AB292682.1.

Brief descriptions and chemical structures for several of the major cannabinoids are provided below.

Tetrahydrocannabinol (THC)

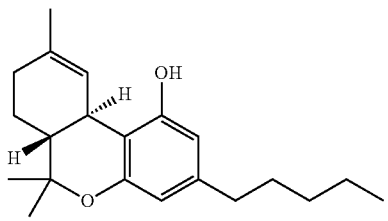 [SMILES: CCCCCc1cc(O)c2c(c1)OC(C)(C)[C@@H]1CCC(C)=C[C@@H]21]

Known as delta-9-tetrahydrocannabinol (Δ9-THC), THC is the principal psychoactive constituent (or cannabinoid) of the *cannabis* plant. The initially synthesized and accumulated form in plant is THC acid (THCA). THC has mild to moderate analgesic effects, and *cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003) Addictive Behaviors 28: 1533-1554).

The pharmacological actions of THC result from its partial agonist activity at the cannabinoid receptor CB1, located mainly in the central nervous system, and the CB2 receptor, mainly expressed in cells of the immune system (Pertwee, (2006) International Journal of Obesity 30: S13-S18.) It is also suggested that THC has an anticholinesterase action, which may implicate it as a potential treatment for Alzheimer's and Myasthenia gravis (Eubanks et al., (2006) Molecular Pharmaceutics 3 (6): 773-7).

In the *cannabis* plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC.

Non-limiting examples of THC variants include Δ9-THC-C5, Δ9-THC-C4, Δ9-THCV-C3, Δ9-THCO-C1, Δ9-THCA-C5 A, Δ9-THCA-C5 B, Δ9-THCA-C4 A, Δ9-THCA-C4 B, Δ9-THCVA-C3 A, Δ9-THCOA-C1 A, Δ9-THCOA-C1 B, Δ8-THC-C5, Δ8-THCA-C5 A, (-)-cis-Δ9-THC-C5.

Cannabidiol (CBD)

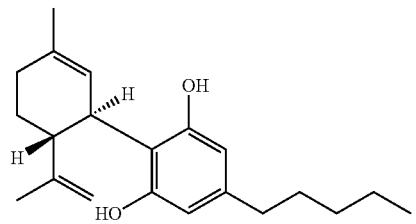 [SMILES: C=C(C)[C@@H]1CCC(C)=C[C@H]1c1c(O)cc(CCCCC)cc1O]

CBD is a cannabinoid found in *cannabis* shown to display sedative effects in animal tests (Pickens, (1981) Br. J. Pharmacol. 72 (4): 649-56). Some research, however, indicates that CBD can increase alertness, and attenuates the memory-impairing effect of THC. (Nicholson et al., June (2004) J Clin Psychopharmacol 24 (3): 305-13; Morgan et al., (2010) The British Journal of Psychiatry, 197:258-290). CBD may also decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, Chemistry & Biodiversity 4 (8): 1678-1692), for example reducing growth and invasiveness of aggressive human breast cancer cells (McAllister et al., 2007, Mol. Cancer Ther. 6 (11): 2921-7) Recent studies have also shown CBD to be as effective as atypical antipsychotics in treating schizophrenia (Zuardi et al., 2006, Braz. J. Med. Biol. Res. 39 (4): 421-429.), and studies also suggests that it may relieve symptoms of dystonia (Consroe, 1986, The International journal of neuroscience 30 (4): 277-282).

*Cannabis* produces CBD-carboxylic acid through the same metabolic pathway as THC, until the last step, where CBDA synthase performs catalysis instead of THCA synthase. See Marks et al. (2009) Journal of Experimental Botany 60 (13): 3715-3726.) and Meijer et al. I, II, III, and IV.

Non-limiting examples of CBD variants include CBD-C5, CBDM-C5, CBD-C4, CBDV-C3, CBD-C1, CBDA-C5, and CBDVA-C3.

Cannabigerol (CBG)

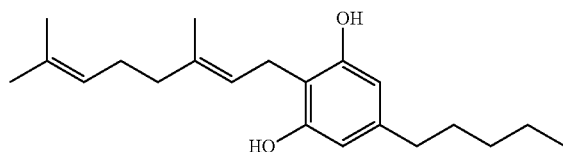 [SMILES: CCCCCc1cc(O)c(C/C=C(\C)CCC=C(C)C)c(O)c1]

CBG is a non-psychoactive cannabinoid found in the *Cannabis* genus of plants. Cannabigerol has been found to act as a high affinity α2-adrenergic receptor agonist, moderate affinity 5-HT1A receptor antagonist, and low affinity CB1 receptor antagonist. It also binds to the CB2 receptor. Cannabigerol has also been shown to reduce depression in animal models (US Patent Application Publication No. 2008-0031977). In particular CBG has been shown to have significant potential applications in the treatment of glaucoma, depression, Huntington's disease, MRSA, cachexia, and cancer (Craig et al. 1984, Experimental eye research 39 (3):251-259; U.S. Pat. No. 8,481,085; Valdeolivas et al. 2015, Neurotherapeutics January 12(1): 185-99; Appendino G et al., 2008, J. Nat Prod. August:71(8): 1427-30; Borrelli F et al. 2013, Biochem Pharmacol May1:85(9): 1306-16; Borrelli F. et al. 2014, Carcinogenesis December:35(12): 2787-97) Non-limiting examples of CBG variants include (E)-CBG-C5, (E)-CBGM-C5 A, (Z)-CBGA-C5 A, (E)-CBGV-C3, (E)-CBGA-C5 A, (E)-CBGAM-C5 A, and (E)-CBGVA-C3 A.

Cannabinol (CBN)

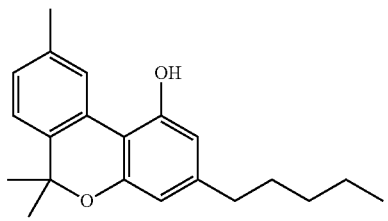 [SMILES: CCCCCc1cc(O)c2c(c1)OC(C)(C)c1ccc(C)cc1-2]

CBN is a mildly psychoactive cannabinoid found in trace amounts in *Cannabis*. CBN is a metabolite of THC. CBN has been shown to have significant applications in the treatment of anxiety disorder, insomnia, inflammation, convulsions, and bacterial infections. (Herring et al. Journal of Pharmacology and Experimental Therapeutics December 1999, 291 (3) 1156-1163.) CBN may be produced by aromatizing THC. The aromatization of THC to CBN may employ sulfur, chloranyl (tetrachloro-1,4-benzoquinone), and iodine. Pollastro et al. *J. Nat. Prod.* 2018, 81, 630-633. The reaction of THC to CBN is illustrated below (Reaction 1).

Reaction 1

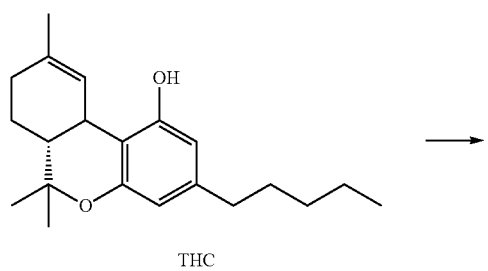

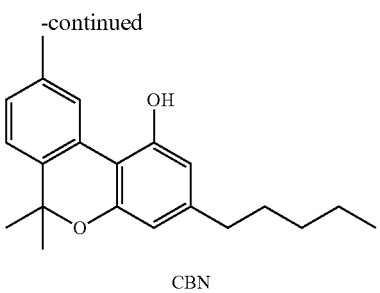

CBN may also be produced from CBD. CBN production from CBD requires isomerization of CBD to THC and aromatization of THC to CBN (Reaction 2). Isomerization of CBD to THC has been performed using acids, such as hydrogen chloride, pyridine hydrochloride, phosphoric acid, sulfamic acid, or zinc chloride. Adams et al. *J. Am. Chem. Soc.* 1940, 62, 9, 2402-2405. Aromatization of THC to CBN has been performed using the techniques described above.

Reaction 2

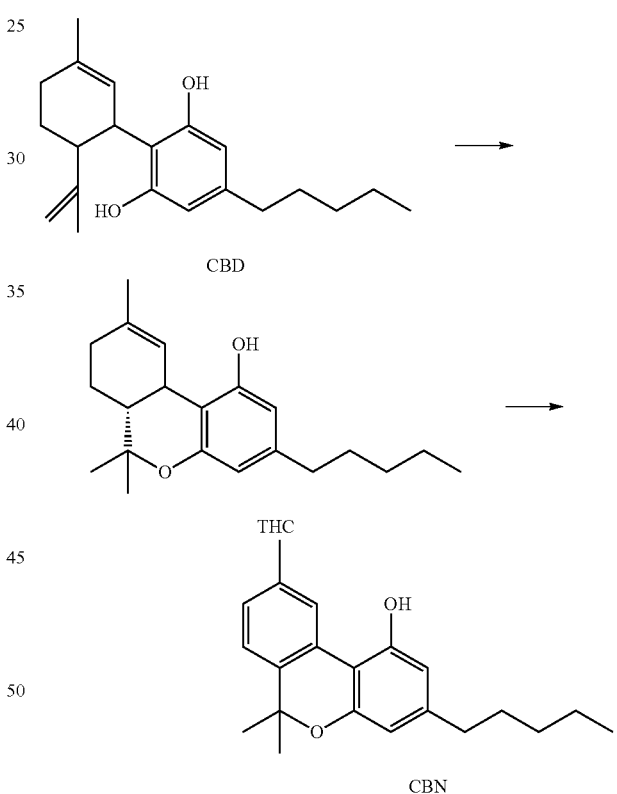

IIB. Terpenes

In addition to cannabinoids, *Cannabis* also produces over 120 different terpenes (Russo (2011) British Journal of Pharmacology, 163:1344-1364). Within the context and verbiage of this document the terms 'terpenoid' and 'terpene' are used interchangeably. In some embodiments, the present disclosure provides compositions comprising one or more terpenes or terpenoids.

In addition to many circulatory and muscular effects, some terpenes interact with neurological receptors. A few terpenes produced by *cannabis* plants also bind weakly to cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

Terpenoids are mainly synthesized in two metabolic pathways: mevalonic acid pathway (a.k.a. HMG-COA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by *cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

Terpenes are derived biosynthetically from units of isoprene, which have the molecular formula $C_5H_8$. The basic molecular formulae of terpenes are multiples of $(C_5H_8)_n$ where n is the number of linked isoprene units. The isoprene units may be linked together "head to tail" to form linear chains or they may be arranged to form rings.

In some embodiments, the present disclosure teaches compositions comprising the following terpenes: Alpha Pinene, Limonene, Beta Pinene, Alpha Phellandrene, Terpinolene, Nerolidol, Nerol, Myrcene, Beta Caryophyllene. In some embodiments, the present disclosure teaches compositions comprising Alpha Pinene, Limonene, Beta Pinene, Alpha Phellandrene, Terpinolene, Nerolidol, Nerol. Within the context of this disclosure, the term "terpene" includes Hemiterpenes, Monoterpenols, Terpene esters, Diterpenes, Monoterpenes, Polyterpenes, Triterpenes, Tetraterpenes, Terpenoid oxides, Sesterterpenes, Sesquiterpenes, Norisoprenoids, as well as their isomers, enantiomers, or derivatives. Within the context of this disclosure, the term terpene includes the α-(alpha), β-(beta), γ-(gamma), oxo-, isomers, or any combinations thereof.

Examples triterpenes of the present disclosure include ergosterol peroxide (1), cerevisterol (2), 3β,5α,9α-trihydroxy-ergosta-7,22-dien-6-one (3), inoterpene A (4), astradoric acid C (5), betulin (6), oleanolic acid (7), ursolic acid (8), hemisceramide (9), and 3,4-dihydro-5-methoxy-2-methyl-2-(4'-methyl-2'-oxo-3'-pentenyl)-9(7H)-oxo-2H-furo[3,4-h]benzopyran (10), Lupeol (2,3,6,23-tetrahydroxy-urs-12-en-28-oic acid), Novel (2,3,23-trihydroxy-urs-12-en-28-oic acid), Ganoderic Acid A, and Lanostanes.

Other examples of terpenes within the context of this disclosure include: 7,8-dihydro-alpha-ionone, 7,8-dihydro-beta-ionone, Acetanisole, Acetic Acid, Acetyl Cedrene, Anethole, Anisole, Benzaldehyde, Bergamotene (Alpha-cis-Bergamotene) (Alpha-trans-Bergamotene), Bisabolol (Beta-Bisabolol), Alpha Bisabolol, Borneol, Bornyl Acetate, Butanoic/Butyric Acid, Cadinene (Alpha-Cadinene) (Gamma-Cadinene), Cafestol, Caffeic acid, Camphene, Camphor, Capsaicin, Carene (Delta-3-Carene), Carotene, Carvacrol, Dextro-Carvone, Laevo-Carvone, Alpha-Caryophyllene, Beta-Caryophyllene, Caryophyllene oxide, Cedrene (Alpha-Cedrene) (Beta-Cedrene), Cedrene Epoxide (Alpha-Cedrene Epoxide), Cedrol, Cembrene, Chlorogenic Acid, Cinnamaldehyde, Alpha-amyl-Cinnamaldehyde, Alpha-hexyl-Cinnamaldehyde, Cinnamic Acid, Cinnamyl Alcohol, Citronellal, Citronellol, Cryptone, Curcumene (Alpha-Curcumene) (Gamma-Curcumene), Decanal, Dehydrovomifoliol, Diallyl Disulfide, Dihydroactinidiolide, Dimethyl Disulfide, Eicosane/Icosane, Elemene (Beta-Elemene), Estragole, Ethyl acetate, Ethyl Cinnamate, Ethyl maltol, Eucalyptol/1,8-Cineole, Eudesmol (Alpha-Eudesmol) (Beta-Eudesmol) (Gamma-Eudesmol), Eugenol, Euphol, Farnesene, Farnesol, Fenchol (Beta-Fenchol), Fenchone, Geraniol, Geranyl acetate, Germacrenes, Germacrene B, Guaia-1(10), 11-diene, Guaiacol, Guaiene (Alpha-Guaiene), Gurjunene (Alpha-Gurjunene), Herniarin, Hexanaldehyde, Hexanoic Acid, Humulene (Alpha-Humulene) (Beta-Humulene), Ionol (3-oxo-alpha-ionol) (Beta-Ionol), Ionone (Alpha-Ionone) (Beta-Ionone), Ipsdienol, Isoamyl Acetate, Isoamyl Alcohol, Isoamyl Formate, Isoborneol, Isomyrcenol, Isopulegol, Isovaleric Acid, Isoprene, Kahweol, Lavandulol, Limonene, Gamma-Linolenic Acid, Linalool, Longifolene, Alpha-Longipinene, Lycopene, Menthol, Methyl butyrate, 3-Mercapto-2-Methylpentanal, Mercaptan/Thiols, Beta-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (Beta-Myrcene), Gamma-Muurolene, Nepetalactone, Nerol, Nerolidol, Neryl acetate, Nonanaldehyde, Nonanoic Acid, Ocimene, Octanal, Octanoic Acid, P-Cymene, Pentyl butyrate, Phellandrene, Phenylacetaldehyde, Phenylethanethiol, Phenylacetic Acid, Phytol, Pinene, Beta-Pinene, Propanethiol, Pristimerin, Pulegone, Quercetin, Retinol, Rutin, Sabinene, Sabinene Hydrate, cis-Sabinene Hydrate, trans-Sabinene Hydrate, Safranal, Alpha-Selinene, Alpha-Sinensal, Beta-Sinensal, Beta-Sitosterol, Squalene, Taxadiene, Terpin hydrate, Terpineol, Terpine-4-ol, Alpha-Terpinene, Gamma-Terpinene, Terpinolene, Thiophenol, Thujone, Thymol, Alpha-Tocopherol, Tonka Undecanone, Undecanal, Valeraldehyde/Pentanal, Verdoxan, Alpha-Ylangene, Umbelliferone, or Vanillin.

Derivatives of terpenes include terpenoids, hemiterpenoids, monoterpenoids, sesquiterpenoids, sesterterpenoid, sesquarterpenoids, tetraterpenoids, triterpenoids, tetraterpenoids, polyterpenoids, isoprenoids, and steroids. Terpenoids, a.k.a. isoprenoids, are a large and diverse class of naturally occurring organic chemicals similar to terpenes, derived from five-carbon isoprene units assembled and modified in thousands of ways. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

Brief descriptions and chemical structures for several of the major terpenes are provided below.

Alpha Pinene

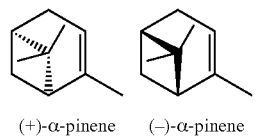

(+)-α-pinene    (−)-α-pinene

α-Pinene is a monoterpene common in nature, also with a plethora of effects on mammals and humans. It acts as an acetylcholinesterase inhibitor, which aids memory and counteracts the short-term memory loss associated with $\Delta^9$-THC intoxication, is an effective antibiotic agent, and shows some activity against MRSA. In addition, α-pinene is a bronchodilator in humans and has anti-inflammatory properties via the prostaglandin E-1 pathway (Russo 2011, *British Journal of Pharmacology*, 163:1344-1364).

Limonene

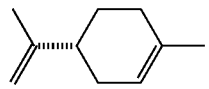

D-Limonene, also known as limonene, is a monoterpenoid that is widely distributed in nature and often associated with citrus. It has strong anxiolytic properties in both mice and humans, apparently increasing serotonin and dopamine in mouse brain. D-limonene has potent anti-depressant activity when inhaled. It is also under investigation for a variety of different cancer treatments, with some focus on its hepatic metabolite, perillic acid. There is evidence for activity in the treatment of dermatophytes and gastro-oesophageal reflux, as well as having general radical scavenging properties (Russo 2011, *British Journal of Pharmacology*, 163:1344-1364).

Beta-Pinene

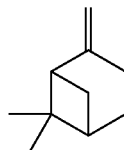

Beta-pinene, also referred to herein as β-terpene, is a monoterpene found in plants. Beta-pinene has anti-inflammatory, bronchodilator, and anti-anxiety effects. The therapeutic effect of beta-pinene is described in the following articles which is incorporated by reference herein in its entirety. Salehi et al. Biomolecules. (2019). 9(11):738.

Alpha Phellandrene

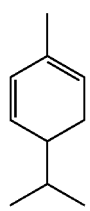

Alpha phellandrene, also referred to herein as α-phellandrene, is a monoterpene with a citrusy minty scent. Preliminary studies show that this terpene stimulates the immune system, provides energy, and has anti-cancer, anti-fungal, and anti-pain properties. The following study highlights alpha phellandrene's potential therapeutic benefit and is incorporated by reference herein in its entirety: Hsieh et al. Nutr Cancer. 2014; 66(6):970-9.

Terpinolene

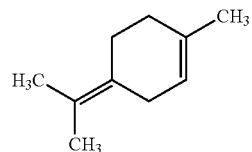

Terpinolene is a common terpene present in *Cannabis* recognizable for its woody aroma and citrus and floral notes. Terpinolene has mild sedative effects. Early research shows terpinolene benefits may include antifungal, antibacterial, and anticancer properties in addition to potentially calming the central nervous system. The following article describes the effect of terpinolene and is incorporated by reference herein in its entirety: Ito et al. J Nat Med 2013; 67:833-837.

Nerolidol

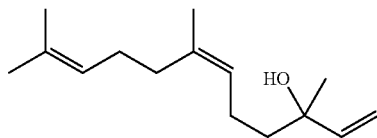 [SMILES: C=CC(C)(O)CC/C=C(/C)CCC=C(C)C]

Nerolidol is a sesquiterpene that is often found in citrus peels that exhibits a range of interesting properties. It acts as a sedative, inhibits fungal growth, and has potent anti-malarial and antileishmanial activity. It also alleviated colon adenomas in rats (Russo 2011, *British Journal of Pharmacology*, 163:1344-1364).

Nerol

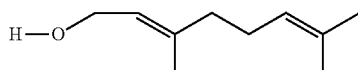

Nerol is a monoterpene alcohol. Nerol is used to treat sepsis along with bacterial infections and is also effective at soothing and healing topical conditions such as acne and minor contusions. Nerol is also combined with other additives to create popular fruit flavors like raspberry and red apple.

Myrcene

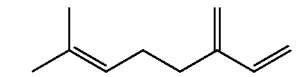

Myrcene is a monoterpenoid also found in *cannabis*, and has a variety of pharmacological effects. It is often associated with a sweet fruit like taste. It reduces inflammation, aids sleep, and blocks hepatic carcinogenesis, as well as acting as an analgesic and muscle relaxant in mice. When β-myrcene is combined with Δ9-THC it may intensify the sedative effects of Δ9-THC, causing the well-known "couch-lock" effect that some *cannabis* users experience (Russo 2011, *British Journal of Pharmacology*, 163:1344-1364).

Beta Caryophyllene

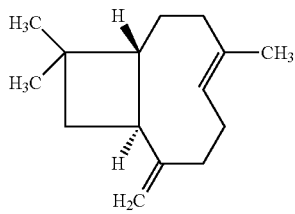

β-Caryophyllene (BCP) is often the most predominant sesquiterpenoid in *cannabis*. It is less volatile than the monoterpenoids, thus it is found in higher concentrations in material that has been processed by heat to aid in decarboxylation. It is very interesting in that it is a selective full agonist at the CB2 receptor, which makes it the only phytocannabinoid found outside the *cannabis* genus. In addition, it has anti-inflammatory and gastric cytoprotective properties, and may even have anti-malarial activity.

IIC. Sources of Cannabinoid and Terpenes

In some embodiments, the presently disclosed compositions/formulations include a cannabinoid and/or a terpene component. Cannabinoids and terpenes from any source may be used in the compositions of the present disclosure. In some embodiments, cannabinoid and or terpenes are extracted from *Cannabis* plants. In some embodiments, the cannabinoids and terpenes described herein are provided as *Cannabis* extracts (also interchangeably referred to herein as "*Cannabis* plant extracts.") In some embodiments, the cannabinoid and/or terpene extracts are produced from aerial parts of *Cannabis* plants, e.g., the stalks, stems, leaves, and seeds.

*Cannabis* plant extracts can be produced according to methods known in the art. For example, suitable extraction methods include maceration, percolation, solvent extraction, steam distillation (giving you essential oil) or vaporization. General protocols for the preparation of *Cannabis* extracts from *cannabis* plant material are described in U.S. Pat. Nos. 8,603,515 and 9,730,911, both incorporated by reference herein.

Solvent extraction may be carried out using essentially any solvent that dissolves cannabinoids/cannabinoid acids, such as for example C1 to C5 alcohols (e.g. ethanol, methanol), C4-C12 alkanes (e.g. hexane or butane), Norflurane (HFA134a), HFA227, and carbon dioxide. When solvents such as those listed above are used, the resultant primary extract typically contains non-specific lipid-soluble material or "ballast" e.g. waxes, wax esters and glycerides, unsaturated fatty acid residues, terpenes, carotenes, and flavonoids. The primary extract may be further purified for example by "winterization", which involves chilling to −20° C. followed by filtration to remove waxy ballast, supercritical or subcritical extraction, vaporization, distillation, and chromatography.

Additional extraction techniques for cannabinoids, including vaporizer-based approaches, can be found in U.S. Pat. Nos. 7,700,368, 10,159,908, U.S. Pub. No. 2019/0151771, U.S. Pub. No. 2018/0078874, U.S. Pub. No. 2020/0080021, U.S. Pub. No. 2020/0048214, U.S. Pub. No. 2020/0048215, and U.S. patent Ser. No. 10/555,914, each of which is incorporated by reference herein in its entirety.

In some embodiments, terpenes are extracted from *Cannabis* using a vacuum-drying oven. Vacuum-drying ovens remove water, solvents, and terpenes from the *Cannabis*. The solution of water, solvents, and terpenes can be separated by filtration to purify terpenes.

In some embodiments, terpenes and/or cannabinoids are extracted from *Cannabis* using carbon dioxide. In some embodiments, the carbon dioxide is supercritical carbon dioxide (scCO$_2$). Carbon dioxide extraction may occur at very low temperatures, preventing compounds like terpenes and cannabinoids from degrading. U.S. Pat. No. 9,744,200 and International Application No. 2016/200438 describe carbon dioxide extraction processes and are each incorporated by reference herein in their entireties.

In some embodiments, the compositions of the present disclosure comprise one or more components are derived from sources other than the *Cannabis* plant (e.g., from other organisms, or chemically synthesized). For example, the compositions of the present disclosure can, in some embodiments, comprise cannabinoids and/or terpenes produced via standard chemical, biochemical, or biocatalytic methods. Persons having skill in the art will be familiar with various synthesis methods, including those of U.S. Pat. No. 9,359,625 and Taura et al. 1996, The Journal of Biological Chemistry, Vol. 271, No. 21, p. 17411-17416.

Additionally, cannabinoids and terpenes of the present disclosure can be commercially sourced. For example, CBD and THC can be purchased from Sigma-Aldrich Company Ltd, Fancy Road, Poole Dorset, BH12 4QH, or may be chemically synthesized. Beta-pinene and limonene can also be purchased from Sigma-Aldrich Company Ltd, Fancy Road, Poole Dorset, BH12 4QH.

Some cannabinoids do not accumulate at high levels in *cannabis* plant material. In some embodiments, these cannabinoids can be produced by chemical means. For example, in some embodiments, cannabinoids such as cannabinol are created from THC or CBD as described in Pollastro et al. and Adams et al. which are each incorporated by reference herein in their entirety: Pollastro et al. J. Nat. Prod. 2018, 81, 3, 630-633; Adams et al. J. Am. Chem. Soc. 1940, 62, 9, 2402-2405.

In some embodiments, the cannabinoids and terpenes of the present disclosure are pure isolates. In some embodiments, cannabinoids and/or terpenes are provided as a complex mixture (e.g., within a complex extract). A complex mixture contains two or more cannabinoids and/or terpenes. For example, in some embodiments, CBD and THC are provided as a solution containing 50% CBD and 50% THC.

In some embodiments, the cannabinoids described herein are provided in their acidic precursors. For example, CBD may be provided as cannabidiolic acid (CBDA). In some embodiments, formulations comprising acidic forms of cannabinoids are heated up prior to use to decarboxylate the acidic form. For example, heating of CBDA at temperatures of 110° C. or higher results in production of CBD.

IIIA. Mushrooms

Mushrooms are filamentous fungi with fruiting bodies. There are over 50,000 species of mushrooms in the world. Saprotrophic mushrooms release acids and enzymes to break down dead tissue into smaller molecules. Mycorrhizal mushrooms are symbiotic with plants, bringing moisture, phosphorous, and other nutrients to their hosts. Endophytic fungi live in a mutualistic relationship with plants for at least a part of their life cycle. Many of the aforementioned mushrooms are edible and have potential health benefits. The following references describe the health benefits of mushrooms and are each incorporated by reference in its entirety: Qu et al. Oncol Lett. (2017): 14(6): 7467-7472.

Brief descriptions of mushrooms of interest are provided below.

*Hericium erinaceus*, also referred to as Lion's mane mushroom, monkey head mushroom, bearded tooth mushroom, satyr's beard, bearded hedgehog mushroom, pom pom mushroom, or bearded tooth fungus, is a fungus native to North America, Europe, and Asia. *Hericium erinaceus* can be identified by its long spines (greater than 1 cm length), occurrence on hardwoods, and tendency to grow a single clump of dangling spines. FIG. 1 shows a picture of a *Hericium erinaceus* mushroom. *Hericium erinaceus* produces edible fruiting bodies that have uses as food and in traditional method. *Hericium erinaceus* is taken to improve overall mental function and memory.

*H. erinaceus* contains diverse phytochemicals, including polysaccharides, such as β-glucan, as well as hericenones and erinacines. Other compounds include hexadecanoic acid (26%), linoleic acid (13.1%), phenylacetaldehyde (8.9%) and benzaldehyde (3%), and volatile oils, such as 2-methyl-3-furanthiol, 2-ethylpyrazine and 2,6-diethylpyrazine. Low concentrations of ergosterol are also present in *H. erinaceus*. Additionally, the compounds hericenones and erinacines may be isolated from the fruiting body and mycelium of *H. erinaceus*. Hericenones and erinacines each promote brain health, delaying neuronal cell death in rats with neurodegenerative diseases, such as ischemic stroke, Parkinson's disease, Alzheimer's disease, and depression. The following references which are each incorporated by reference herein in their entirety describe *H. erinaceus*: He et al. International Journal of Biological Macromolecules (2017) 97: 228-237; Khan et al. Journal of Complementary and Integrative Medicine (2013): 10(1); Zhang et al. Bioorg Med Chem. 2015 Nov. 15; 25(22):5078-82. Li et al. Behavioral Neurology (2018): Article ID 5802634, 10 pages.

*Cordyceps militaris* is a species of ascomycete fungi that has been shown to act as a pro-sexual, anti-inflammatory, anti-oxidant anti-aging, anti-tumour/anti-cancer/anti-leukemic, anti-proliferative, anti-metastatic, immunomodulatory, anti-microbial, anti-bacterial, anti-viral, anti-fungal, anti-protozoal, insecticidal, larvicidal, anti-fibrotic, steroidogenic, hypoglacaemic, hypolipidaemic, anti-angiogenetic, anti-diabetic, anti-HIV, anti-malarial, anti-fatigue, neuroprotective, liver-protective, reno-protective, and pneumo-protective.

Figure 2:
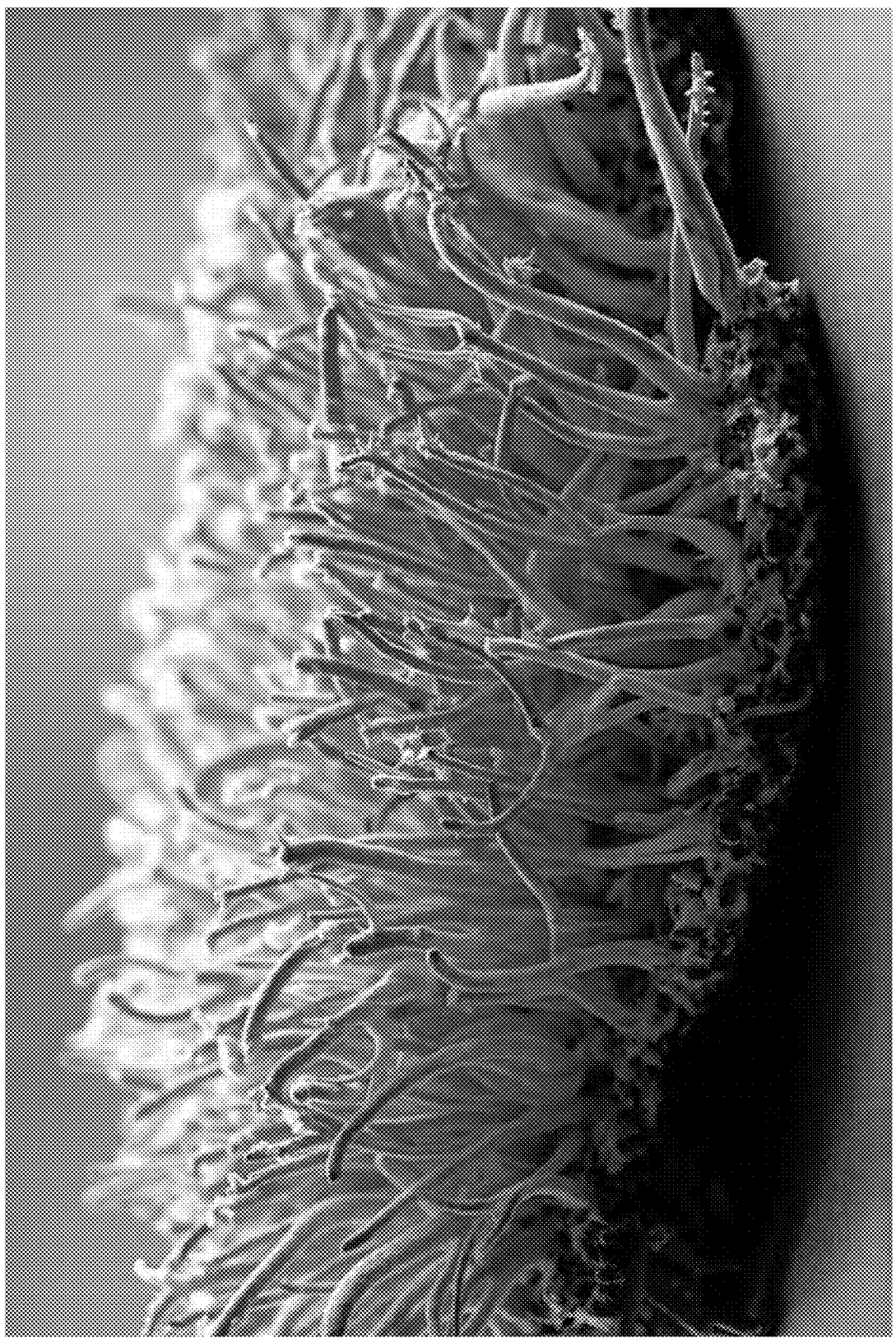
FIG. 2 shows a picture of a *Cordyceps militaris* mushroom.

*Cordyceps militaris* forms 20-50 mm high, club-shaped and orange/red fruiting bodies, which grow out of dead underground pupae. The club is covered with the stroma, into which the actual fruit bodies, the perithecia, are inserted. The surface appears roughly punctured. The inner fungal tissue is whitish to pale orange. FIG. 2 shows a picture of a *Cordyceps militaris* mushroom.

*C. militaris* contains 3'-deoxyadenosine, adenosine, and cordycepin. Cordycepin is a Cordycepin is a purine nucleoside antimetabolite and antibiotic with potential antineoplastic, antioxidant, and anti-inflammatory activities. The following references which are incorporated by reference herein in their entirety describe medicinal uses of *C. militaris*: Das et al. Fitoterapia. (2010): 81(8): 961-968.; Smiderle et al. PLOS One. 2014; 9(10): e110266; Tuli et al. 3 Biotech. (2014): 4(1):1-12.

*Trametes versicolor*, also known as *Coriolus versicolor, Polyporus versicolor*, and Turkey Tail mushroom, is a common polypore mushroom found throughout the world. *T. versicolor* is known to boost the immune system and have anticarcinogenic properties.

Figure 3:
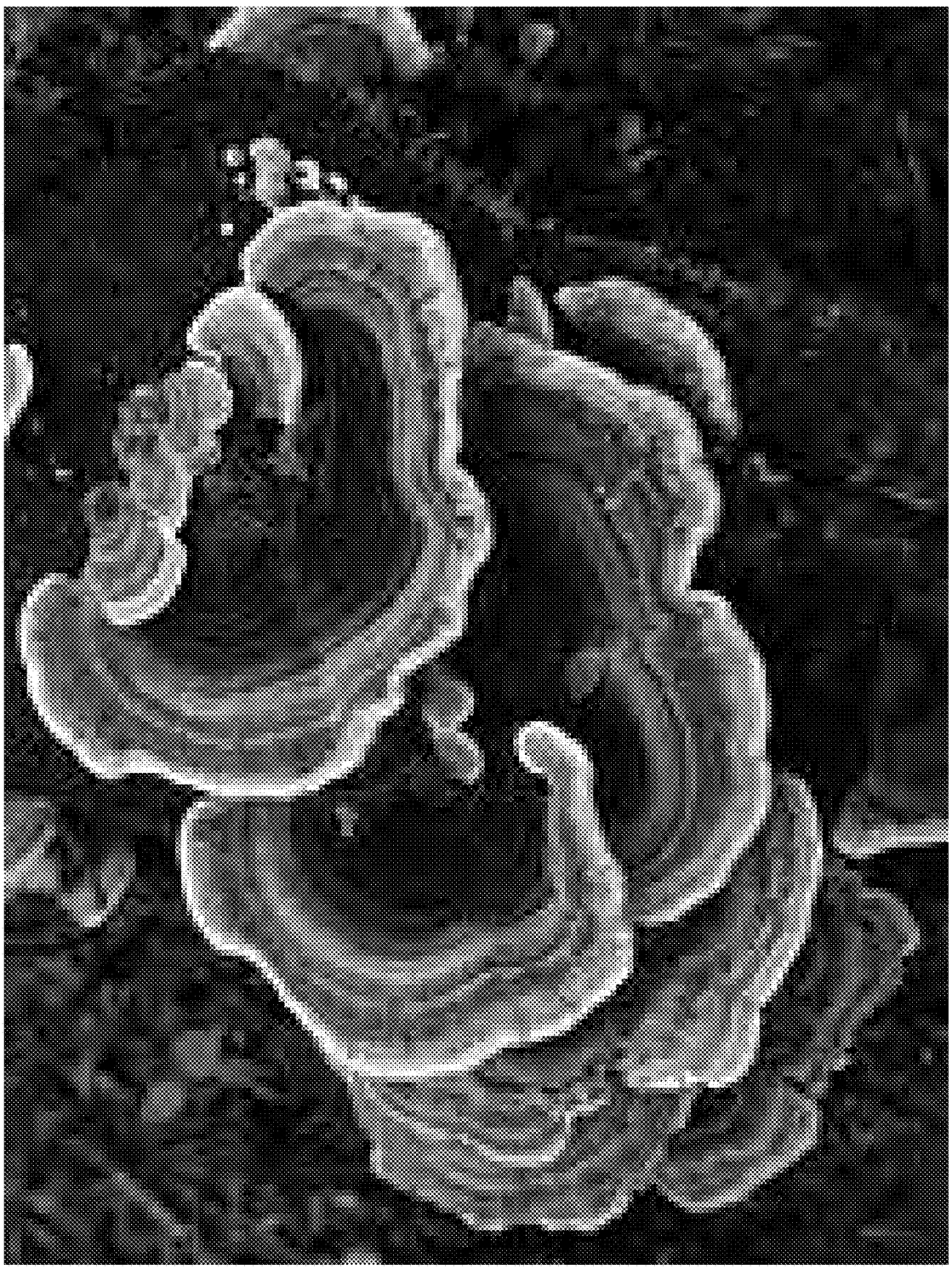
FIG. 3 shows a picture of a *T. versicolor* mushroom.

*Trametes versicolor* obtains its nickname of Turkey Tail, because its shape and colors are similar to a wild turkey. FIG. 3 shows a picture of a *T. versicolor* mushroom.

*T. versicolor* contains the polysaccharopeptide (PSP), proteins, amino acids, and other bioactive substances. The monosaccharide composition of *T. versicolor* is glucose, mannose, galactose, xylose, and fucose. The following reference which is incorporated by reference herein in their entirety describes medicinal uses of *T. versicolor*: Dou et al. Progress in Molecular Biology and Translational Science (2019) 163: 361-381.

*Ganoderma lingzhi*, also known as reishi, is a polypore fungus used in traditional Chinese medicine. *Ganoderma lingzhi* contains diverse phytochemicals, including triterpenes, polysaccharides, coumarin, mannitol, alkaloids, ganoderol, ganoderenic acid, ganoderiol, ganodermanontriol, lucidadiol, and ganodermadiol. *Ganoderma lingzhi* may have the potential to enhance tumor response and stimulate host immunity. The following references describe uses of *Ganoderma lingzhi* and are incorporated by reference herein in their entirety: Lu et al. International Journal of Biological Macromolecules. (2020) 150: 765-774; Yuen et al. Nutrition and Cancer. (2005) 1: 11-17.

Figure 4:
FIG. 4 shows a picture of a *G. lingzhi* mushroom.

The *G. lingzhi* mushroom has a red-varnished, kidney-shaped cap and peripherally inserted stem, which gives it a distinct fan-like appearance. It lacks gills on its underside, and instead releases its spores via fine pores. Depending on the age, the pores on its underside may be white or brown. FIG. 4 shows a picture of a *G. lingzhi* mushroom.

*Grifola frondosa*, sometimes called hen of the woods and the maitake, is a soft-fleshed polypore that grows at the base of trees. *Grifola frondosa* is rich in nutrients, such as amino acids, polysaccharids, and trace elements. *G. frondosa* has antioxidant and immunomodulatory effects. Mizuno et al. describes *G. frondosa*, and is incorporated by reference herein in its entirety: Mizuno et al. Food Reviews International (2009) 1: 135-149.

Figure 5:
FIG. 5 shows a picture of a *G. frondosa* mushroom.

*G. frondosa* grows from an underground tuber-like structure known as a sclerotium, about the size of a potato. The fruiting body, occurring as large as 100 centimeters (cm), rarely 150 cm, is a cluster consisting of multiple grayish-brown caps which are often curled or spoon-shaped, with wavy margins and 2-10 cm broad. The undersurface of each cap bears about one to three pores per millimeter (mm), with the tubes rarely deeper than 3 mm. The milky-white stipe (stalk) has a branchy structure and becomes tough as the mushroom matures. FIG. 5 shows a picture of a *G. frondosa* mushroom.

*Lentinula edodes*, or the shiitake mushroom, is an edible mushroom that contains lentinan ([1,3]-beta-D-glucan). *L. edodes* has potential anticancer, antiviral, antioxidant, antifungal, hypoglycemic, and immunostimulating properties. Caglarirmak et al. describes *L. edodes* and is incorporated by reference herein in its entirety: Caglarirmak et al. Food Chemistry. (2007). 105(3): 1188-1194.

Figure 6:
FIG. 6 shows a picture of a *L. edodes* mushroom.

The fruiting bodies of *L. edodes* are generally light-coloured to reddish brown or black, with a convex to flat pileus (cap) supported by a fibrous stipe (stalk). The pileus can be 2-25 cm in diameter, depending on the species, and features white gills on the underside. *L. edodes* produces white spores. FIG. 6 shows a picture of a *L. edodes* mushroom.

*Inonotus obliquus*, also known as chaga or chaga sclerotia, is a fungus in the family Hymenochaetaceae. *I. obliquus* contains high concentrations of melanin and oxalate. *I. obliquus* is used for different therapeutic indications: as an anthelminthic, as an antitubercular, to cure digestive disorders (gastritis, ulcers, etc.), or even to prevent cardiac or hepatic illnesses. *Inonotus obliquus* extracts have been found to inhibit hepatitis C virus, and human immunodeficiency virus, and demonstrated strong antioxidant and immunostimulatory activities. Gery et al. describes the properties of *I. obliquus* and is incorporated by reference herein in its entirety: Gery et al. Integr. Cancer Ther. (2018) 17(3): 832-843 describes the properties of *I. obliquus* and is incorporated by reference herein in its entirety.

Figure 7:
FIG. 7 shows a picture of a *I. obliquus* mushroom.
Figure 8:
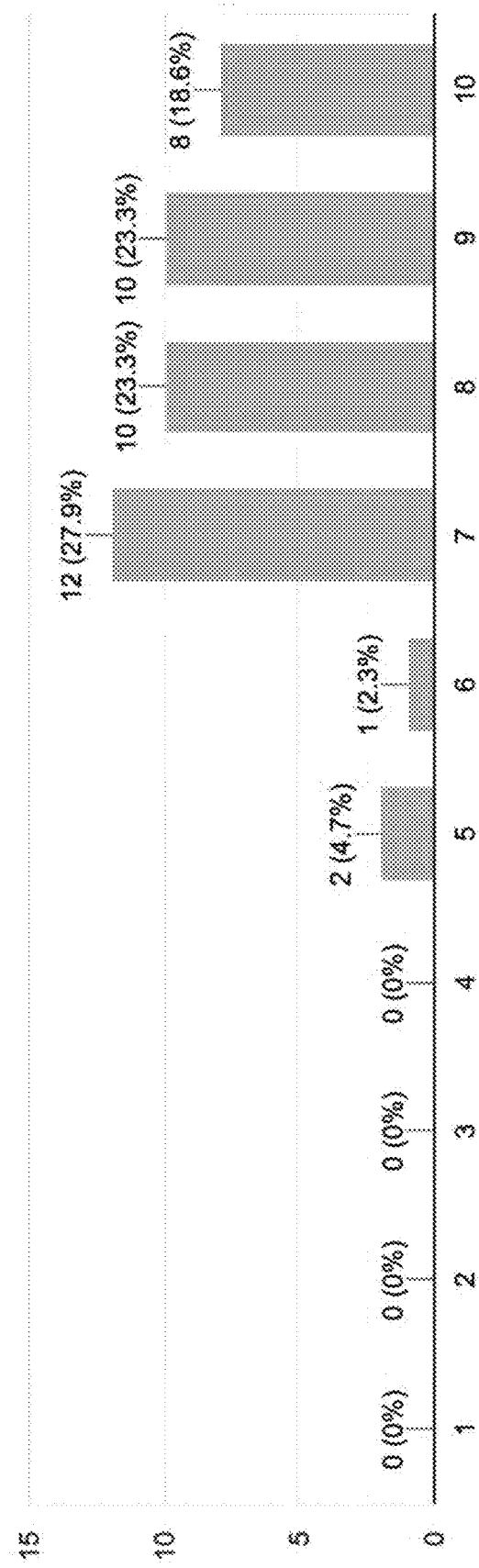
FIG. 8 depicts the effects of sample 1 from Example 1 on alertness.
Figure 9:
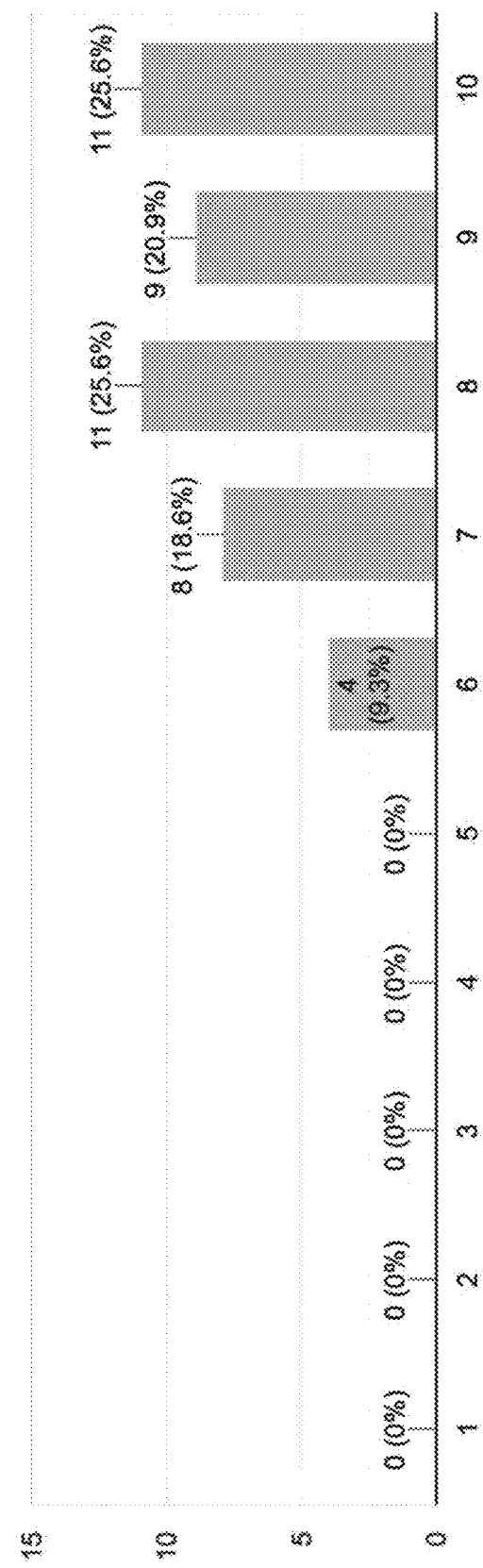
FIG. 9 depicts the effects of sample 1 from Example 1 on mental focus.
Figure 10:
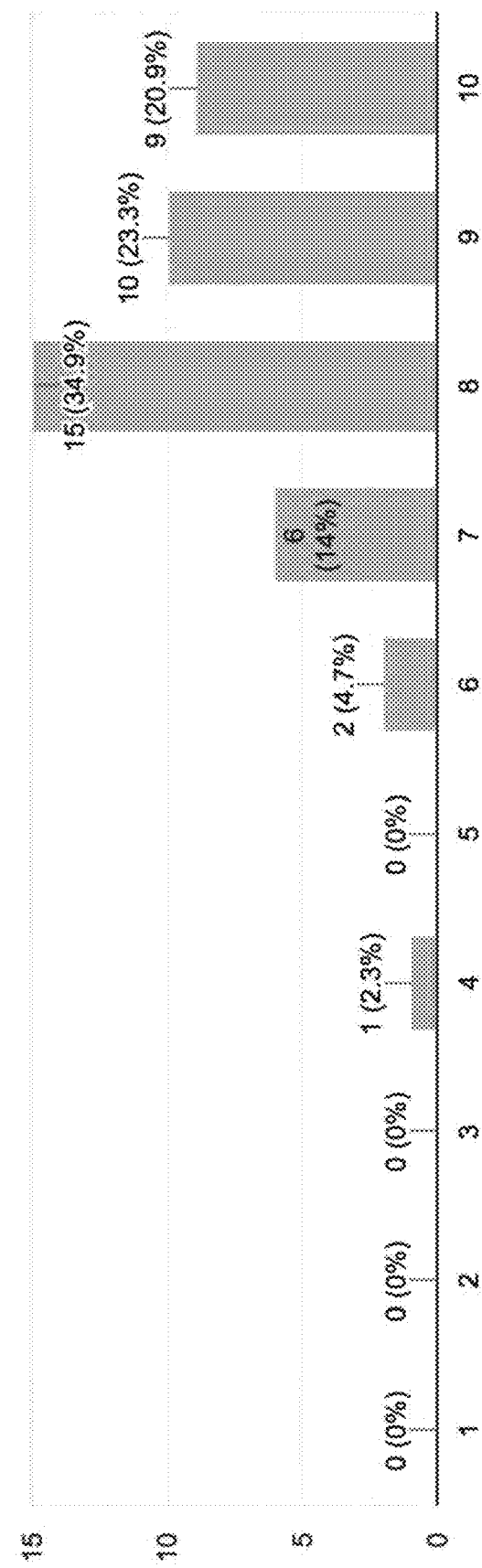
FIG. 10 depicts the effects of sample 1 from Example 1 on energy levels.
Figure 11:
FIG. 11 depicts the effects of sample 1 from Example 1 on ability to function normally.
Figure 12:
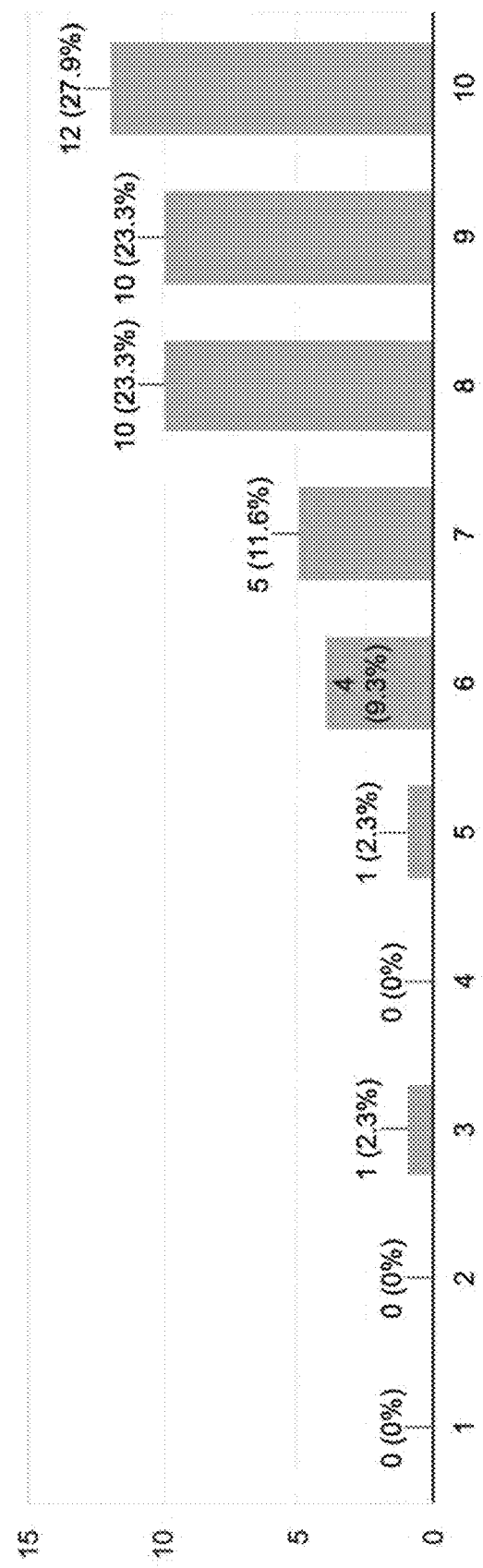
FIG. 12 depicts the effects of sample 1 from Example 1 on mood enhancement.
Figure 13:
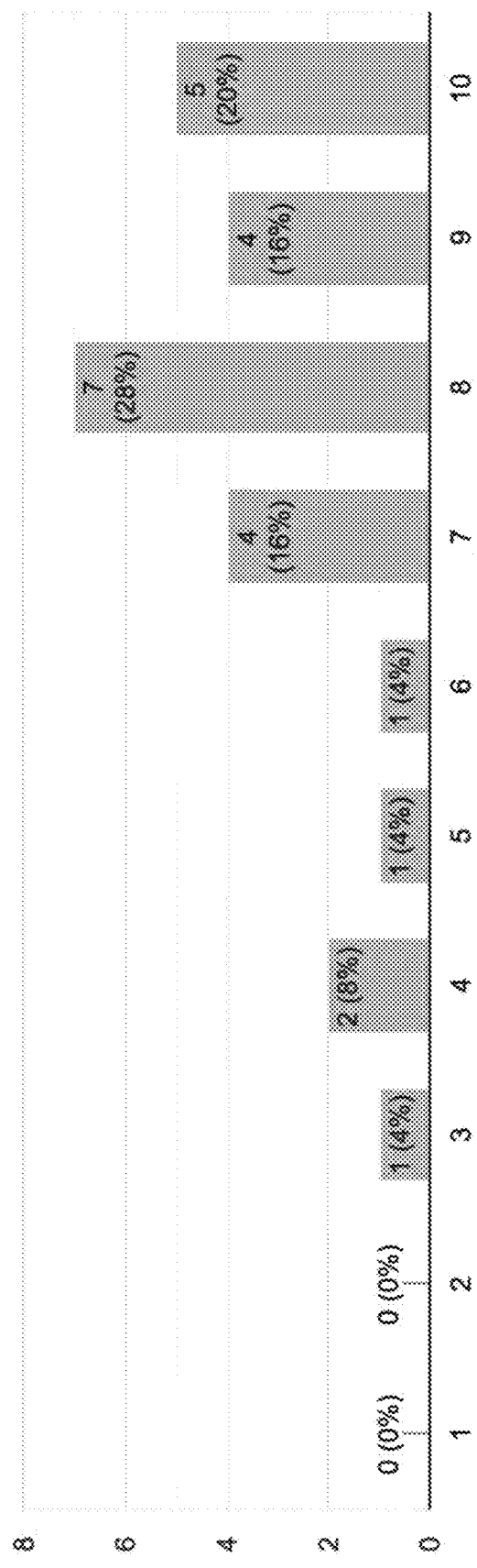
FIG. 13 depicts the effects of sample 3 from Example 1 on alertness.
Figure 14:
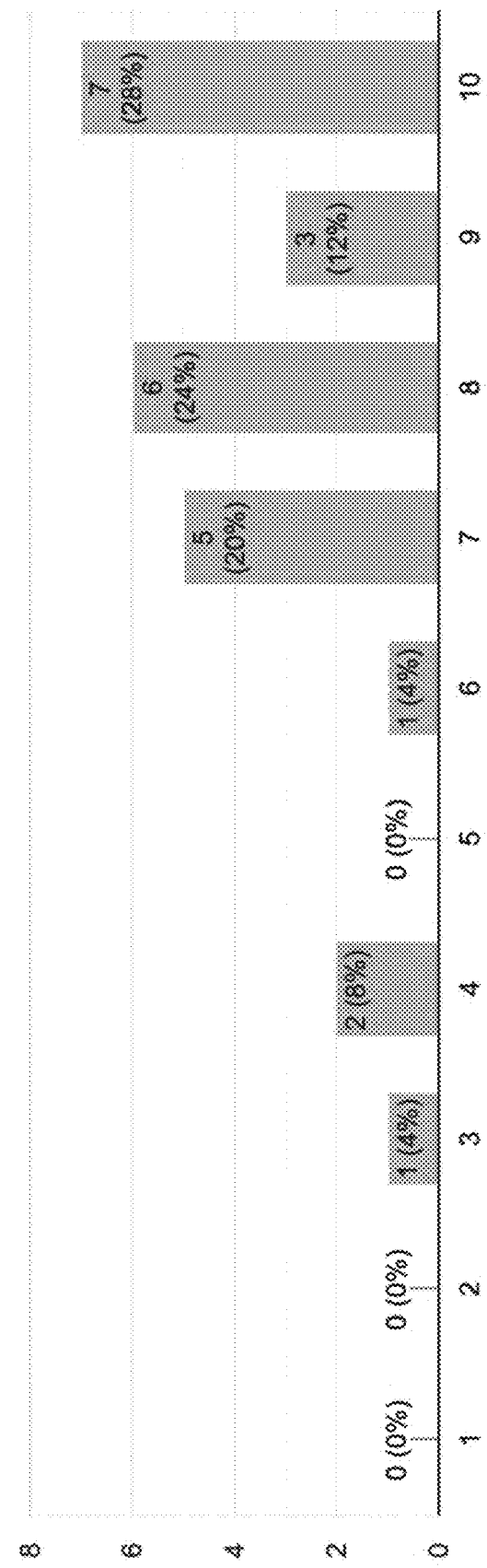
FIG. 14 depicts the effects of sample 3 from Example 1 on mental focus.
Figure 15:
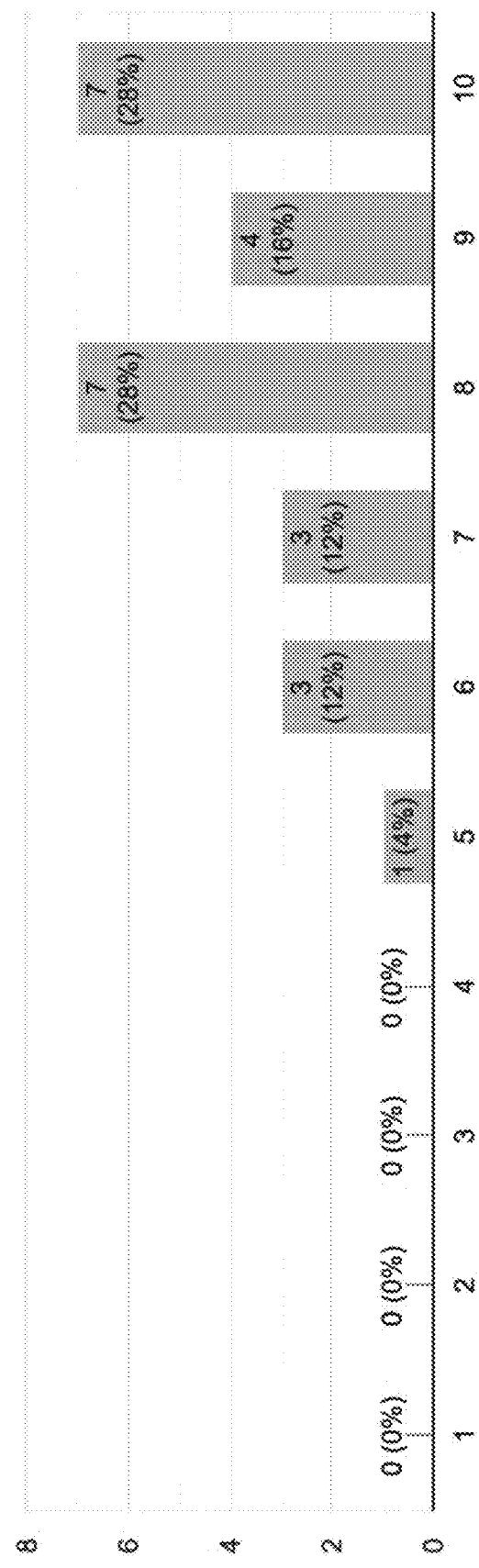
FIG. 15 depicts the effects of sample 3 from Example 1 on energy levels.
Figure 16:
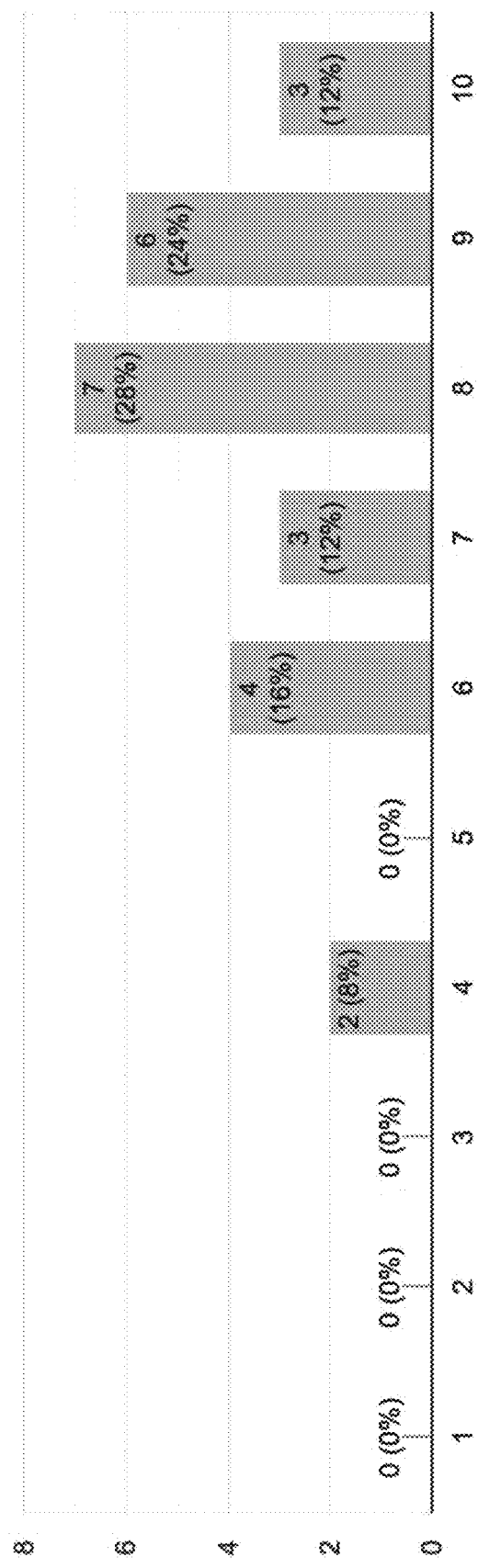
FIG. 16 depicts the effects of sample 3 from Example 1 on ability to function normally.
Figure 17:
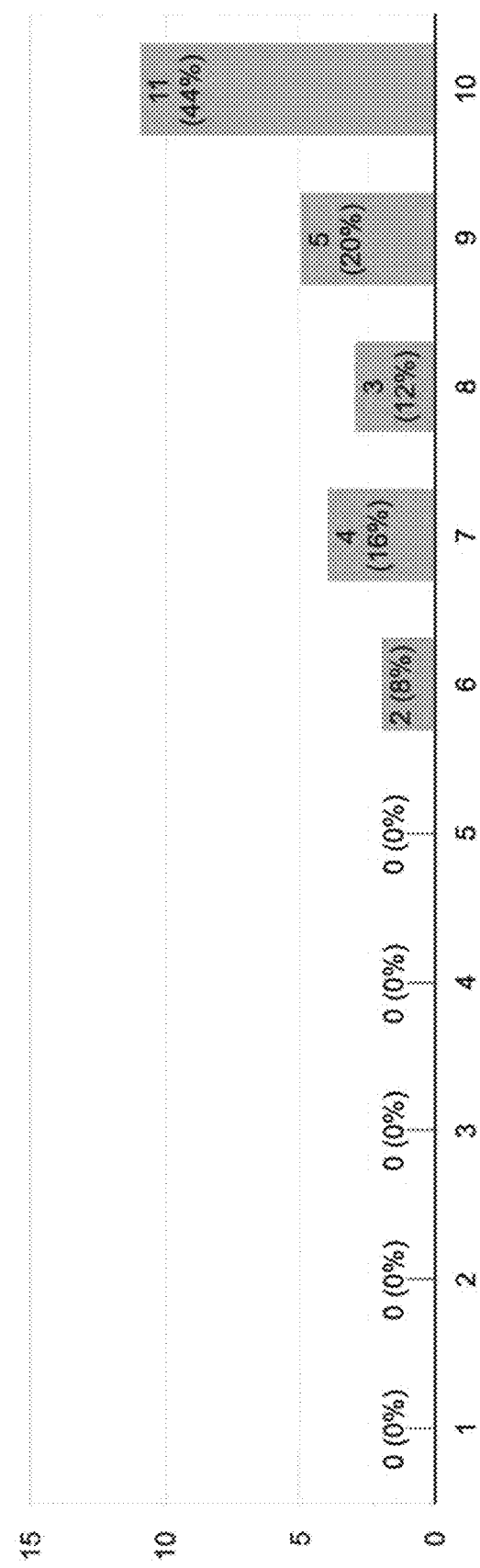
FIG. 17 depicts the effects of sample 3 from Example 1 on mood enhancement.
Figure 18:
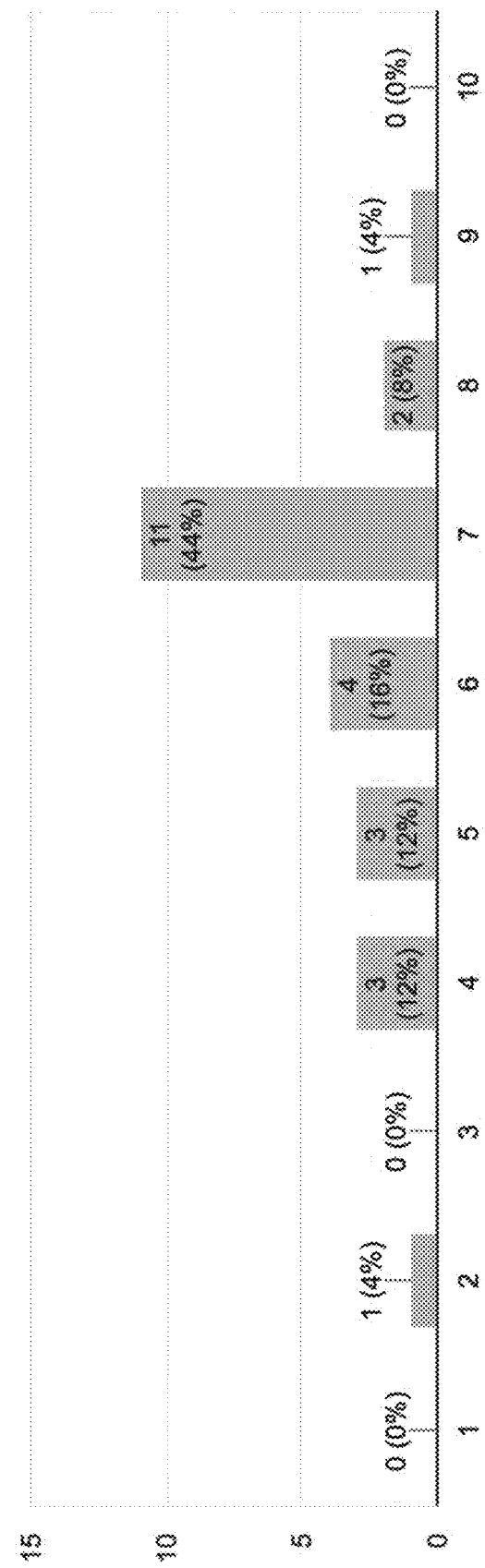
FIG. 18 depicts the effects of sample 3 from Example 1 on level of intoxication.
Figure 19:
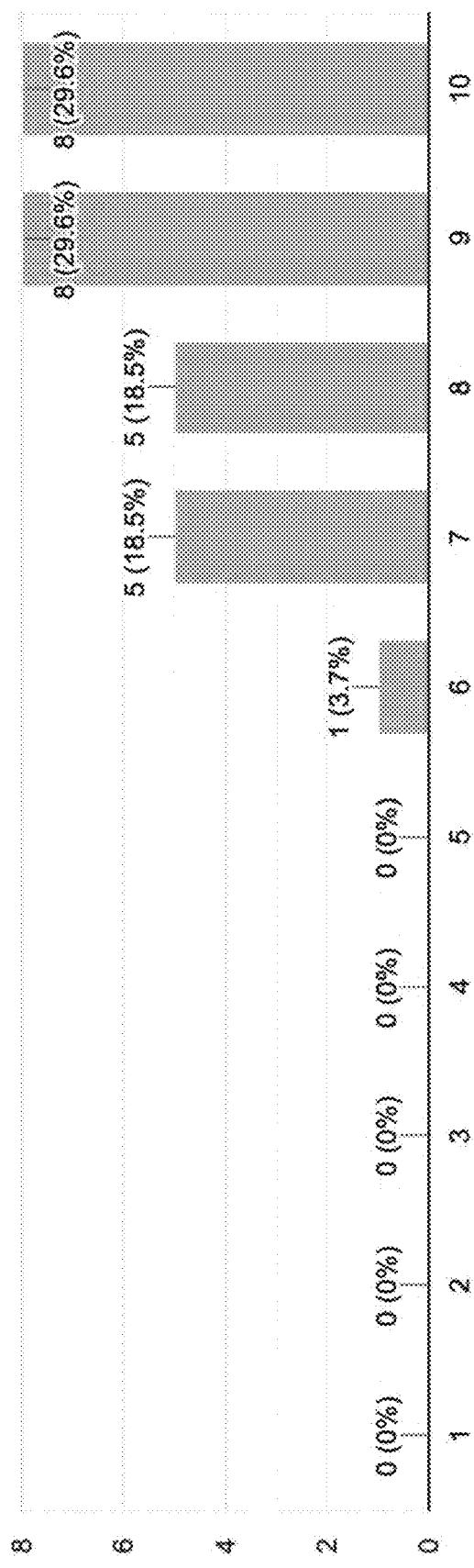
FIG. 19 depicts the effects of sample 2 from Example 1 on falling sleep.
Figure 20:
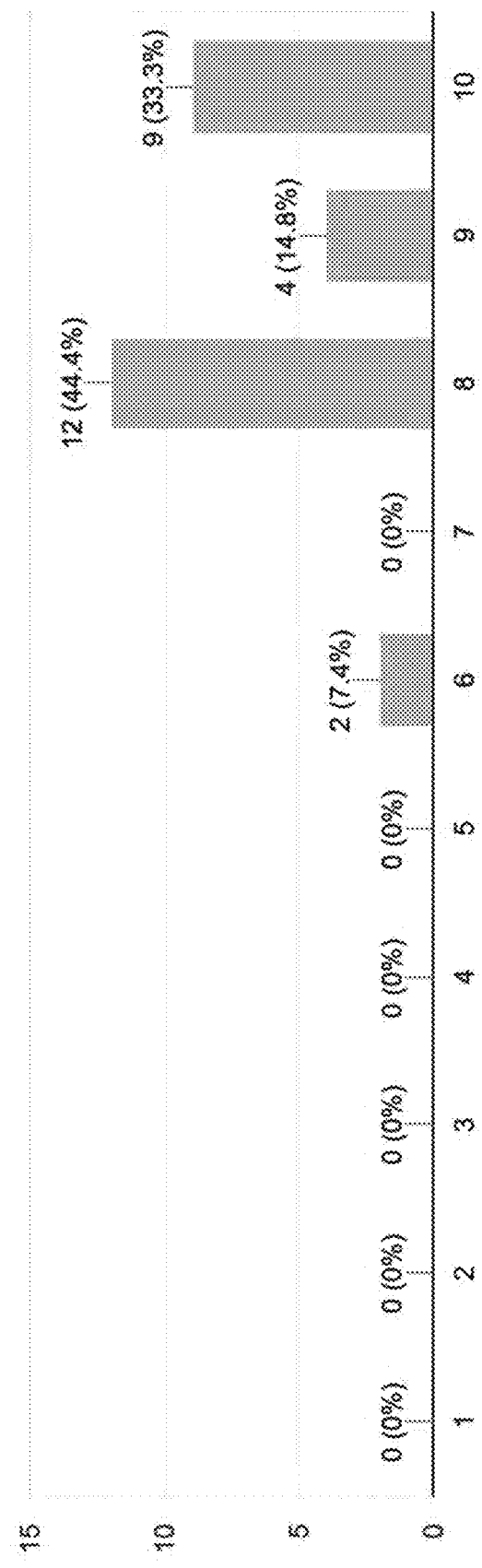
FIG. 20 depicts the effects of sample 2 from Example 1 on sleep quality.
Figure 21:
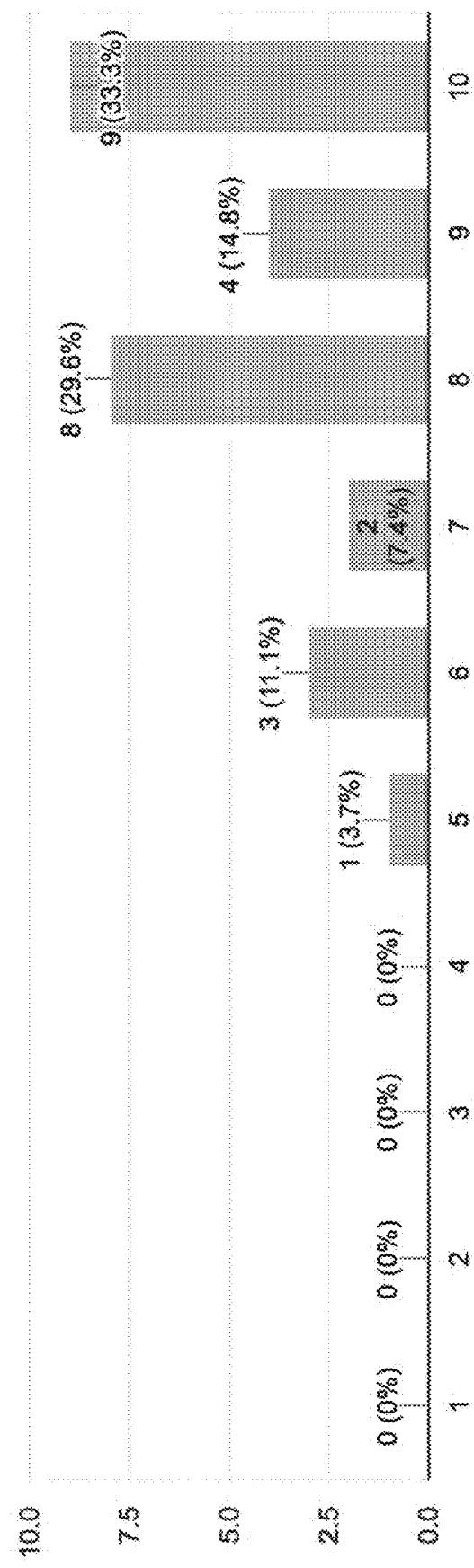
FIG. 21 depicts the effects of sample 2 from Example 1 on sleep length.
Figure 22:
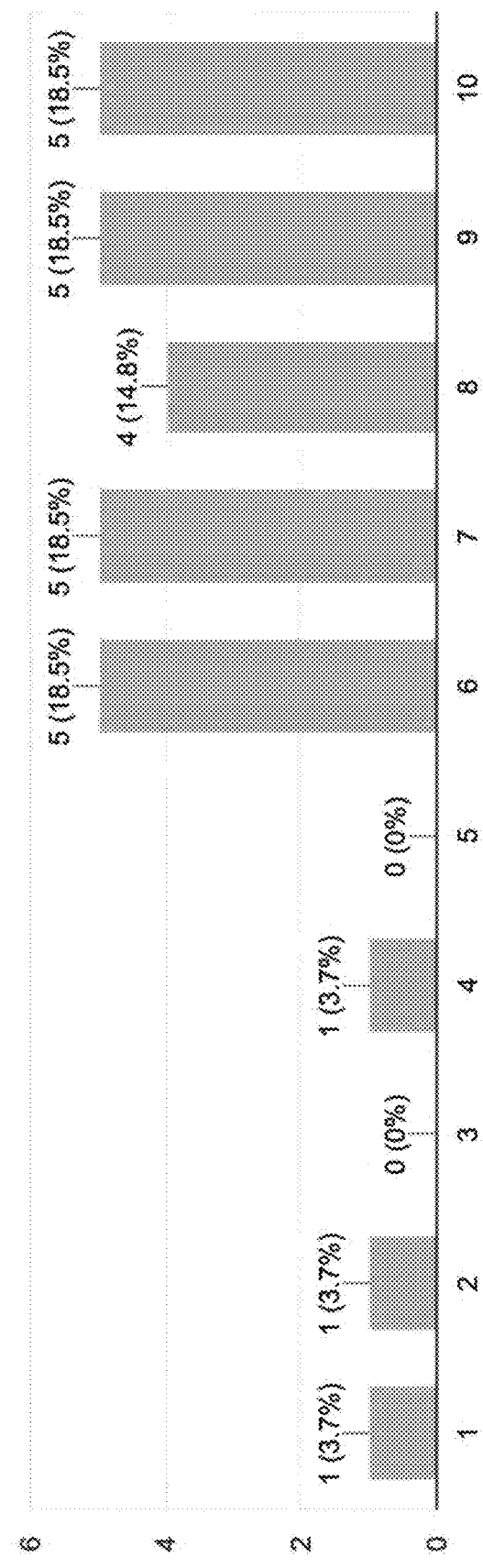
FIG. 22 depicts the effects of sample 2 from Example 1 on sedation.
Figure 23:
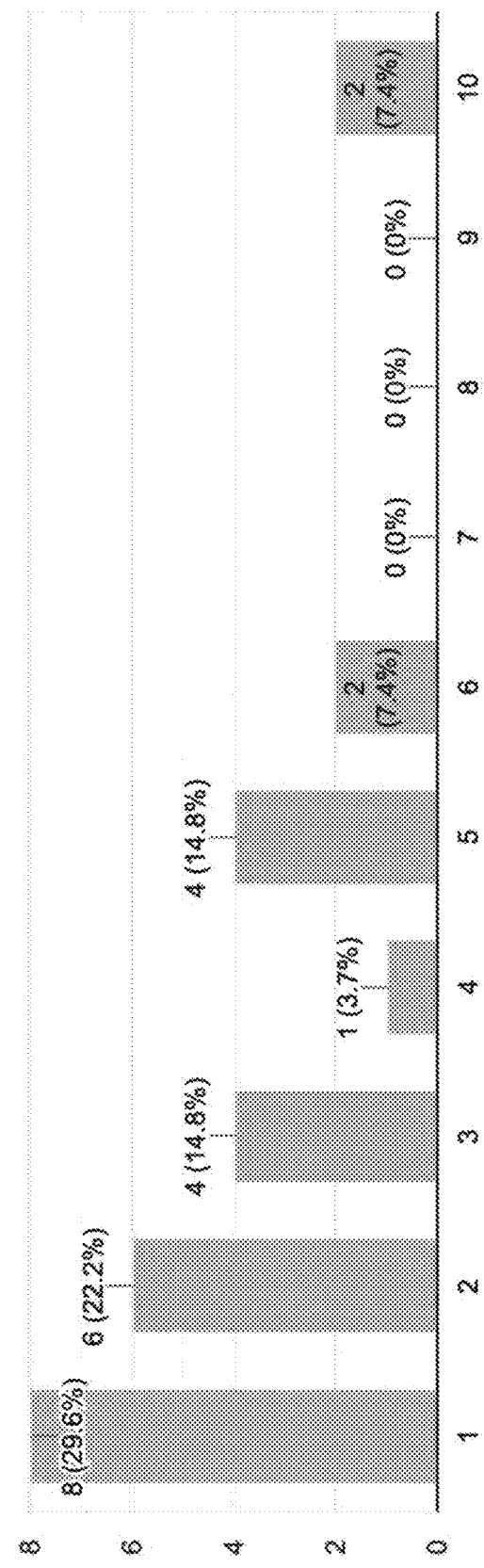
FIG. 23 depicts the effects of sample 2 from Example 1 on morning effects.
Figure 24:
FIG. 24 depicts the effects of sample 2 from Example 1 on sense of calm.
Figure 25:
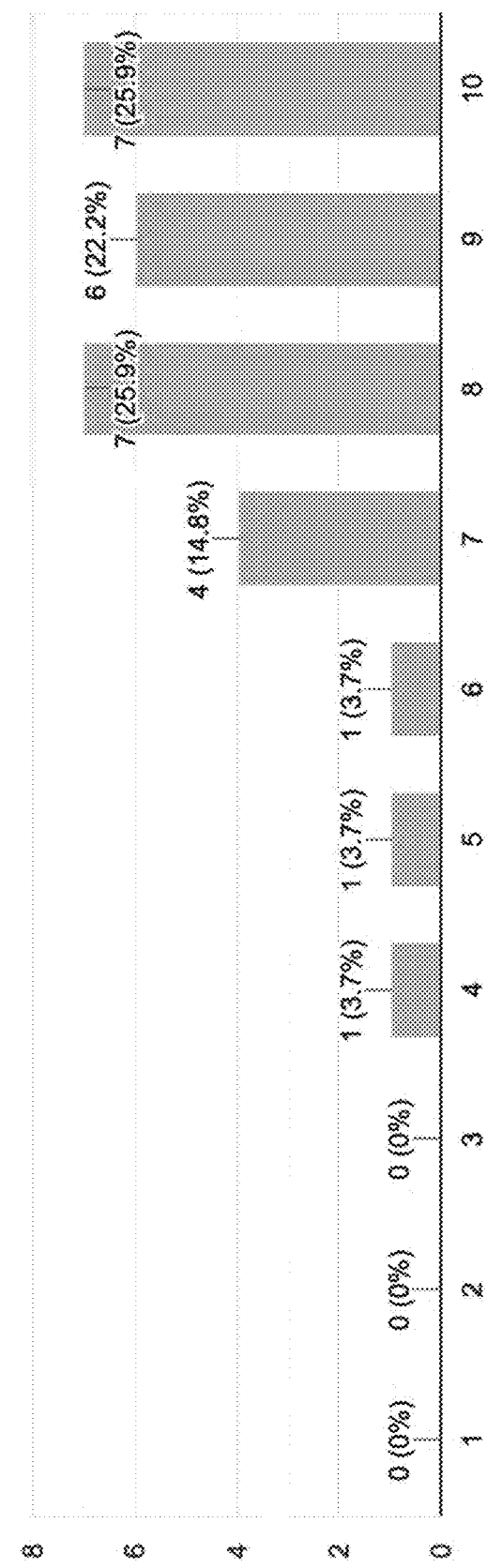
FIG. 25 depicts the effects of sample 2 from Example 1 on ability to relax.
Figure 26:
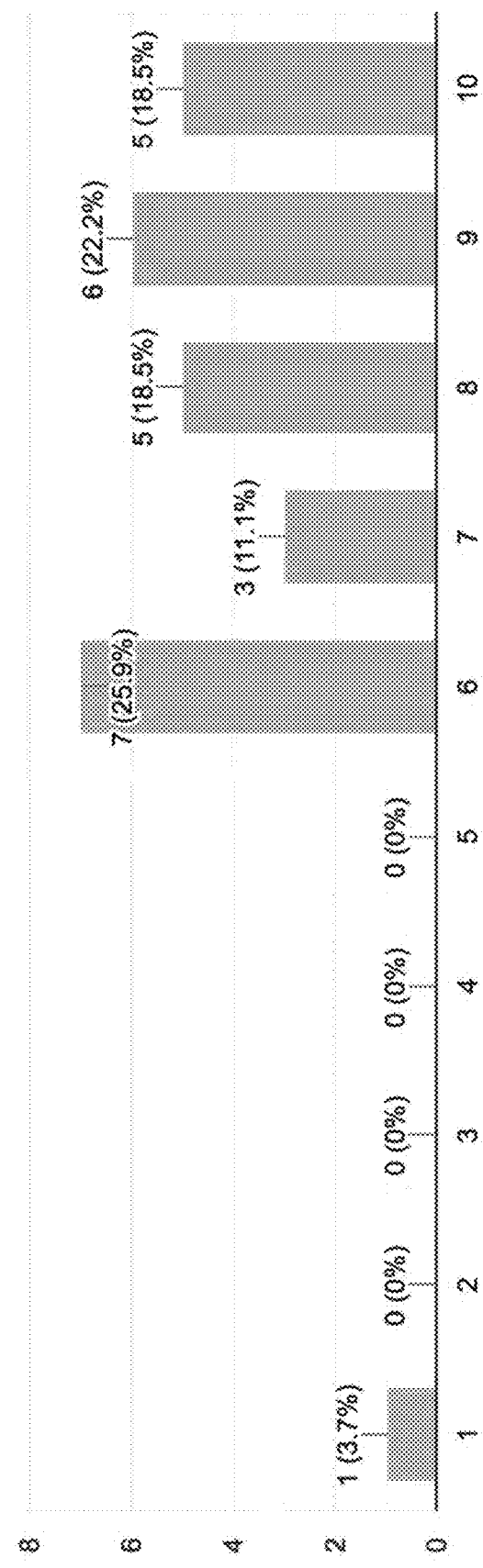
FIG. 26 depicts the effects of sample 2 from Example 1 on sleep physical comfort.
Figure 27:
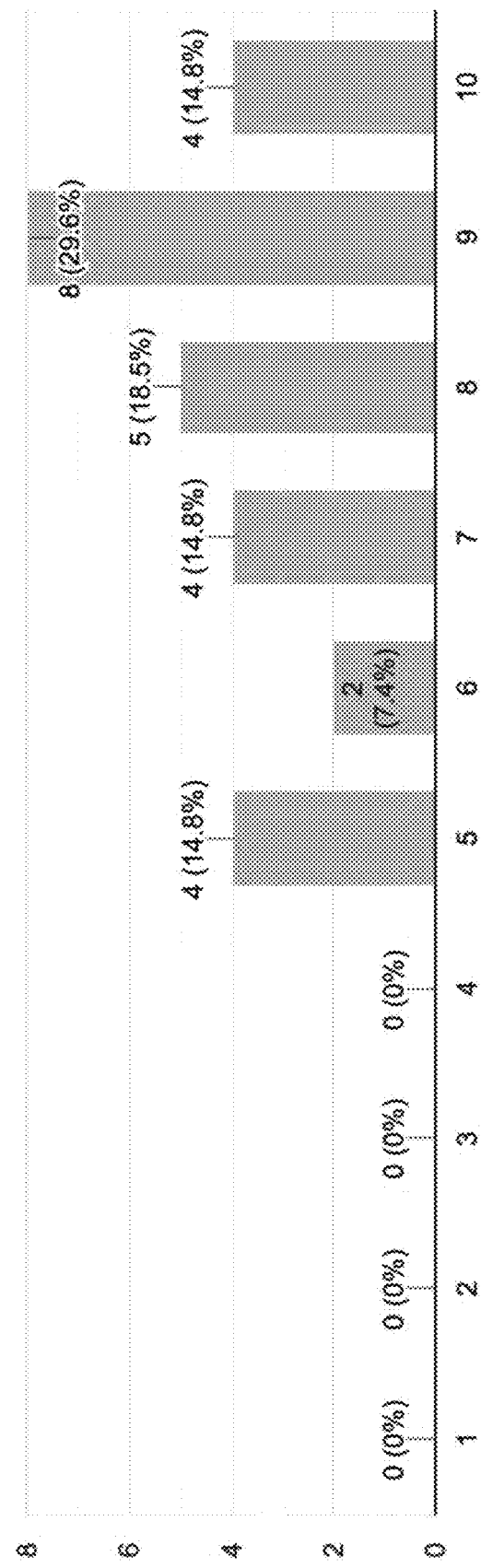
FIG. 27 depicts the effects of sample 2 from Example 1 on emotional comfort.
Figure 28:
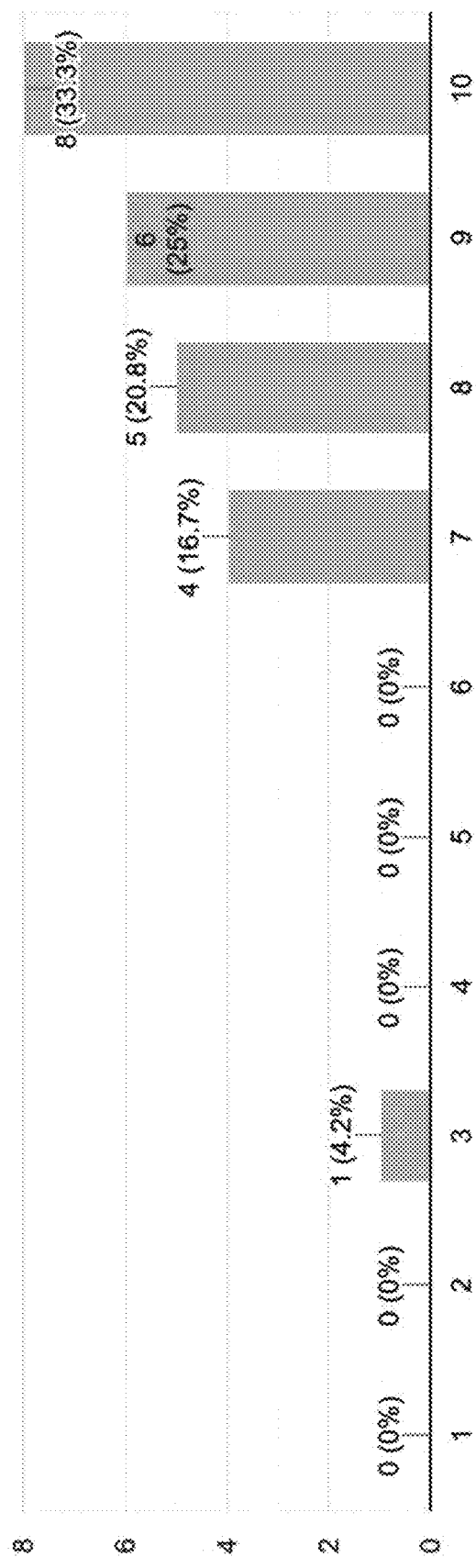
FIG. 28 depicts the effects of sample 4 from Example 1 on falling sleep.
Figure 29:
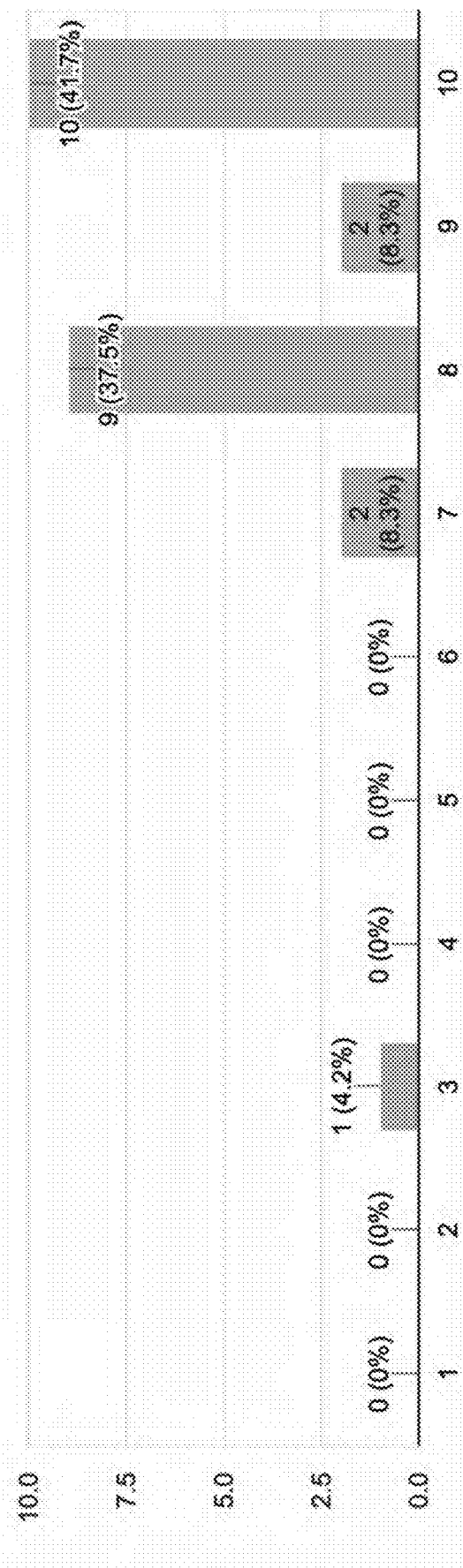
FIG. 29 depicts the effects of sample 4 from Example 1 on sleep quality.
Figure 30:
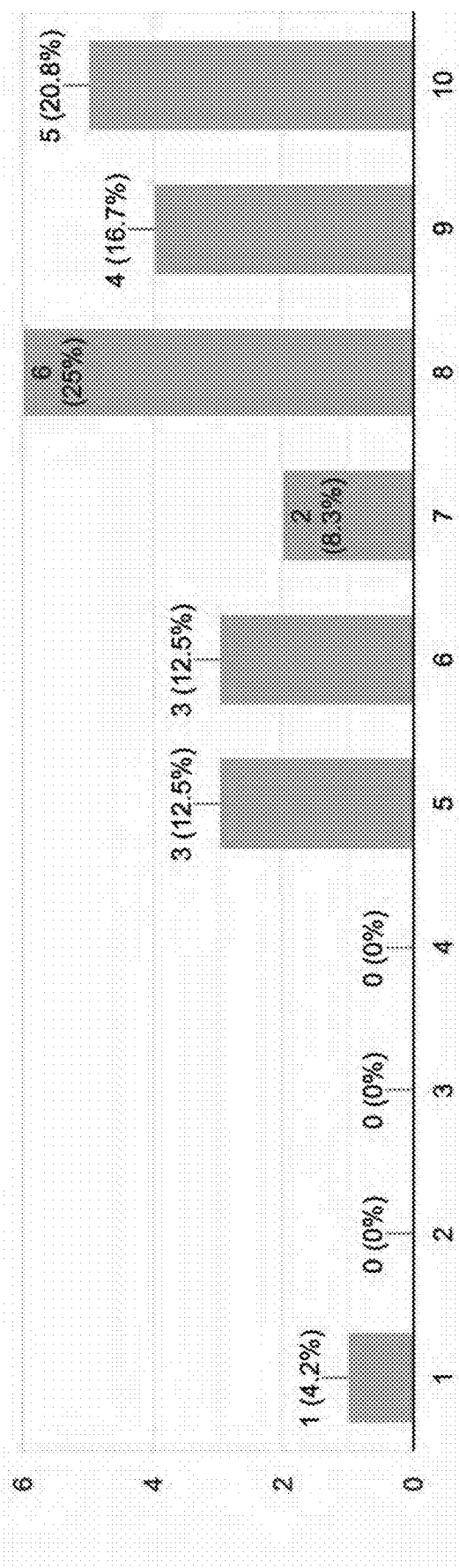
FIG. 30 depicts the effects of sample 4 from Example 1 on sleep length.
Figure 31:
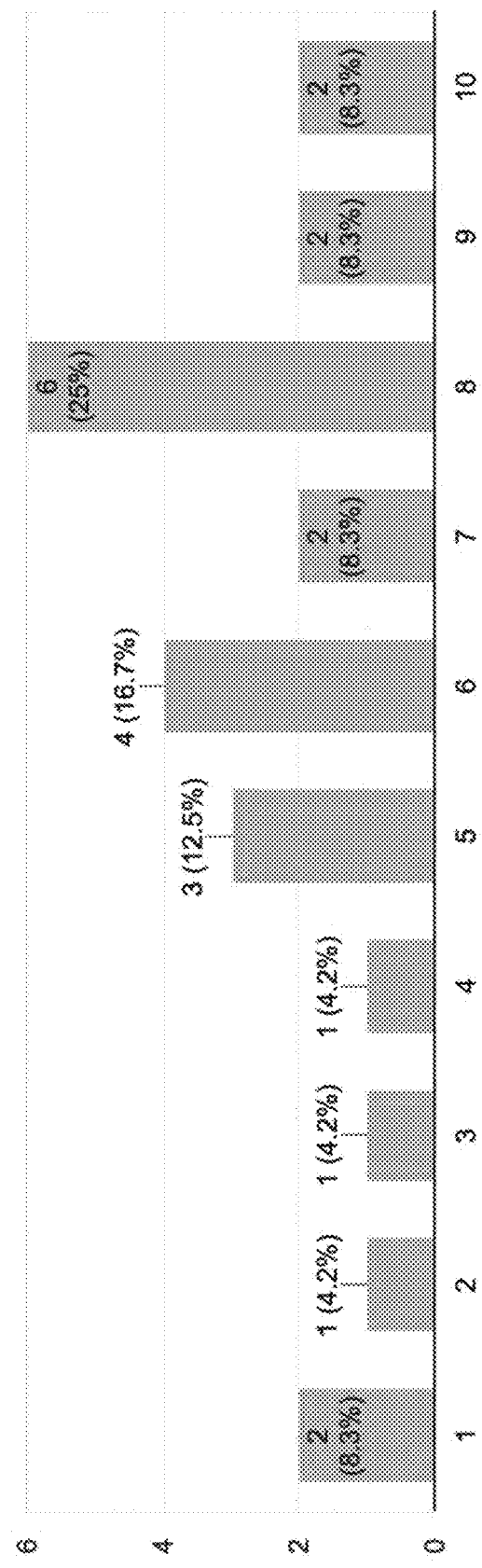
FIG. 31 depicts the effects of sample 4 from Example 1 on sedation.
Figure 32:
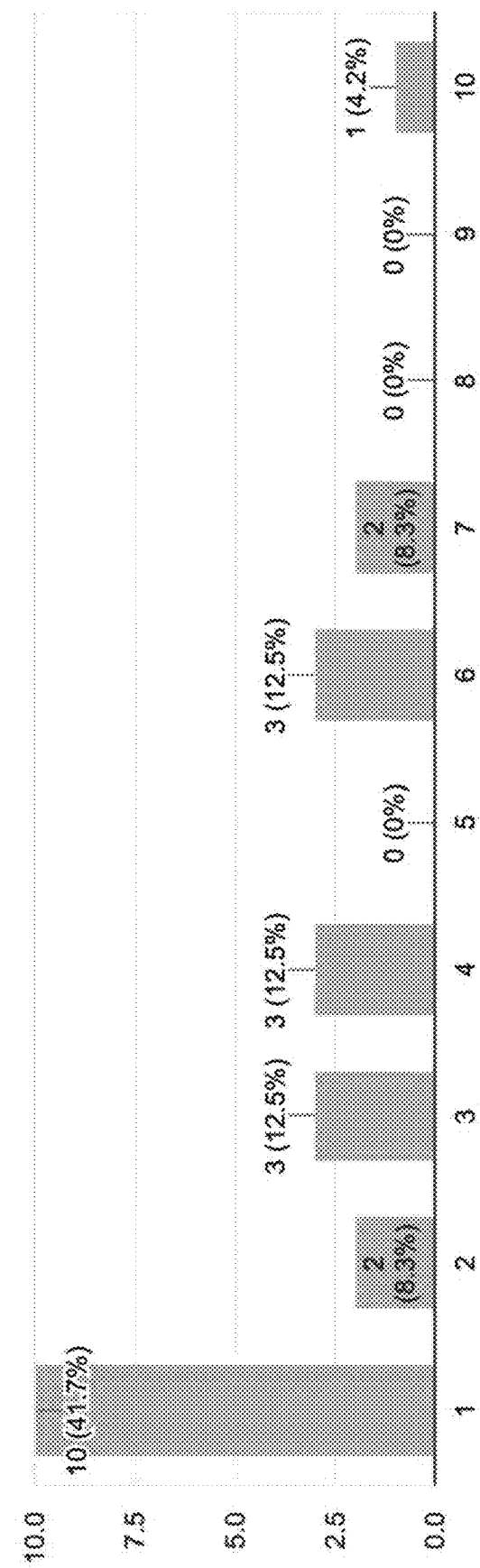
FIG. 32 depicts the effects of sample 4 from Example 1 on morning effects.
Figure 33:
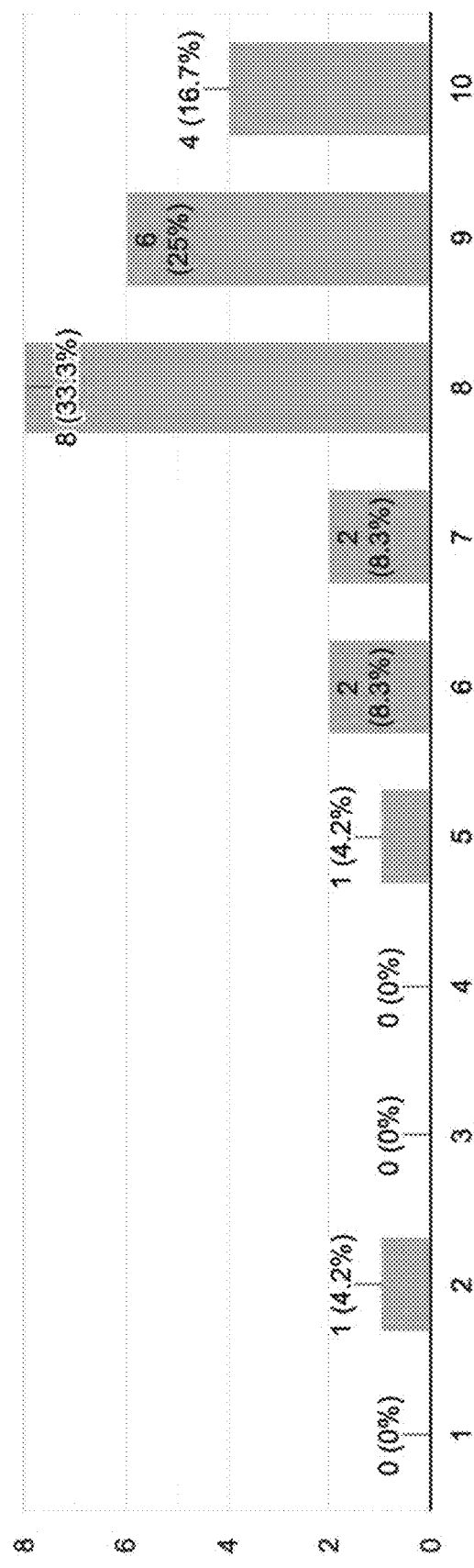
FIG. 33 depicts the effects of sample 4 from Example 1 on sense of calm.
Figure 34:
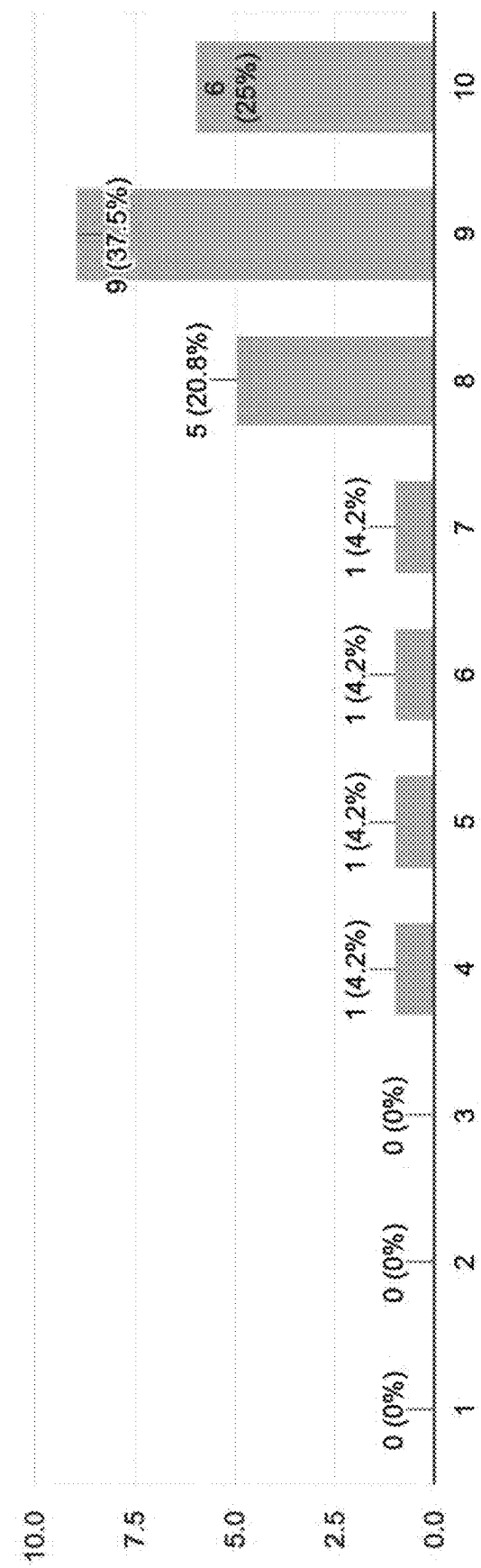
FIG. 34 depicts the effects of sample 4 from Example 1 on ability to relax.
Figure 35:
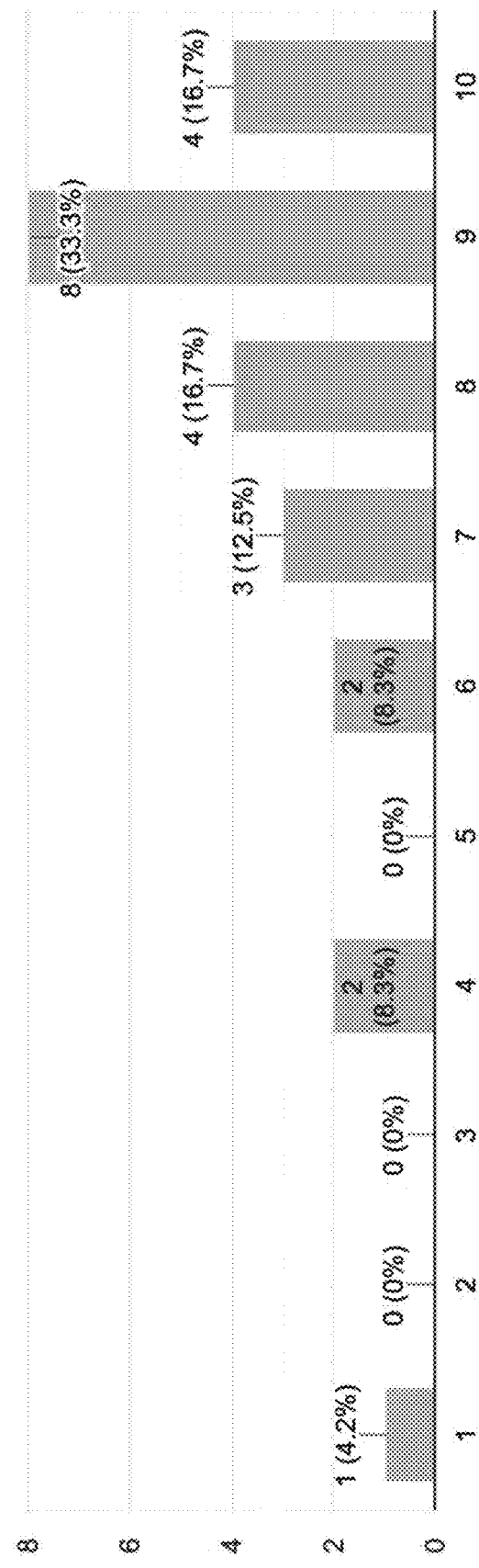
FIG. 35 depicts the effects of sample 4 from Example 1 on sleep physical comfort.
Figure 36:
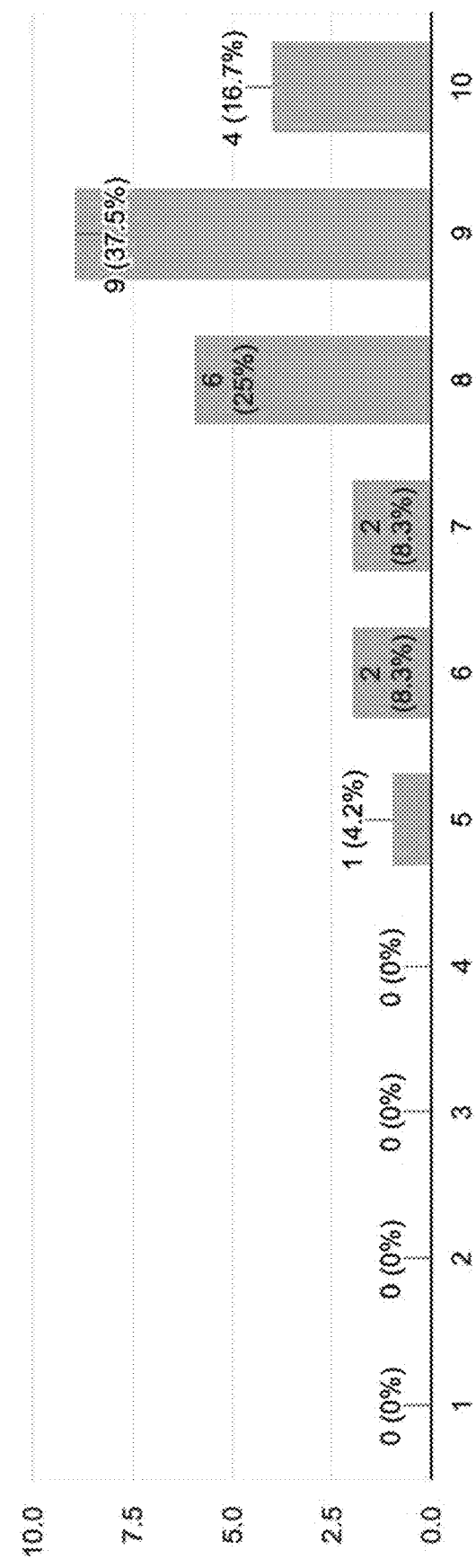
FIG. 36 depicts the effects of sample 4 from Example 1 on emotional comfort.
Figure 37:
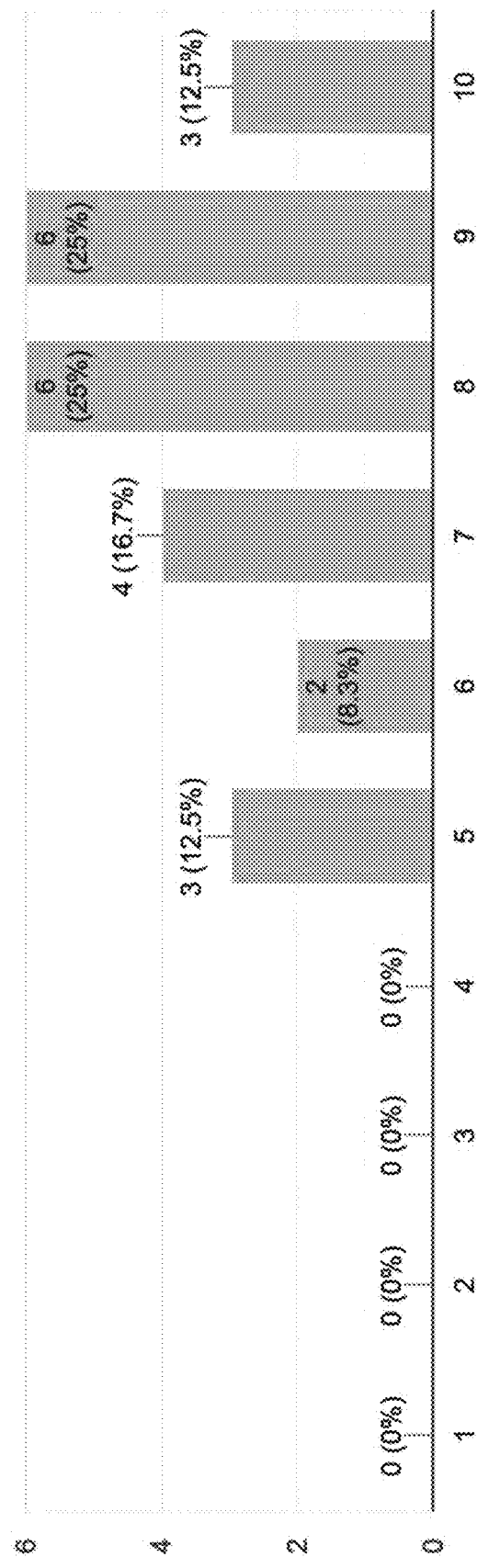
FIG. 37 depicts the effects of sample 4 from Example 1 on well-being

*I. obliquus* is usually found on standing trees and manifests as a large lump of blackened, crusty material on tree bark, which resembles charcoal. FIG. 7 shows a picture of a *I. obliquus* mushroom.

IIIB. Mushroom Extracts

In some embodiments, provided herein are extracts of mushrooms or "mushroom extracts." The term mushroom extract refers to a composition comprising mushrooms or parts thereof. Persons having skill in the art will be familiar with the various methods for creating mushroom extracts. The extract may be created from a whole mushroom or from any part of a mushroom, including but not limited to, the cap, gills, stalk, hyphae, mycelium, gills, spores, volva, partial veil, scales, or combinations thereof. U.S. Pat. No. 7,258,862, issued Aug. 21, 2007, describes the preparation of mushroom extracts and is incorporated by reference herein in its entirety. U.S. Pat. No. 3,033,690 describes a process for creating a mushroom powder and is incorporated by reference herein in its entirety.

In some embodiments, a mushroom extract is produced by grinding/mascerating a mushroom and using ground/mascerated portions of the mushroom. Non-limiting examples of methods to grind mushrooms include using a blender, a food processor, or using a food pulverizer. In some embodiments, mushrooms are sliced prior to grinding. In some embodiments, the ground/mascerated mushroom are fresh mushrooms.

In some embodiments, the mushroom extract is dried mushroom powder. That is, in some embodiments, a mushroom extract is produced by dehydrating a mushroom and subsequently grinding the mushroom to a powder. Dehydration of a mushroom can be performed in a dehydrator. In some embodiments, dehydration occurs at a temperature between about 100° F. and about 150° F., for example, about 100° F., about 105° F., about 110° F., about 115° F., about 120° F., about 125° F., about 130° F., about 135° F., about 140° F., about 145° F., or about 150° F. In some embodiments, after grinding, the mushroom powder is suspended in alcohol, water, or combinations thereof.

In some embodiments, the mushroom extract is a solvent extract. In some embodiments, mushroom extracts are produced from mushrooms using an extraction solvent comprising one or more organic solvents. Non-limiting examples of organic solvents are methanol, ethanol, acetonitrile, ethyl acetate, chloroform, hexane, cyclohexane, isooctane and dichloromethane.

In some embodiments, the mushroom extracts obtained as described above are concentrated. Concentration can be carried out by conventional techniques such as thermal, decompressing thermal, activated carbon or ion exchange resin methods. After concentration, the product is dried by any conventional technique such as air-dry, hot-blast drying, spray dry, and freeze-dry methods. In some embodiments, the liquid is spray dried.

In some embodiments, the mushroom extract is a solvent extract powder. That is, in some embodiments, after extraction with an organic solvent, the organic solvent is removed. In some embodiments, the organic solvent may be removed by distillation or precipitation. In some embodiments, the organic solvent is removed by spray drying.

In some embodiments, the extraction solvent comprises one solvent. In some embodiments, the extraction solvent comprises about 1, 2, 3, 4, 5, 6, 7, 8, 9, or 10 organic solvents. In some embodiments, the extraction solvent comprises water. In some embodiments, the extraction solvent is 70% v/v ethanol and 30% v/v water.

In some embodiments, the solvent is a mixture of two organic solvents. In some embodiments, the extraction solvent comprises methanol and ethyl acetate. In some embodiments, the extraction solvent comprises methanol and chloroform. In some embodiments, the extraction solvent comprises about 11% v/v methanol and about 22% v/v ethyl acetate. In some embodiments, the extraction solvent comprises about 50% v/v methanol and about 33% v/v ethyl acetate. In some embodiments, the extraction solvent comprises 10-60% v/v methanol and 20-40% v/v ethyl acetate. In some embodiments, the extraction solvent comprises about 50% v/v methanol and about 33% v/v chloroform.

IV. Compositions Comprising a Cannabinoid Fraction, a Terpene Fraction, and a Mushroom Extract Fraction In some embodiments, the present disclosure provides compositions comprising one or more cannabinoids (i.e., a Cannabinoid Fraction), one or more terpenes (i.e., a Terpene Fraction), and one or more mushroom extracts (i.e., a Mushroom Extract Fraction).

In some embodiments, the compositions described herein further comprise valerian root (e.g., from *Valeriana officinalis*). Valerian root is an herb that has been used since ancient times to promote tranquility and improve sleep.

In some embodiments, the compositions described herein further comprise caffeine.

In some embodiments, the compositions described herein further comprise guarana (e.g., from *Paullinia cupana*).

In some embodiments, the compositions described herein comprise starch.

In some embodiments, the compositions described herein comprise one or more ingredients selected from the group consisting of hypromellose, microcrystalline cellulose, inositol, and medium-chain triglyceride (MCT) oil. In some embodiments, the compositions described herein comprise hypromellose, microcrystalline cellulose, inositol, and medium-chain triglyceride (MCT) oil.

In some embodiments, the composition comprises Beta-D-glucans.

In some embodiments, the composition comprises a Cannabinoid Fraction to Mushroom Extract Fraction ratio of between about 1:8 and 1:10 by weight, for example, about 1:8, 2:17, 1:9, 2:19, or 1:10 by weight.

In some embodiments, the composition comprises a Cannabinoid Fraction to Mushroom Extract Fraction ratio of about 7:60 by weight.

In some embodiments, the composition comprises a Cannabinoid Fraction to Mushroom Extract Fraction ratio of between about 1:8 and 1:11 by weight, for example, about 1:8, 2:17, 1:9, 2:19, 1:10, 2:21, or 1:11 by weight. In some embodiments, the composition comprises a Cannabinoid Fraction to Mushroom Extract Fraction ratio of about 1:10 by weight.

In some embodiments, the composition comprises a Cannabinoid Fraction to Mushroom Extract Fraction ratio of between about 1:6 and 1:11 by weight, for example, about 1:6, 2:13, 1:7, 2:15, 1:8, 2:17, 1:9, 2:19, 1:10, 2:21, or 1:11 by weight. In some embodiments, the composition comprises a Cannabinoid Fraction to Mushroom Extract Fraction ratio of about 1:8 by weight.

In some embodiments, the composition comprises a Cannabinoid Fraction to Mushroom Extract Fraction ratio of between about 3:1 and 1:1 by weight, for example, about 3:1, 12:5, 2:1, 12:7, 3:2, 4:3, or 1:1 by weight. In some embodiments, the composition comprises a Cannabinoid Fraction to Mushroom Extract Fraction ratio of about 21:10 by weight.

In some embodiments, the composition comprises a Cannabinoid Fraction to Mushroom Extract Fraction ratio of between about 2:1 and 1:2 by weight, for example, about 2:1, 3:2, 1:1, 2:3, 1:1, and 1:2 by weight. In some embodiments, the composition comprises a Cannabinoid Fraction to Mushroom Extract Fraction ratio of about 3:2 by weight.

IVA. Cannabinoid Fraction

In some embodiments, the present disclosure provides compositions comprising a Cannabinoid Fraction. In some embodiments, the Cannabinoid Fraction consists of all the cannabinoids in the composition (i.e. the compositions of the present disclosure). A cannabinoid is part of a Cannabinoid Fraction, if it is present at detectable levels (e.g., by HPLC or Gas-Chromatography).

Cannabinoid Fractions may be discussed in binary terms that simply indicate which cannabinoids are present. Cannabinoid Fractions may also indicate the individual contents of each cannabinoid, for example, by indicating the relative content of a cannabinoid compared to other cannabinoids (e.g., by weight or by moles) in the Cannabinoid Fraction. For example, the relative content of CBD in a Cannabinoid Fraction containing 5 mg of THC and 5 mg of CBD is 50% CBD by weight of the Cannabinoid Fraction. As another example, the relative content of CBD in a Cannabinoid Fraction containing 3 mol of CBD and 7 mol of THC is 30% CBD mol/mol. In some embodiments, the relative content (e.g., weight or moles) of a cannabinoid compared to another cannabinoid is expressed as a ratio of the amount of one cannabinoid to the amount of another cannabinoid. For example, a Cannabinoid Fraction containing 5 mg of CBD and 5 mg of THC has a CBD:THC ratio of 1:1 by weight.

Cannabinoid Fractions may also indicate the content of a cannabinoid in absolute terms. For example, one may refer to the Cannabinoid Fraction as having 5 mg CBD and 5 mg THC.

Cannabinoid Fractions may also indicate the content of a cannabinoid in relation to the weight of the entire composition. For example, a 100 mg composition having 5 mg CBD has 5% w/w CBD within the total composition.

In some embodiments, the Cannabinoid Fraction comprises one or more cannabinoids selected from the group consisting of cannabidiol (CBD), cannabigerol (CBG), cannabinol (CBN), and tetrahydrocannabinol (THC). In some embodiment, the Cannabinoid Fraction comprises two or more cannabinoids selected from the group consisting of cannabidiol (CBD), cannabigerol (CBG), cannabinol (CBN), and tetrahydrocannabinol (THC). In some embodiment, the Cannabinoid Fraction comprises three or more cannabinoids selected from the group consisting of cannabidiol (CBD), cannabigerol (CBG), cannabinol (CBN), and tetrahydrocannabinol (THC). In some embodiment, the Cannabinoid Fraction comprises cannabidiol (CBD), cannabigerol (CBG), cannabinol (CBN), and tetrahydrocannabinol (THC).

In some embodiments, the Cannabinoid Fraction comprises CBD and CBG. In some embodiments, the Cannabinoid Fraction comprises a CBD:CBG ratio of between about 4:1 and 1:4 by weight, including all ratios in between. In some embodiments, the Cannabinoid Fraction comprises a CBD:CBG ratio of between about 2:1 and 1:2 by weight, including all ratios in between, for example, 2:1, 1.5:1, 4:3, 3:4, 1:1, and 1:2. In some embodiments, the Cannabinoid Fraction comprises a CBD:CBG ratio of about 3:4. In some embodiments, the Cannabinoid Fraction comprises between about 30-50% CBD and 40-70% CBG by weight, for example, about 30%, about 35%, about 40%, about 45%, or about 50% CBD by weight, and about 40%, about 45%, about 50%, about 55%, about 60%, about 65%, or about 70% CBG by weight.

In some embodiments, the Cannabinoid Fraction comprises CBN and CBD. In some embodiments, the Cannabinoid Fraction comprises a CBN:CBD ratio of between about 4:1 and 1:4 by weight, including all ratios in between. In some embodiments, the Cannabinoid Fraction comprises a CBN:CBD ratio of between about 2:1 and 1:2 by weight, including all ratios in between, for example, 2:1, 1.5:1, 4:3, 3:4, 1:1, and 1:2. In some embodiments, the Cannabinoid Fraction comprises a CBN:CBD ratio of about 2:3. In some embodiments, the Cannabinoid Fraction comprises between about 30-40% CBD and 60-70% CBG by weight, for example, about 30%, about 35%, or about 40% CBD by weight and about 60%, about 65%, or about 70% CBG by weight.

In some embodiments, the Cannabinoid Fraction comprises THC. In some embodiments, the Cannabinoid Fraction comprises about 100% THC by weight.

In some embodiments, the Cannabinoid Fraction comprises THC and CBN. In some embodiments, the Cannabinoid Fraction comprises a THC:CBN ratio of between about 6:1 and 2:1 by weight, including all ratios in between, for example, 6:1, 5:1, 4:1, 3:1, 2:1, and 1:2. In some embodiments, the Cannabinoid Fraction comprises a THC:CBN ratio of about 4:1. In some embodiments, the Cannabinoid Fraction comprises between about 70-90% THC and 10-30% CBN by weight, for example, about 70%, about 75%, about 80%, about 85%, or about 90% THC by weight and about 10%, about 15%, about 20%, about 25%, or about 30% CBN by weight.

IVB. Mushroom Extract Fraction

In some embodiments, the present disclosure provides compositions comprising one or more mushroom extracts (e.g., a Mushroom Extract Fraction). A Mushroom Extract Fraction consists of all the mushroom extracts in a composition (e.g., the compositions of the present disclosure).

Mushroom Extract Fractions may be discussed in binary terms that simply indicate which cannabinoids are present. Mushroom Extract Fractions may also indicate the individual contents of each mushroom extract, for example, by indicating the relative content of a mushroom extract compared to other mushroom extracts (e.g., by weight) in the Mushroom Extract Fraction. For example, the relative content of *Cordyceps militaris* in a Mushroom Extract Fraction containing 5 mg of *Cordyceps militaris* and 5 mg of *Trametes versicolor* is 50% *Cordyceps militaris* w/w. In some embodiments, the relative content (e.g., weight) of a mushroom extract compared to other mushroom extracts is expressed as a ratio of the weight of one mushroom extract to the weight of another mushroom extract. For example, a Mushroom Extract Fraction containing 5 mg of *Cordyceps militaris* and 5 mg of *Trametes versicolor* has a *Cordyceps militaris*:*Trametes versicolor* ratio of 1:1 by weight. In some embodiments, the relative content (e.g., weight) of a mushroom extract compared to one or more mushroom extracts is expressed as a percentage by amount (e.g. by weight) of the Mushroom Extract Fraction. For example, a Mushroom Extract Fraction containing 5 mg of *Cordyceps militaris* and 5 mg of *Trametes versicolor* contains 50% *Cordyceps militaris* and 50% *Trametes versicolor* by weight of the Mushroom Extract Fraction.

Mushroom Extract Fractions may also indicate the content of a mushroom extract in absolute terms. For example, one may refer to the Mushroom Extract Fractions as having 5 mg of *Cordyceps militaris* and 5 mg of *Trametes versicolor*.

Mushroom Extract Fractions may also indicate the content of a mushroom extract in relation to the weight of the entire composition. For example, a 100 mg composition having 5 mg *Cordyceps militaris* has 5% w/w *Cordyceps militaris* within the total composition.

In some embodiments, the Mushroom Extract Fraction comprises at least one mushroom extract selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises at least two mushroom extracts selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises at least three mushroom extracts selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises at least four mushroom extracts selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises at least five mushroom extracts selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises at least six mushroom extracts selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises seven mushroom extracts selected from the group consisting of *Hericium ernaceus, Cordyceps militaris, Trametes versicolor, Ganoderma lingzhi, Grifola frondosa, Lentinula edodes*, and *Inonotus obliquus*.

In some embodiments, the Mushroom Extract Fraction comprises *Hericium ernaceus* and *Cordyceps militaris*.

In some embodiments, the Mushroom Extract Fraction comprises a *Hericium ernaceus:Cordyceps militaris* ratio between 2:1 and 1:2 by weight.

In some embodiments, the Mushroom Extract Fraction comprises a *Hericium ernaceus:Cordyceps militaris* ratio of about 1:1 by weight.

In some embodiments, the Mushroom Extract Fraction comprises between about 40-60% *Hericium ernaceus* and about 40-60% *Cordyceps militaris* by weight of the Mushroom Extract Fraction.

In some embodiments, the Mushroom Extract Fraction comprises between about 40-60% *Hericium ernaceus*, for example, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% by weight of the Mushroom Extract Fraction.

In some embodiments, the Mushroom Extract Fraction comprises between about 40-60% *Cordyceps militaris*, for example, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% by weight of the Mushroom Extract Fraction.

In some embodiments, the Mushroom Extract Fraction comprises *Trametes versicolor, Ganoderma lingzhi, Grifola frondosa, Lentinula edodes*, and *Inonotus obliquus*.

In some embodiments, the Mushroom Extract Fraction comprises about equal parts of *Trametes versicolor, Ganoderma lingzhi, Grifola frondosa, Lentinula edodes*, and *Inonotus obliquus* by weight.

In some embodiments, the Mushroom Extract Fraction comprises between about 10-30% *Trametes versicolor*, between about 10-30% *Ganoderma lingzhi*, between about 10-30% *Grifola frondosa*, between about 10-30% *Lentinula edodes*, and between about 10-30% *Inonotus obliquus* by weight of the Mushroom Extract Fraction.

In some embodiments, the Mushroom Extract Fraction comprises between about 10-30% *Trametes versicolor*, for example, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight of the Mushroom Extract Fraction.

In some embodiments, the Mushroom Extract Fraction comprises between about 10-30% *Ganoderma lingzhi*, for example, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight of the Mushroom Extract Fraction.

In some embodiments, the Mushroom Extract Fraction comprises between about 10-30% *Grifola frondosa*, for example, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight of the Mushroom Extract Fraction.

In some embodiments, the Mushroom Extract Fraction comprises between about 10-30% *Lentinula edodes*, for example, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight of the Mushroom Extract Fraction.

In some embodiments, the Mushroom Extract Fraction comprises between about 10-30% *Inonotus obliquus*, for example, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight of the Mushroom Extract Fraction.

In some embodiments, the Mushroom Extract Fraction comprises triterpenes. Non-limiting examples of triterpenes include ergosterol peroxide; cerevisterol; 3β,5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3, 23-trihydroxy-urs-12-en-28-oic acid); ganoderic acid A; and Lanostanes.

IVC. Terpene Fraction

In some embodiments, the present disclosure provides compositions comprising one or more terpenes (e.g., a Terpene Fraction). A Terpene Fraction consists of all the terpenes in a composition (e.g., the compositions of the present disclosure). A terpene is part of a Terpene Fraction, if it is present at detectable levels (e.g., by HPLC or Gas-Chromatography).

Terpene Fractions may be discussed in binary terms that simply indicate which terpenes are present. Terpene Fractions may also indicate the individual contents of each terpene, for example, by indicating the relative content of a terpene (e.g., by weight or by molar) compared to other terpenes in the Terpene Fraction. For example, the relative content of alpha pinene in a Terpene Fraction containing 5 mg of limonene and 5 mg of alpha pinene is 50% w/w alpha pinene. As another example, the relative content of alpha pinene in a Terpene Fraction containing 3 mol of alpha pinene and 7 mol of limonene is 30% alpha pinene mol/mol. In some embodiments, the relative content (e.g., weight or moles) of a terpene compared to another terpene is expressed as a ratio of the amount of one terpene to the amount of another terpene. For example, a Terpene Fraction containing 5 mg of alpha pinene and 5 mg of limonene has an alpha pinene:limonene ratio of 1:1 by weight.

Terpene Fractions may also indicate the content of a terpene in absolute terms. For example, one may refer to the Terpene fraction as having 5 mg alpha pinene and 5 mg limonene.

Terpene Fractions may also indicate the content of a terpene in relation to the weight of the entire composition. For example, a 100 mg composition having 5 mg alpha pinene has 5% w/w alpha pinene within the total composition.

The Terpene fractions provided herein are selected to provide a synergistic effect with the Mushroom extract fractions of the compositions described herein.

In some embodiments, the Terpene Fraction comprises one or more terpenes selected from the group consisting of alpha pinene, limonene, beta-pinene, alpha phellandrene, terpinolene, nerolidol, nerol, myrcene, and beta caryophyllene. In some embodiments, the Terpene Fraction comprises one or more terpenes selected from the group consisting of alpha pinene, limonene, beta-pinene, alpha phellandrene, terpinolene, nerolidol, and nerol. In some embodiments, the Terpene Fraction comprises two or more terpenes selected from the group consisting of alpha pinene, limonene, beta-pinene, alpha phellandrene, terpinolene, nerolidol, and nerol. In some embodiments, the Terpene Fraction comprises three or more terpenes selected from the group consisting of alpha pinene, limonene, beta-pinene, alpha phellandrene, terpinolene, nerolidol, and nerol. In some embodiments, the Terpene Fraction comprises four or more terpenes selected from the group consisting of alpha pinene, limonene, beta-pinene, alpha phellandrene, terpinolene, nerolidol, and nerol. In some embodiments, the Terpene Fraction comprises five or more terpenes selected from the group consisting of alpha pinene, limonene, beta-pinene, alpha phellandrene, terpinolene, nerolidol, and nerol. In some embodiments, the Terpene Fraction comprises six or more terpenes selected from the group consisting of alpha pinene, limonene, bet-pinene, alpha phellandrene, terpinolene, nerolidol, and nerol. In some embodiments, the Terpene Fraction comprises alpha pinene, limonene, beta-pinene, alpha phellandrene, terpinolene, nerolidol, and nerol.

In some embodiments, the Terpene Fraction comprises at least two terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises at least three terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises at least four terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises at least five terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises at least six terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises at least seven terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises at least eight terpenes selected from the group consisting of: alpha pinene, limonene, beta-pinene, alpha phellandrene, terpinolene, nerolidol, nerol, myrcene, and beta caryophyllene.

In some embodiments, the Terpene Fraction comprises alpha pinene, limonene, beta-pinene, alpha phellandrene, terpinolene, nerolidol, nerol, myrcene, and beta caryophyllene.

In some embodiments, the Terpene Fraction comprises alpha pinene, limonene, beta-pinene, alpha phellandrene, terpinolene, nerolidol, and nerol.

In some embodiments, the Terpene Fraction comprise between about 0.1% and about 99% alpha pinene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% alpha pinene by weight of the Terpene Fraction, including all ranges and subranges therebetween.

In some embodiments, the Terpene Fraction comprise between about 0.1% and about 99% limonene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about Δ8%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% limonene by weight of the Terpene Fraction, including all ranges and subranges therebetween.

In some embodiments, the Terpene Fraction comprise between about 0.1% and about 99% beta-pinene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% beta-pinene by weight of the Terpene Fraction, including all ranges and subranges therebetween.

In some embodiments, the Terpene Fraction comprise between about 0.1% and about 99% alpha phellandrene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% alpha phellandrene by weight of the Terpene Fraction, including all ranges and subranges therebetween.

In some embodiments, the Terpene Fraction comprise between about 0.1% and about 99% terpinolene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% terpinolene by weight of the Terpene Fraction, including all ranges and subranges therebetween.

In some embodiments, the Terpene Fraction comprise between about 0.1% and about 99% nerolidol by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% nerolidol by weight of the Terpene Fraction, including all ranges and subranges therebetween.

In some embodiments, the Terpene Fraction comprise between about 0.1% and about 99% nerol by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% nerol by weight of the Terpene Fraction, including all ranges and subranges therebetween.

In some embodiments, the Terpene Fraction comprise between about 0.1% and about 99% myrcene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% myrcene by weight of the Terpene Fraction, including all ranges and subranges therebetween.

In some embodiments, the Terpene Fraction comprise between about 0.1% and about 99% beta caryophyllene by weight, for example, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 51%, about 52%, about 53%, about 54%, about 55%, about 56%, about 57%, about 58%, about 59%, about 61%, about 62%, about 63%, about 64%, about 65%, about 66%, about 67%, about 68%, about 69%, about 71%, about 72%, about 73%, about 74%, about 75%, about 76%, about 77%, about 78%, about 79%, about 81%, about 82%, about 83%, about 84%, about 85%, about 86%, about 87%, about 88%, about 89%, about 91%, about 92%, about 93%, about 94%, about 95%, about 96%, about 97%, about 98%, or about 99% beta caryophyllene by weight of the Terpene Fraction, including all ranges and subranges therebetween.

V. Exemplary Compositions of the Disclosure

Provided below are non-limiting examples of compositions comprising a cannabinoid profile, a mushroom extract profile, and a terpene profile. In some embodiments, the composition is selected from Table 1, Table 2, Table 3, or Table 4.

TABLE 1

| Composition | Mushroom Extract Fraction | Cannabinoid Extract Fraction | Terpene Extract Fraction | Additional Ingredients |
|---|---|---|---|---|
| 1 | 150 mg Hericium ernaceus 150 mg Cordyceps militaris; | 15 mg CBD 20 mg CBG | alpha pinene, limonene, beta-pinene, alpha phellandrene, terpinolene, nerolidol, and nerol | |
| 2 | 60 mg Trametes versicolor, 60 mg Ganoderma linggzhi, 60 mg Grifola frondosa, 60 mg Lentinula edodes, 60 mg Inonotus obliquus | 10 mg CBN 15 mg CBD | alpha pinene, limonene, beta-pinene, alpha phellandrene, terpinolene, nerolidol, and nerol | |
| 3 | 50 mg Hericium ernaceus, 50 mg Cordyceps militaris | 10 mg THC | alpha pinene, limonene, beta-pinene, alpha phellandrene, terpinolene, nerolidol, and nerol | |
| 4 | 20 mg Trametes versicolor, 20 mg Ganoderma linggzhi, 20 mg Grifola frondosa, 20 mg Lentinula edodes, 20 mg Inonotus obliquus; | 10 mg THC; 2.5 mg CBN; | alpha pinene, limonene, beta-pinene, alpha phellandrene, terpinolene, nerolidol, and nerol | |
| 5 | 250 mg Hericium ernaceus; 250 mg Cordyceps militaris | 450 mg CBD; 600 mg CBG; | alpha pinene, limonene, beta-pinene, alpha phellandrene, terpinolene, nerolidol, and nerol. | |
| 6 | 100 mg Trametes versicolor, 100 mg Ganoderma linggzhi, 100 mg Grifola frondosa, 100 mg Lentinula edodes, 100 mg Inonotus obliquus | 300 mg CBN 450 mg CBD; | alpha pinene, limonene, beta-pinene, alpha phellandrene, terpinolene, nerolidol, and nerol | |
| 7 | 150 mg Hericium ernaceus 150 mg Cordyceps militaris; | 15 mg CBD; 20 mg CBG; | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, guarana |

TABLE 1-continued

| Composition | Mushroom Extract Fraction | Cannabinoid Extract Fraction | Terpene Extract Fraction | Additional Ingredients |
|---|---|---|---|---|
| 8 | 60 mg Trametes versicolor, 60 mg Ganoderma linggzhi, 60 mg Grifola frondosa, 60 mg Lentinula edodes, 60 mg Inonotus obliquus | 10 mg CBN 15 mg CBD | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, valerian root |
| 9 | 50 mg Hericium ernaceus; 50 mg Cordyceps militaris | 10 mg THC | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, guarana. |
| 10 | 20 mg Trametes versicolor, 20 mg Ganoderma linggzhi, 20 mg Grifola frondosa, 20 mg Lentinula edodes, 20 mg Inonotus obliquus; | 10 mg THC 2.5 mg CBN | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, guarana. |
| 11 | 250 mg Hericium ernaceus, 250 mg Cordyceps militaris | 450 mg CBD 600 mg CBG | alpha pinene, limonene, beta-pinene, alpha phellandrene, terpinolene, nerolidol, and nerol. | MCT oil, beta-D-glucans |
| 12 | 100 mg Trametes versicolor, 100 mg Ganoderma linggzhi, 100 mg Grifola frondosa, 100 mg Lentinula edodes, 100 mg Inonotus obliquus | 300 mg CBN 450 mg CBD; | alpha pinene, limonene, beta-pinene, alpha phellandrene, terpinolene, nerolidol, and nerol | MCT oil, beta-D-glucans |

TABLE 2

| Composition | Mushroom Extract Fraction | Cannabinoid Extract Fraction | Terpene Extract Fraction | Additional Ingredients |
|---|---|---|---|---|
| 13 | 100-200 mg Hericium ernaceus 100-200 mg Cordyceps militaris; | 10-20 mg CBD 10-30 mg CBG | alpha pinene, limonene, beta-pinene, alpha phellandrene, terpinolene, nerolidol, and nerol | |
| 14 | 50-70 mg Trametes versicolor, 50-70 mg Ganoderma linggzhi, 50-70 mg Grifola frondosa, 50-70 mg Lentinula edodes, 50-70 mg Inonotus obliquus | 5-15 mg CBN 10-20 mg CBD | alpha pinene, limonene, beta-pinene, alpha phellandrene, terpinolene, nerolidol, and nerol | |
| 15 | 40-60 mg Hericium ernaceus; 40-60 mg Cordyceps militaris | 5-15 mg THC | alpha pinene, limonene, beta-pinene, alpha phellandrene, terpinolene, nerolidol, and nerol | |
| 16 | 10-30 mg Trametes versicolor, 10-30 mg Ganoderma linggzhi, 10-30 mg Grifola frondosa, 10-30 mg Lentinula edodes, 10-30 mg Inonotus obliquus; | 5-15 mg THC 1-5 mg CBN; | alpha pinene, limonene, beta-pinene, alpha phellandrene, terpinolene, nerolidol, and nerol | |
| 17 | 250 mg Hericium ernaceus, 250 mg Cordyceps militaris | 400-500 mg CBD; 500-700 mg CBG; | alpha pinene, limonene, beta-pinene, alpha phellandrene, terpinolene, nerolidol, and nerol. | |
| 18 | 50-150 mg Trametes versicolor, 50-150 mg Ganoderma linggzhi 50-150 mg Grifola frondosa, 50-150 mg Lentinula edodes, 50-150 mg Inonotus obliquus | 200-400 mg CBN 350-550 mg CBD; | alpha pinene, limonene, beta-pinene, alpha phellandrene, terpinolene, nerolidol, and nerol | |
| 19 | 100-200 mg Hericium ernaceus 100-200 mg Cordyceps militaris; | 10-20 mg CBD 10-30 mg CBG; | alpha pinene, limonene, beta-pinene, alpha phellandrene, terpinolene, nerolidol, and nerol | Hypromellose, microcrystalline cellulose, pure inositol, MCT oil, organic tapioca starch |
| 20 | 50-70 mg Trametes | 5-15 mg CBN 10-20 mg CBD | alpha pinene, limonene, beta- | Hypromellose, microcrystalline |

TABLE 2-continued

| Composition | Mushroom Extract Fraction | Cannabinoid Extract Fraction | Terpene Extract Fraction | Additional Ingredients |
|---|---|---|---|---|
| | versicolor, 50-70 mg Ganoderma linggzhi, 50-70 mg Grifola frondosa, 50-70 mg Lentinula edodes, 50-70 mg Inonotus obliquus | | pinene, alpha phellandrene, terpinolene, nerolidol, and nerol | cellulose, pure inositol, MCT oil, organic tapioca starch. |
| 21 | 40-60 mg Hericium ernaceus; 40-60 mg Cordyceps militaris | 5-15 mg THC | alpha pinene, limonene, beta-pinene, alpha phellandrene, terpinolene, nerolidol, and nerol | Hypromellose, microcrystalline cellulose, pure inositol, MCT oil, organic tapioca starch. |
| 22 | 10-30 mg Trametes versicolor, 10-30 mg Ganoderma linggzhi, 10-30 mg Grifola frondosa, 10-30 mg Lentinula edodes, 10-30 mg Inonotus obliquus; | 5-15 mg THC 1-5 mg CBN | alpha pinene, limonene, beta-pinene, alpha terpinolene, nerolidol, and nerol | Hypromellose, microcrystalline cellulose, pure inositol, MCT phellandrene, tapioca starch. |
| 23 | 150-350 mg Hericium ernaceus; 150-350 mg Cordyceps militaris | 400-500 mg CBD; 500-700 mg CBG; | alpha pinene, limonene, beta-pinene, alpha phellandrene, terpinolene, nerolidol, and nerol. | MCT oil |
| 24 | 50-150 mg Trametes versicolor, 50-150 mg Ganoderma linggzhi, 50-150 mg Grifola frondosa, 50-150 mg Lentinula edodes, 50-150 mg Inonotus obliquus | 200-400 mg CBN 350-550 mg CBD | alpha pinene, limonene, beta-pinene, alpha phellandrene, terpinolene, nerolidol, and nerol | MCT oil |

TABLE 3

| Composition | Mushroom Extract Fraction (by weight) | Cannabinoid Extract Fraction (by weight) | Terpene Extract Fraction | Additional Ingredients |
|---|---|---|---|---|
| 25 | 40-60% Hericium ernaceus 40-60% Cordyceps militaris; | 30-50% CBD 40-70% CBG | alpha pinene, limonene, beta-pinene, alpha phellandrene, terpinolene, nerolidol, and nerol | |
| 26 | 10-30% Trametes versicolor, 10-30% Ganoderma linggzhi, 10-30% Grifola frondosa, 10-30% Lentinula edodes, 10-30% Inonotus obliquus | 30-40% CBN 60-70% CBD | alpha pinene, limonene, beta-pinene, alpha phellandrene, terpinolene, nerolidol, and nerol | |
| 27 | 40-60% Hericium ernaceus; 40-60% Cordyceps militaris | 100% THC | alpha pinene, limonene, beta-pinene, alpha phellandrene, terpinolene, nerolidol, and nerol | |
| 28 | 10-30% Trametes versicolor, 10-30% Ganoderma linggzhi, 10-30% Grifola frondosa, 10-30% Lentinula edodes, 10-30% Inonotus obliquus; | 70-90% THC 10-30% CBN | alpha pinene, limonene, beta-pinene, alpha phellandrene, terpinolene, nerolidol, and nerol | |
| 29 | 40-60% Hericium ernaceus, 40-60% Cordyceps militaris | 30-50% CBD 40-70% CBG | alpha pinene, limonene, beta-pinene, alpha phellandrene, terpinolene, nerolidol, and nerol. | |
| 30 | 10-30% Trametes versicolor, 10-30% Ganoderma linggzhi, 10-30% Grifola frondosa, 10-30% Lentinula edodes, 10-30% Inonotus obliquus | 30-40% CBN 60-70% CBD | alpha pinene, limonene, beta-pinene, alpha phellandrene, terpinolene, nerolidol, and nerol | |
| 31 | 40-60% Hericium ernaceus 40-60% Cordyceps militaris; | 30-50% CBD 40-70% CBG | alpha pinene, limonene, beta-pinene, alpha phellandrene, terpinolene, nerolidol, and nerol | Hypromellose, microcrystalline cellulose, pure inositol, MCT oil, organic tapioca starch |

TABLE 3-continued

| Composition | Mushroom Extract Fraction (by weight) | Cannabinoid Extract Fraction (by weight) | Terpene Extract Fraction | Additional Ingredients |
|---|---|---|---|---|
| 32 | 10-30% Trametes versicolor, 10-30% Ganoderma linggzhi, 10-30% Grifola frondosa, 10-30% Lentinula edodes, 10-30% Inonotus obliquus | 30-40% CBN 60-70% CBD | alpha pinene, limonene, beta-pinene, alpha phellandrene, terpinolene, nerolidol, and nerol | Hypromellose, microcrystalline cellulose, pure inositol, MCT oil, organic tapioca starch. |
| 33 | 40-60% Hericium ernaceus; 40-60% Cordyceps militaris | 100% THC | alpha pinene, limonene, beta-pinene, alpha phellandrene, terpinolene, nerolidol, and nerol | Hypromellose, microcrystalline cellulose, pure inositol, MCT oil, organic tapioca starch. |
| 34 | 10-30% Trametes versicolor, 10-30% Ganoderma linggzhi, 10-30% Grifola frondosa, 10-30% Lentinula edodes, 10-30% Inonotus obliquus; | 70-90% THC 10-30% CBN | alpha pinene, limonene, beta-pinene, alpha phellandrene, terpinolene, nerolidol, and nerol | Hypromellose, microcrystalline cellulose, pure inositol, MCT oil, organic tapioca starch. |
| 35 | 40-60% Hericium ernaceus; 40-60% Cordyceps militaris | 30-50% CBD; 40-70% CBG | alpha pinene, limonene, beta-pinene, alpha phellandrene, terpinolene, nerolidol, and nerol. | MCT oil |
| 36 | 10-30% Trametes versicolor, 10-30% Ganoderma linggzhi, 10-30% Grifola frondosa, 10-30% Lentinula edodes, 10-30% Inonotus obliquus | 30-40% CBN 60-70% CBD | alpha pinene, limonene, beta-pinene, alpha phellandrene, terpinolene, nerolidol, and nerol | MCT oil |

TABLE 4

| Composition | Mushroom Extract Fraction | Cannabinoid Extract Fraction | Terpene Extract Fraction | Additional Ingredients |
|---|---|---|---|---|
| 37 | a Hericium ernaceus: Cordyceps militaris ratio between 2:1 and 1:2 by weight of the Mushroom Extract Fraction | a CBD:CBG ratio of between 2:1 and 1:2 by weight of the Cannabinoid Fraction | alpha pinene, limonene, beta-pinene, alpha phellandrene, terpinolene, nerolidol, and nerol | |
| 38 | about equal parts of Trametes versicolor, Ganoderma linggzhi, Grifola frondosa, Lentinula edodes, and Inonotus obliquus by weight of the Mushroom Extract Fraction | a CBN:CBD ratio between 2:1 and 1:2 by weight of the Cannabinoid Fraction | alpha pinene, limonene, beta-pinene, alpha phellandrene, terpinolene, nerolidol, and nerol | |
| 39 | a Hericium ernaceus: Cordyceps militaris ratio between 2:1 and 1:2 by weight of the Mushroom Extract Fraction | 100% THC by weight of the Cannabinoid Fraction | alpha pinene, limonene, beta-pinene, alpha phellandrene, terpinolene, nerolidol, and nerol | |
| 40 | about equal parts of Trametes versicolor, Ganoderma linggzhi, Grifola frondosa, Lentinula edodes, and Inonotus obliquus by weight of the Mushroom Extract Fraction | a THC:CBN ratio between 6:1 and 2:1 by weight of the Cannabinoid Fraction | alpha pinene, limonene, beta-pinene, alpha phellandrene, terpinolene, nerolidol, and nerol | |
| 41 | a Hericium ernaceus: Cordyceps militaris ratio between 2:1 and 1:2 by weight of the Mushroom | a CBD:CBG ratio between 2:1 and 1:2 by weight of the Cannabinoid | alpha pinene, limonene, beta-pinene, alpha phellandrene, terpinolene, nerolidol, and nerol. | |
| 42 | about equal parts of Trametes versicolor, Ganoderma linggzhi, Grifola frondosa, Lentinula edodes, and Inonotus obliquus by weight of the Mushroom Extract Fraction | a CBN:CBD ratio between 2:1 and 1:2 by weight of the Cannabinoid Fraction | alpha pinene, limonene, beta-pinene, alpha phellandrene, terpinolene, nerolidol, and nerol | |
| 43 | a Hericium ernaceus: Cordyceps militaris ratio between 2:1 and 1:2 by weight of the Mushroom Extract Fraction | a CBD:CBG ratio of between 2:1 and 1:2 by weight of the Cannabinoid Fraction | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, guarana |
| 44 | about equal parts of Trametes versicolor, Ganoderma linggzhi, Grifola frondosa, Lentinula | a CBN:CBD ratio between 2:1 and 1:2 by weight of the Cannabinoid Fraction | alpha pinene, limonene, beta-pinene, alpha phellandrene, terpinolene, nerolidol, and nerol | Hypromellose, microcrystalline cellulose, pure inositol, MCT oil, organic tapioca starch, beta-D- |

TABLE 4-continued

| Composition | Mushroom Extract Fraction | Cannabinoid Extract Fraction | Terpene Extract Fraction | Additional Ingredients |
|---|---|---|---|---|
| | edodes, and Inonotus obliquus by weight of the Mushroom Extract Fraction | | | glucans, valerian root |
| 45 | a Hericium ernaceus: Cordyceps militaris ratio between 2:1 and 1:2 by weight of the Mushroom Extract Fraction | 100% THC by weight of the Cannabinoid Fraction | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, guarana. |
| 46 | about equal parts of Trametes versicolor, Ganoderma linggzhi, Grifola frondosa, Lentinula edodes, and Inonotus obliquus by weight of the Mushroom Extract Fraction | a THC:CBN ratio between 6:1 and 2:1 by weight of the Cannabinoid Fraction | alpha pinene, limonene, beta-pinene, alpha phellandrene, terpinolene, nerolidol, and nerol | Hypromellose, microcrystalline cellulose, pure inositol, MCT oil, organic tapioca starch, beta-D-glucans, guarana. |
| 47 | a Hericium ernaceus: Cordyceps militaris ratio between 2:1 and 1:2 by weight of the Mushroom Extract Fraction | a CBD:CBG ratio between 2:1 and 1:2 by weight of the Cannabinoid Fraction | alpha pinene, limonene, beta-pinene, alpha phellandrene, terpinolene, nerolidol, and nerol. | MCT oil, beta-D-glucans |
| 48 | about equal parts of Trametes versicolor, Ganoderma linggzhi, Grifola frondosa, Lentinula edodes, and Inonotus obliquus by weight of the Mushroom Extract Fraction | a CBN:CBD ratio between 2:1 and 1:2 by weight of the Cannabinoid Fraction | alpha pinene, limonene, beta-pinene, alpha phellandrene, terpinolene, nerolidol, and nerol | MCT oil, beta-D-glucans |

Product 1

In some embodiments, provided herein is a composition comprising: a) a Cannabinoid Fraction comprising i) cannabidiol (CBD); ii) cannabigerol (CBG); and b) a Mushroom Extract Fraction comprising i) Hericium ernaceus; ii) Cordyceps militaris; and c) a Terpene Fraction.

In some embodiments, a composition comprises a Cannabinoid Fraction comprising CBD and CBG; a Mushroom Extract Fraction comprising Hericium ernaceus and Cordyceps militaris, and a Terpene Fraction.

In some embodiments, the Cannabinoid Fraction comprises CBD and CBG. In some embodiments, the Cannabinoid Fraction comprises a CBD:CBG ratio of between about 4:1 and 1:4 by weight, including all ratios in between. In some embodiments, the Cannabinoid Fraction comprises a CBD:CBG ratio of between about 2:1 and 1:2 by weight, including all ratios in between, for example, 2:1, 1.5:1, 4:3, 3:4, 1:1, and 1:2. In some embodiments, the Cannabinoid Fraction comprises a CBD:CBG ratio of about 3:4. In some embodiments, the Cannabinoid Fraction comprises between about 30-50% CBD and 40-70% CBG by weight, for example, about 30%, about 35%, about 40%, about 45%, or about 50% CBD by weight, and about 40%, about 45%, about 50%, about 55%, about 60%, about 65%, or about 70% CBG by weight.

In some embodiments, the Terpene Fraction comprises alpha pinene, limonene, beta pinene, alpha phellandrene, terpinolene, nerolidol, and nerol.

In some embodiments, the Mushroom Extract Fraction comprises a Hericium ernaceus:Cordyceps militaries ratio between 2:1 and 1:2 by weight. In some embodiments, the Mushroom Extract Fraction comprises a Hericium ernaceus:Cordyceps militaries ratio of about 1:1 by weight. In some embodiments, the Mushroom Extract Faction comprises between 40-60% Hericium ernaceus and 40-60% Cordyceps militaris by weight of the Mushroom Extract Fraction.

In some embodiments, the composition is formulated as a powder encapsulated into a capsule.

In some embodiments, the composition comprises less than 2% starch by weight of the composition.

In some embodiments, the composition comprises microcrystalline cellulose.

In some embodiments, the composition comprises MCT oil.

In some embodiments, the composition comprises hypromellose.

In some embodiments, the composition comprises inositol.

In some embodiments, the composition comprises hypromellose, microcrystalline cellulose, inositol, and MCT oil.

In some embodiments, the composition comprises greater than about 12% beta-D-glucans by weight of the composition.

In some embodiments, the composition comprises less than about 2% guarana by weight of the composition.

In some embodiments, the composition comprises a triterpene selected from the group consisting of ergosterol peroxide; cerevisterol; 3β.5α,9α,-trihydroxy-ergosta-7,22-dien-6-one; interpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the composition comprises a Cannabinoid Fraction to Mushroom Extract Fraction ratio of between about 1:8 and 1:10 by weight, for example, about 1:8, 2:17, 1:9, 2:19, or 1:10 by weight.

In some embodiments, the composition comprises a Cannabinoid Fraction to Mushroom Extract Fraction ratio of about 7:60 by weight.

In some embodiments, provided herein is a a) a Cannabinoid Fraction comprising i) 15 mg cannabidiol (CBD); ii) 20 mg cannabigerol (CBG); and b) a Mushroom Extract Fraction comprising i) 150 mg Hericium ernaceus; ii) 150 mg Cordyceps militaris; and c) a Terpene Fraction comprising alpha pinene, limonene, beta-pinene, alpha phellandrene, terpinolene, nerolidol, and nerol.

In some embodiments, the composition is Composition 1 or Composition 7 of Table 1.

Product 2

In some embodiments, provided herein is a composition comprising a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction.

In some embodiments, the Cannabinoid Fraction comprises CBN and CBD. In some embodiments, the Cannabinoid Fraction comprises a CBN:CBD ratio of between about 4:1 and 1:4 by weight, including all ratios in between. In some embodiments, the Cannabinoid Fraction comprises a CBN:CBD ratio of between about 2:1 and 1:2 by weight, including all ratios in between, for example, 2:1, 1.5:1, 4:3, 3:4, 1:1, and 1:2. In some embodiments, the Cannabinoid Fraction comprises a CBN:CBD ratio of about 2:3. In some embodiments, the Cannabinoid Fraction comprises between about 30-40% CBD and 60-70% CBG by weight, for example, about 30%, about 35%, or about 40% CBD by weight and about 60%, about 65%, or about 70% CBG by weight.

In some embodiments, the Terpene Fraction comprises alpha pinene, limonene, beta pinene, alpha phellandrene, terpinolene, nerolidol, and nerol.

In some embodiments, the Mushroom Extract Fraction comprises about equal parts of *Trametes versicolor, Ganoderma lingzhi, Grifola frondosa, Lentinula edodes*, and *Inonotus obliquus* by weight. In some embodiments, the Mushroom Extract Fraction comprises between 10-30% *Trametes versicolor,* 10-30% *Ganoderma lingzhi,* 10-30% *Grifola frondosa,* 10-30% *Lentinula edodes*, and 10-30% *Inonotus obliquus* by weight of the Mushroom Extract Fraction.

In some embodiments, the composition is formulated as a powder encapsulated into a capsule.

In some embodiments, the composition comprises less than 2% starch by weight of the composition.

In some embodiments, the composition comprises hypromellose.

In some embodiments, the composition comprises microcrystalline cellulose.

In some embodiments, the composition comprises MCT oil.

In some embodiments, the composition comprises inositol.

In some embodiments, the composition comprises hypromellose, microcrystalline cellulose, inositol, and MCT oil.

In some embodiments, the composition comprises greater than about 12% beta-D-glucans by weight of the composition.

In some embodiments, the composition comprises less than about 2% valerian root by weight of the composition.

In some embodiments, the composition comprises a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the composition comprises a Cannabinoid Fraction to Mushroom Extract Fraction ratio of between about 1:8 and 1:10 by weight, for example, about 1:8, 2:17, 1:9, 2:19, or 1:10 by weight.

In some embodiments, the composition comprises a Cannabinoid Fraction to Mushroom Extract Fraction ratio of about 7:60 by weight.

In some embodiments, provided herein is a composition comprising: a) a Cannabinoid Fraction comprising i) 10 mg cannabinol (CBN); ii) 15 mg cannabidiol (CBD); and b) a Mushroom Extract Fraction comprising i) 60 mg *Trametes versicolor*, ii) 60 mg *Ganoderma lingzhi*, iii) 60 mg *Grifola frondosa*, iv) 60 mg *Lentinula edodes*, v) 60 mg *Inonotus obliquus*; and c) a Terpene Fraction comprising alpha pinene, limonene, beta-pinene, alpha phellandrene, terpinolene, nerolidol, and nerol.

In some embodiments, the composition is Composition 2 or Composition 8 of Table 1.

Product 3

In some embodiments, provided herein is a composition comprising: a) a Cannabinoid Fraction comprising tetrahydrocannabinol (THC); b) a Mushroom Extract Fraction comprising i) *Hericium ernaceus*; ii) *Cordyceps militaris*; and c) a Terpene Fraction.

In some embodiments, the Cannabinoid Fraction comprises THC. In some embodiments, the Cannabinoid Fraction comprises about 100% THC by weight.

In some embodiments, the Terpene Fraction comprises alpha pinene, limonene, beta pinene, alpha phellandrene, terpinolene, nerolidol, and nerol.

In some embodiments, the Mushroom Extract Fraction comprises a *Hericium ernaceus:Cordyceps militaris* ratio between 2:1 and 1:2 by weight. In some embodiments, the Mushroom Extract Fraction comprises a *Hericium ernaceus:Cordyceps militaris* ratio of about 1:1 by weight. In some embodiments, the Mushroom Extract Faction comprises between 40-60% *Hericium ernaceus* and 40-60% *Cordyceps militaris* by weight of the Mushroom Extract Fraction.

In some embodiments, the composition is formulated as a powder encapsulated into a capsule.

In some embodiments, the composition comprises less than 2% starch by weight of the composition.

In some embodiments, the composition comprises microcrystalline cellulose.

In some embodiments, the composition comprises MCT oil.

In some embodiments, the composition comprises hypromellose.

In some embodiments, the composition comprises inositol.

In some embodiments, the composition comprises hypromellose, microcrystalline cellulose, inositol, and MCT oil.

In some embodiments, the composition comprises greater than about 12% beta-D-glucans by weight of the composition In some embodiments, the composition comprises less than about 2% caffeine by weight of the composition.

In some embodiments, the composition comprises less than about 2% guarana by weight of the composition.

In some embodiments, the composition comprises a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the composition comprises a Cannabinoid Fraction to Mushroom Extract Fraction ratio of between about 1:8 and 1:11 by weight, for example, about 1:8, 2:17, 1:9, 2:19, 1:10, 2:21, or 1:11 by weight.

In some embodiments, the composition comprises a Cannabinoid Fraction to Mushroom Extract Fraction ratio of about 1:10 by weight.

In some embodiments, provided herein is a composition comprising: a) a Cannabinoid Fraction comprising 10 mg tetrahydrocannabinol (THC); b) a Mushroom Extract Fraction comprising i) 50 mg *Hericium ernaceus*; ii) 50 mg *Cordyceps militaris*; and c) a Terpene Fraction comprising alpha pinene, limonene, beta-pinene, alpha phellandrene, terpinolene, nerolidol, and nerol.

In some embodiments, the composition is Composition 3 or Composition 9 of Table 1.

Product 4

In some embodiments, provided herein is a composition comprising: a) a Cannabinoid Fraction comprising i) tetrahydrocannabinol (THC); ii) cannabinol (CBN); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction.

In some embodiments, the Cannabinoid Fraction comprises THC and CBN. In some embodiments, the Cannabinoid Fraction comprises a THC:CBN ratio of between about 6:1 and 2:1 by weight, including all ratios in between, for example, 6:1, 5:1, 4:1, 3:1, 2:1, and 1:2. In some embodiments, the Cannabinoid Fraction comprises a THC:CBN ratio of about 4:1. In some embodiments, the Cannabinoid Fraction comprises between about 70-90% THC and 10-30% CBN by weight, for example, about 70%, about 75%, about 80%, about 85%, or about 90% THC by weight and about 10%, about 15%, about 20%, about 25%, or about 30% CBN by weight.

In some embodiments, the Terpene Fraction comprises alpha pinene, limonene, beta pinene, alpha phellandrene, terpinolene, nerolidol, nerol, myrcene, and beta caryophyllene.

In some embodiments, the Mushroom Extract Fraction comprises about equal parts of *Trametes versicolor, Ganoderma lingzhi, Grifola frondosa, Lentinula edodes*, and *Inonotus obliquus* by weight. In some embodiments, the Mushroom Extract Fraction comprises comprises between 10-30% *Trametes versicolor*, 10-30% *Ganoderma lingzhi*, 10-30% *Grifola frondosa*, 10-30% *Lentinula edodes*, and 10-30% *Inonotus obliquus* by weight of the Mushroom Extract Fraction.

In some embodiments, the composition is formulated as a powder encapsulated into a capsule.

In some embodiments, the composition comprises less than 2% starch by weight of the composition.

In some embodiments, the composition comprises hypromellose, microcrystalline cellulose, inositol, and MCT oil.

In some embodiments, the composition comprises microcrystalline cellulose.

In some embodiments, the composition comprises MCT oil.

In some embodiments, the composition comprises hypromellose.

In some embodiments, the composition comprises inositol.

In some embodiments, the composition comprises greater than about 12% beta-D-glucans by weight of the composition.

In some embodiments, the composition comprises less than about 2% guarana by weight of the composition.

In some embodiments, the composition comprises a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the composition comprises a Cannabinoid Fraction to Mushroom Extract Fraction ratio of between about 1:6 and 1:11 by weight, for example, about 1:6, 2:13, 1:7, 2:15, 1:8, 2:17, 1:9, 2:19, 1:10, 2:21, or 1:11 by weight.

In some embodiments, the composition comprises a Cannabinoid Fraction to Mushroom Extract Fraction ratio of between about 1:8 and 1:10 by weight, for example, about 1:8, 2:17, 1:9, 2:19, or 1:10 by weight.

In some embodiments, the composition comprises a Cannabinoid Fraction to Mushroom Extract Fraction ratio of about 1:8 by weight.

In some embodiments, provided herein is a composition comprising: a) a Cannabinoid Fraction comprising i) 10 mg tetrahydrocannabinol (THC); ii) 2.5 mg cannabinol (CBN); and b) a Mushroom Extract Fraction comprising i) 20 mg *Trametes versicolor*, ii) 20 mg *Ganoderma* lingzhi, iii) 20 mg *Grifola frondosa*, iv) 20 mg *Lentinula edodes*, v) 20 mg *Inonotus obliquus*; and c) a Terpene Fraction comprising alpha pinene, limonene, beta-pinene, alpha phellandrene, terpinolene, nerolidol, and nerol.

In some embodiments, the composition is Composition 4 or Composition 10 of Table 1.

Product 5

In some embodiments, provided herein is a composition comprising: a) a Cannabinoid Fraction comprising i) cannabidiol (CBD); ii) cannabigerol (CBG); and b) a Mushroom Extract Fraction comprising i) *Hericium ernaceus*; ii) *Cordyceps militaris*; and c) a Terpene Fraction.

In some embodiments, the Cannabinoid Fraction comprises CBD and CBG. In some embodiments, the Cannabinoid Fraction comprises a CBD:CBG ratio of between about 4:1 and 1:4 by weight, including all ratios in between. In some embodiments, the Cannabinoid Fraction comprises a CBD:CBG ratio of between about 2:1 and 1:2 by weight, including all ratios in between, for example, 2:1, 1.5:1, 4:3, 3:4, 1:1, and 1:2. In some embodiments, the Cannabinoid Fraction comprises a CBD:CBG ratio of about 3:4. In some embodiments, the Cannabinoid Fraction comprises between about 30-50% CBD and 40-70% CBG by weight, for example, about 30%, about 35%, about 40%, about 45%, or about 50% CBD by weight, and about 40%, about 45%, about 50%, about 55%, about 60%, about 65%, or about 70% CBG by weight.

In some embodiments, the Terpene Fraction comprises alpha pinene, limonene, beta pinene, alpha phellandrene, terpinolene, nerolidol, and nerol.

In some embodiments, the Mushroom Extract Fraction comprises a *Hericium ernaceus:Cordyceps militaris* ratio between 2:1 and 1:2 by weight. In some embodiments, the Mushroom Extract Fraction comprises a *Hericium ernaceus:Cordyceps militaris* ratio of about 1:1 by weight. In some embodiments, the Mushroom Extract Faction comprises between 40-60% *Hericium* ernaceus and 40-60% *Cordyceps militaris* by weight of the Mushroom Extract Fraction.

In some embodiments, the composition is formulated into a liquid. In some embodiments, the liquid is delivered to a subject by sublingual drops.

In some embodiments, the composition comprises less than 2% starch by weight of the composition.

In some embodiments, the composition comprises microcrystalline cellulose.

In some embodiments, the composition comprises MCT oil.

In some embodiments, the composition comprises hypromellose, microcrystalline cellulose, inositol, and MCT oil.

In some embodiments, the composition comprises at least about 5% beta-D-glucans by volume of the composition.

In some embodiments, the composition comprises a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the composition comprises a Cannabinoid Fraction to Mushroom Extract Fraction ratio of between about 3:1 and 1:1 by weight, for example, about 3:1, 12:5, 2:1, 12:7, 3:2, 4:3, or 1:1 by weight.

In some embodiments, the composition comprises a Cannabinoid Fraction to Mushroom Extract Fraction ratio of about 21:10 by weight.

In some embodiments, provided herein is a composition comprising: a) a Cannabinoid Fraction comprising i) 450 mg cannabidiol (CBD); ii) 600 mg cannabigerol (CBG); and b) a Mushroom Extract Fraction comprising i) 250 mg *Hericium ernaceus*; ii) 250 mg *Cordyceps militaris*; and c) a Terpene Fraction comprising alpha pinene, limonene, beta-pinene, alpha phellandrene, terpinolene, nerolidol, and nerol.

In some embodiments, the composition is Composition 5 or Composition 11 of Table 1.

Product 6

In some embodiments, provided herein is a composition comprising: a) a Cannabinoid Fraction comprising i) cannabinol (CBN); ii) cannabidiol (CBD); and b) a Mushroom Extract Fraction comprising i) *Trametes versicolor*, ii) *Ganoderma lingzhi*, iii) *Grifola frondosa*, iv) *Lentinula edodes*, v) *Inonotus obliquus*; and c) a Terpene Fraction.

In some embodiments, the Cannabinoid Fraction comprises CBN and CBD. In some embodiments, the Cannabinoid Fraction comprises a CBN:CBD ratio of between about 4:1 and 1:4 by weight, including all ratios in between. In some embodiments, the Cannabinoid Fraction comprises a CBN:CBD ratio of between about 2:1 and 1:2 by weight, including all ratios in between, for example, 2:1, 1.5:1, 4:3, 3:4, 1:1, and 1:2. In some embodiments, the Cannabinoid Fraction comprises a CBN:CBD ratio of about 2:3. In some embodiments, the Cannabinoid Fraction comprises between about 30-40% CBD and 60-70% CBG by weight, for example, about 30%, about 35%, or about 40% CBD by weight and about 60%, about 65%, or about 70% CBG by weight.

In some embodiments, the Terpene Fraction comprises alpha pinene, limonene, beta pinene, alpha phellandrene, terpinolene, nerolidol, and nerol.

In some embodiments, the Mushroom Extract Fraction comprises about equal parts of *Trametes versicolor, Ganoderma lingzhi, Grifola frondosa, Lentinula edodes*, and *Inonotus obliquus* by weight. In some embodiments, the Mushroom Extract Fraction comprises between 10-30% *Trametes versicolor*, 10-30% *Ganoderma lingzhi*, 10-30% *Grifola frondosa*, 10-30% *Lentinula edodes*, and 10-30% *Inonotus obliquus* by weight of the Mushroom Extract Fraction.

In some embodiments, the formulation is a liquid. In some embodiments, the liquid is delivered to a subject by sublingual drops.

In some embodiments, the composition comprises less than 2% starch by weight of the composition.

In some embodiments, the composition comprises microcrystalline cellulose.

In some embodiments, the composition comprises MCT oil.

In some embodiments, the composition comprises hypromellose, microcrystalline cellulose, inositol, and MCT oil.

In some embodiments, the composition comprises at least about 5% beta-D-glucans by volume of the composition.

In some embodiments, the composition comprises a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

In some embodiments, the composition comprises a Cannabinoid Fraction to Mushroom Extract Fraction ratio of between about 2:1 and 1:2 by weight, for example, about 2:1, 3:2, 1:1, 2:3, 1:1, and 1:2 by weight.

In some embodiments, the composition comprises a Cannabinoid Fraction to Mushroom Extract Fraction ratio of about 3:2 by weight.

In some embodiments, provided herein is a composition comprising: a) a Cannabinoid Fraction comprising i) 300 mg cannabinol (CBN); ii) 450 mg cannabidiol (CBD); and b) a Mushroom Extract Fraction comprising i) 100 mg *Trametes versicolor*, ii) 100 mg *Ganoderma* lingzhi, iii) 100 mg *Grifola frondosa*, iv) 100 mg *Lentinula edodes*, v) 100 mg *Inonotus obliquus*; and c) a Terpene Fraction comprising alpha pinene, limonene, beta-pinene, alpha phellandrene, terpinolene, nerolidol, and nerol.

In some embodiments, the composition is Composition 6 or Composition 12 of Table 1.

VI. Formulations

The compositions of the present disclosure can employ various formulations and comprise additional ingredients for administration to subjects including formulation as tablets, capsules, pills, powders, granules, solutions, suspensions, emulsions, elixir, lotion, cream, gel, ointment, tincture, paste, foam, aerosol, irrigation, spray, suppository, or bandage. The form of the resulting formulation depends upon a number of factors, including the intended mode of administration (e.g. oral administration, enteral administration, parenteral administration, and topical application to the skin, scalp, eyes, and/or nasal, buccal or sublingual mucosa), selected carriers or vehicles, the solubility of the composition in the selected carrier or vehicle. Guidance regarding formulations that are suitable for various types of administration is found in Remington's Pharmaceutical Sciences, Mace Publishing Company, Philadelphia, Pa., 17th ed. (1985). For a brief review of methods for drug delivery, see, Langer, Science 249:1527-1533 (1990).

In some embodiments, the formulation is a powder encapsulated into a capsule. In some embodiments, the formulation is a liquid. In some embodiments, the liquid is delivered by sublingual drops.

In some embodiments, the composition is formulated for oral, enteral, or parenteral delivery. The disclosure below describes such formulations.

Oral

In some embodiments, the composition is formulated for oral delivery. In some embodiments, the composition is administered sublingually. In some embodiments, the composition is administered orally as a capsule.

Oral pharmaceutical dosage forms can be either solid or liquid.

In some embodiments, the oral pharmaceutical dosage form is a solid. The solid dosage forms can be tablets, capsules, granules, and bulk powders. Types of oral tablets include compressed, chewable lozenges and tablets which can be enteric-coated, sugar-coated, or film-coated. Capsules can be hard or soft gelatin capsules, while granules and powders can be provided in non-effervescent or effervescent form with the combination of other ingredients known to those skilled in the art. In other embodiments, the oral dosage form may be an osmotic-controlled release oral delivery system (OROS). In other embodiments, the oral dosage form may include matrix-embedded dosage forms or related devices. In some embodiments, the present oral dosage forms may include orally-disintegrating tablets. Pharmaceutically acceptable carriers utilized in tablets include binders, lubricants, diluents, disintegrating agents, coloring agents, flavoring agents, and wetting agents.

In some embodiments, the oral pharmaceutical dosage form is a liquid. Liquid oral dosage forms include aqueous solutions, emulsions, suspensions, solutions, and/or suspensions reconstituted from non-effervescent granules and effervescent preparations reconstituted from effervescent granules. Aqueous solutions include, for example, elixirs and syrups. Elixirs are clear, sweetened, hydroalcoholic preparations. Pharmaceutically acceptable carriers used in elixirs include solvents. Syrups can be concentrated aqueous solutions of a sugar, for example, sucrose, and can contain a preservative. An emulsion is a two-phase system in which one liquid is dispersed in the form of small globules throughout another liquid, typically oil-in water or water-in-oil. Pharmaceutically acceptable carriers used in emulsions are non-aqueous liquids, emulsifying agents and preservatives. Suspensions can use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, can include organic acids and a source of carbon dioxide. Coloring and flavoring agents can be used in all of the above dosage forms.

Enteral

In some embodiments, the composition is administered enterally. Pharmaceutical dosage forms for rectal administration can be rectal suppositories, capsules and tablets for systemic effect. Rectal suppositories as used herein mean solid bodies for insertion into the rectum which melt or soften at body temperature releasing the pharmacologically and/or therapeutically active ingredients contained in the composition of this invention. Pharmaceutically acceptable substances utilized in rectal suppositories are bases or vehicles and agents to raise the melting point. Examples of bases include cocoa butter (theobroma oil), glycerin-gelatin, carbowax, polyoxyethylene glycol and mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

Parenteral

In some embodiments, the compositions are administered parenterally. Parenteral administration of the formulations of the present invention includes intravenous, subcutaneous, and intramuscular administrations of immediate, sustained, extended, and/or modified release formulations. Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances.

Sustained/Immediate Release

In some embodiments, the compositions described herein are formulated in a dosage form for immediate or sustained release. By "immediate release" formulation is meant a dosage form that is intended to release substantially the entire dose of active ingredient on administration with no enhanced, delayed, controlled, sustained, or extended release effect, generally over a short period of time (e.g., 30 minutes). "Sustained release" or "extended release" means that the active ingredient(s) of the composition is released from the formulation at a controlled rate so that therapeutically beneficial blood levels (but below toxic levels) of the active ingredient(s) are maintained over an extended period of time. Alternatively, "sustained release" or "extended release" means that the desired pharmacologic effect is maintained over an extended period of time.

Tinctures

In some embodiments, the compositions described herein are formulated as a tincture. In aspects, the tincture is formulated to have a chocolate flavor, or a mint flavor, or a mint chocolate flavor. In aspects, the tincture is formulated to have a peppermint flavor. In aspects, the tincture is formulated to have a citrus flavor, such as a grapefruit flavor, a lemon flavor, or an orange flavor. In aspects, the tincture is formulated to have a passionfruit flavor. In aspects, the tincture is formulated to have a vanilla flavor. In aspects, the tincture is formulated to have a ginger flavor. In some embodiments, the tincture is formulated to have a lemon, orange, and ginger flavor. In some embodiments, the tincture is formulated to have an orange and a vanilla flavor. In some embodiments, the tincture is formulated to have a green tea, lemon, orange, and ginger flavor. In some embodiments, the tincture is formulated to have a raspberry flavor. In some embodiments, the tincture is formulated to have a blackberry flavor. In some embodiments, the tincture is formulated to have a vanilla flavor.

Sublingual delivery of tincture provides rapid onset of active medicine by delivering the drug very quickly to the bloodstream. Quick delivery to the blood disperses medicine through the body and to the brain. Oral mucosal (e.g. sub- or supralingual) administration of drugs is often the route of administration of choice when the drug shows a large first-pass effect after oral delivery. Systemic exposure of drugs after oral mucosal administration is often expected to be a route of administration with a fast onset of action. See, Bartlett et al., "Understanding the Oral Mucosal Absorption and Resulting Clinical Pharmacokinetics of Asenapine," AAPS PharmSciTech, 2012, Vol. 13(4), pgs. 1110-1115, incorporated by reference herein.

Inhalation Delivery

In some embodiments, the compositions described herein are formulated as an inhaler. In some aspects, the compositions described herein are formulated as a nasal spray.

Topical Cream

In some embodiments, the compositions described herein are formulated as a topical cream.

Vaporizable Oil

In some embodiments, the compositions described herein are formulated as a vaporizable oil.

Additional Ingredients

In some embodiments, additional components are optionally added to the compositions of the present disclosure to improve the taste and/or physical properties of the composition (such as stability and viscosity). Such additional components include, but are not limited to, sweeteners, natural flavorants, artificial flavorants, colorants, antioxidants, preservatives, chelating agents, viscomodulators, tonicifiers, odorants, opacifiers, suspending agents, binders, thickeners, carriers and mixtures thereof, including, but not limited to, xanthum gum, carboxymethylcellulose, carboxyethylcellulose, hydroxypropylcellulose, methylcellulose, microcrystalline cellulose, starches, dextrins, maltodextrins, other polyols (including sugar alcohols, such as sorbitol, lactitol or mannitol), carbohydrates (e.g., lactose), propylene glycol alginate, gellan gum, guar, pectin, tragacanth gum, gum acacia, locust bean gum, gum arabic, mannitol, sucralose, silicon dioxide, stearic acid, hydroxypropyl methylcellulose, mono-, di- and triglycerides (acyl glycerols), ether and sugar acetates or other acid esters such as dimethyl acetate, ethyl acetate, isopropyl acetate, ethylhexyl acetate, butyl acetate, triethyl citrate, dimethyl butyrate and the like. In some embodiments, the compositions comprise hydroxypropyl methylcellulose also referred to herein as "hypromellose."

In some embodiments, the compositions of the present disclosure are formulated with one or more carriers. The term "carrier" as used herein encompasses carriers, excipients, and diluents, meaning a material, composition or vehicle, such as a liquid or solid filler, diluent, excipient, binder, disintegrant, lubricant, solvent or encapsulating material involved in carrying or transporting a pharmaceutical agent from one organ, or portion of the body, to another organ or portion of the body.

The range of materials that are suitable for use as fillers, disintegrants, binders, lubricants, diluents, plasticizers, anti-caking agents, solubilizing agents, stabilizers, anti-oxidants, anti-adherents, preservatives, glidants, flavorants, sweeteners, and pigments will be well known to the person skilled in the art.

Suitable fillers include inert, relatively tasteless or pleasant tasting materials. A nonlimiting list of suitable fillers includes cellulose (e.g. microcrystalline cellulose), starch (e.g. corn starch), pregelatinized starch, modified starch, dibasic calcium phosphate dihydrate, calcium sulfate trihydrate, calcium sulfate dihydrate, calcium carbonate, dextrose, sucrose, lactose, mannitol, and sorbitol. Lactose monohydrate is used as filler in certain embodiments. In certain embodiments, the filler is at least one member selected from the group consisting of: lactose monohydrate, cellulose microcrystalline, corn starch, and combinations thereof. In some embodiments, the composition comprises microcrystalline cellulose.

Suitable carrier oils (i.e., a substance facilitating the administration of the compositions disclosed herein) are described herein. In some embodiments, the carrier oil is grapeseed oil. In one embodiment, the carrier oil is coconut oil. In some embodiments, the carrier oil is polyethylene glycol. In some embodiments, the carrier oil is olive oil.

In some embodiments, the carrier oil is MCT oil. MCT oil is comprised of medium chain triglycerides and can, in some embodiments, be sourced from coconut oil. MCTs are easily digested and processed in the body.

In some embodiments, the carrier oil is then combined with a food product. In a further embodiment, the carrier oil is then combined with a beverage product. In a further embodiment, the carrier oil is then combined with a personal care product, e.g., topical cream, soap, shampoo, etc. In a further embodiment, the carrier oil is then combined with a drug. In a further embodiment, the carrier oil is then combined with a non-*cannabis* plant extract. In a further embodiment, the carrier oil combined with the composition is used with a device, e.g., vaporizer, intravenous drug, etc.

In some embodiments, the compositions comprise a disintegrant. Non-limiting examples of suitable disintegrants include cross-linked polymers such as crospovidone, croscarmellose sodium, etc., and modified starches such as sodium starch glycolate.

A nonlimiting list of suitable binders includes disaccharides such as sucrose and lactose, polysaccharides such as cellulose, starches, microcrystalline cellulose, modified celluloses such as hydroxypropyl cellulose, sugar alcohols such as xylitol, sorbitol, or maltitol, proteins such as gelatin, synthetic polymers such as polyvinyl pyrrolidone and polyethylene glycol, starches, such as potato starch, wheat starch, corn starch, and gums, such as gum tragacanth, acacia gum and gelatin. In some embodiments, the compositions comprise starch. In some embodiments, the starch is tapioca starch. In some embodiments, the compositions comprise less than 2% starch by weight of the composition, for example, less than about 1.9%, less than about 1.8%, less than about 1.7%, less than about 1.6%, less than about 1.5%, less than about 1.4%, less than about 1.3%, less than about 1.2%, less than about 1.1%, less than about 1%, less than about 0.9%, less than about 0.8%, less than about 0.7%, less than about 0.6%, less than about 0.5%, less than about 0.4%, less than about 0.3%, less than about 0.2%, less than about 0.1%, or less than about 0.05% of starch by weight of the composition.

A nonlimiting list of suitable lubricants includes magnesium stearate, stearic acid, sodium stearyl fumarate and the like.

Plasticizers utilized in some embodiments include, but are not limited to, citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, dibutyrate, -dipropionate; tributyl phosphate, tributyrin; polyethylene glycol sorbitan monooleate (polysorbates such as Polysorbar 50); sorbitan monooleate.

Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Nonlimiting examples of water-soluble pharmaceutical diluents include lactose, dextrose, sucrose, or mixtures thereof. In some embodiments, the compositions comprise inositol.

Optionally, the formulations may also contain other ingredients such as wetting agents (e.g., polyethoxylated castor oil, polyethoxylated hydrogenated castor oil, polyethoxylated fatty acid from castor oil, polyethoxylated fatty acid from hydrogenated castor oil), flavors, coloring agents, buffering agents, and/or other conventional ingredients.

In some embodiments, the pharmaceutical compositions described herein comprise one or more flavoring agents. Flavoring agents can be selected from Non-limited examples of flavorings include vanilla, chocolate, hazelnut, caramel, cinnamon, mint, eggnog, apple, apricot, aromatic bitters, banana, berry, blackberry, blueberry, celery, cherry, cranberry, strawberry, raspberry, juniper berry, brandy, cachaca, carrot, citrus, lemon, lime, orange, grapefruit, tangerine, coconut, cola, menthol, gin, ginger, licorice, hot, milk, nut, almond, macadamia nut, peanut, pecan, pistachio, walnut, peach, pear, pepper, pineapple, plum, quinine, rum, white rum, dark rum, sangria, shellfish, clam, tea, black tea, green tea, tequila, tomato, top note, tropical, vermouth, dry vermouth, sweet vermouth, whiskey, bourbon whiskey, Irish whiskey, rye whiskey, Scotch whisky, Canadian whiskey, red pepper, black pepper, horseradish, wasabi, jalapeno pepper, chipotle pepper essential oils, concretes, absolutes, resins, resinoids, balms, tinctures, soybean oil, coconut oil, palm oil, kern oil, sunflower oil, peanut oil, almond oil, cocoa butter, amyris oil, angelica seed oil, angelica root oil, aniseed oil, anise seed oil, valerian oil, basil oil, tarragon oil, eucalyptus citriodora oil, eucalyptus oil, fennel oil, fir needle oil, galbanum oil, galbanum resin, geranium oil, ginger, grapefruit oil, guaiac wood oil, guaiac balsam, guaiac balsam oil, helichrysum absolute, helichrysum oil, ginger oil, green tea, iris root absolute, iris root oil, jasmin absolute, calmus oil, chamomile oil bleu, chamomile oil roman, carrot seed oil, cascarilla oil, mint oil, carvi oil, labdanum oil, labdanum absolute, labdanum resin, lavandin absolute, lavandin oil, lavender absolute, lavender oil, lemon oil, lemongrass oil, *Bursera penicillata* (linaloe) oil, litsea-cubeba oil, bay laurel leaf oil, macis oil, marjoram oil, mandarin oil, massoirinde oil, mimosa absolute, ambrette seed oil, ambrette tincture, muskatelle salbei oil, nutmeg oil, orange, orange blossom absolute, orange oil, oregano oil, palmarosa oil, patchouli oil, perilla oil, parsley leaf oil, parsley seed oil, clove seed oil, peppermint oil, pepper oil, pimento oil, pine oil, poley oil, raspberry, rose absolute, rose wood oil, rose oil, rosemary oil, sage oil, lavandin, sage oil Spanish, sandalwood oil, celery seed oil, lavender spike oil, star anis oil, styrax oil, tagetes oil, pine needle oil, tea-tree oil, turpentine oil, thyme oil, tolu balm, tonka absolute, tuberose absolute, vanilla, vanilla extract, violet leaf absolute, verbena oil, vetiver oil, juniper berry oil, wine yeast oil, wormwood oil, wintergreen oil, ylang ylang oil, hyssop oil, civet absolute, cinnamon leaf oil, cinnamon bark oil or any other type of food flavoring or edible substance or a combination thereof. In some embodiments, the flavoring agent is selected from green tea, Lemon Oil, Ginger Flavoring, Orange Flavoring, Vanilla Flavoring, Raspberry Flavoring and Blackberry Flavoring.

In some embodiments, the compositions described herein comprise beta-D-glucans. In some embodiments, the compositions comprise greater than about 12% beta-D-glucans by weight of the composition, for example, greater than about 12%, greater than about 13%, greater than about 14%, greater than about 15%, greater than about 16%, greater than about 17%, greater than about 18%, greater than about 19%, greater than about 20%, greater than about 21%, greater than about 22%, greater than about 23%, greater than about 24%, greater than about 25%, greater than about 26%, greater than about 27%, greater than about 28%, greater than about 29%, greater than about 31%, greater than about 32%, greater than about 33%, greater than about 34%, greater than about 35%, greater than about 36%, greater than about 37%, greater than about 38%, greater than about 39%, greater than about 41%, greater than about 42%, greater than about 43%, greater than about 44%, greater than about 45%, greater than about 46%, greater than about 47%, greater than about Δ8%, greater than about 49%, greater than about 51%, greater than about 52%, greater than about 53%, greater than about 54%, greater than about 55%, greater than about 56%, greater than about 57%, greater than about 58%, greater than about 59%, greater than about 61%, greater than about 62%, greater than about 63%, greater than about 64%, greater than about 65%, greater than about 66%, greater than about 67%, greater than about 68%, greater than about 69%, greater than about 71%, greater than about 72%, greater than about 73%, greater than about 74%, greater than about 75%, greater than about 76%, greater than about 77%, greater than about 78%, greater than about 79%, greater than about 81%, greater than about 82%, greater than about 83%, greater than about 84%, greater than about 85%, greater than about 86%, greater than about 87%, greater than about 88%, greater than about 89%, greater than about 91%, greater than about 92%, greater than about 93%, greater than about 94%, greater than about 95%, greater than about 96%, greater than about 97%, greater than about 98%, or greater than about 99% beta-D-glucans by weight of the composition.

In some embodiments, the compositions comprise at least about 5% beta-D-glucans by volume of the composition, for example, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 31%, at least about 32%, at least about 33%, at least about 34%, at least about 35%, at least about 36%, at least about 37%, at least about 38%, at least about 39%, at least about 41%, at least about 42%, at least about 43%, at least about 44%, at least about 45%, at least about 46%, at least about 47%, at least about 48%, at least about 49%, at least about 51%, at least about 52%, at least about 53%, at least about 54%, at least about 55%, at least about 56%, at least about 57%, at least about 58%, at least about 59%, at least about 61%, at least about 62%, at least about 63%, at least about 64%, at least about 65%, at least about 66%, at least about 67%, at least about 68%, at least about 69%, at least about 71%, at least about 72%, at least about 73%, at least about 74%, at least about 75%, at least about 76%, at least about 77%, at least about 78%, at least about 79%, at least about 81%, at least about 82%, at least about 83%, at least about 84%, at least about 85%, at least about 86%, at least about 87%, at least about 88%, at least about 89%, at least about 91%, at least about 92%, at least about 93%, at least about 94%, at least about 95%, at least about 96%, at least about 97%, at least about 98%, or at least about 99% beta-D-glucans by volume of the composition.

In some embodiments, the compositions comprise guarana, or a guarana extract thereof. Guarana is a Brazilian plant native to the Amazon basin. Guarana is loaded with antioxidants and may reduce fatigue, improve focus, promote weight loss, improve learning, treat constipation, and relieve chronic diarrhea, boost heart health, and improve the appearance of skin. In some embodiments, the composition comprises less than about 2% guarana by weight of the composition, for example, less than about 2%, less than about 1.8%, less than about 1.5%, less than about 1.2%, less than about 1%, less than about 0.8%, less than about 0.5%, less than about 0.25% guarana by weight of the composition.

In some embodiments, the compositions comprise valerian root or an extract thereof. Valerian root is an herb native to Europe and parts of Asia known to improve sleep. In some embodiments, the composition comprises less than about 2% valerian root by weight of the composition, for example, less than about 2%, less than about 1.8%, less than about 1.5%, less than about 1.2%, less than about 1%, less than about 0.8%, less than about 0.5%, less than about 0.25% valerian root by weight of the composition.

VII. Methods of Use and Administration

The compositions and formulations of the disclosure can be administered to a subject in need for the improvement of a variety of conditions, including, autoimmune disease, hearth health, lung health, digestive issues, Type 2 Diabetes, inflammation, cancer, seizures, anxiety, stress, and sleep.

In some embodiments, the subject in need is suffering from any one of the following conditions: depression, anxiety, stress, autoimmune disease, hearth health, lung health, digestive issues, Type 2 Diabetes, inflammation, cancer, difficulty sleeping, and difficulty concentrating.

In some embodiments, the subject in need is a human. In some embodiments, the subject is a dog, cat, guinea pig, hamster, rabbit, mouse, rat, tiger, lion, giraffe, elephant, or goat.

In some embodiments, the compositions are administered as tablets, capsules, pills, powders, granules, solutions, suspensions, emulsions, elixir, lotion, cream, gel, ointment, tincture, paste, foam, aerosol, irrigation, spray, suppository, or bandage. The form of the resulting formulation depends upon a number of factors, including the intended mode of administration (e.g. oral administration, enteral administration, parenteral administration, and topical application to the skin, scalp, eyes, and/or nasal, buccal or sublingual mucosa), selected carriers or vehicles, the solubility of the composition in the selected carrier or vehicle. In some embodiments, the composition is administered as a powder encapsulated in a capsule. In some embodiments, the composition is administered as a sublingual drop.

In some embodiments, a subject in need is administered one capsule of any of the compositions described herein. In some embodiments, a subject in need is administered between a 0.1 mL and a 2 mL dose, for example, a 0.1 mL, a 0.2 mL, a 0.3 mL, a 0.4 mL, a 0.5 mL, a 0.6 mL, a 0.7 mL, a 0.8 mL, 0.9 mL, a 1 mL, a 1.1 mL, a 1.2 mL, a 1.3 mL, a 1.4 mL, a 1.5 mL, a 1.6 mL, a 1.7 mL, a 1.8 mL, a 1.9 mL, or a 2 mL dose of a composition described herein, including all values and ranges in between. In some embodiments, a subject in need is administered a 0.5 mL dose of a composition described herein.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby Example 1—Production of Compositions Comprising Mushroom Extract Fraction, Cannabinoid Extract Fraction, Terpene Extract Fraction The following compositions were prepared according to the following method.

Cannabinoid and/or terpene extracts were produced by ethanol extraction of *Cannabis*.

Mushroom Extract Fractions were produced by drying mushrooms, grinding the mushrooms into a fine powder, and boiling the fine powder in water and/or ethanol. The water and/or ethanol was separated from the mushrooms to form a dilute extract. Ethanol was removed from the dilute extract by distillation. The resulting extract was concentrated and spray-dried to form a powder.

Cannabinoid Extracts, Mushroom Extracts, and Terpene Extracts are combined according to the recipes in Table 5.

TABLE 5

| Sample | Mushroom Extract Fraction | Cannabinoid Extract Fraction | Terpene Extract Fraction | Additional Ingredients |
|---|---|---|---|---|
| 1 | 150 mg *Hericium ernaceus* 150 mg *Cordyceps militaris* (1:1 *H. ernaceus*: *C. militaris*) | 15 mg cannabidiol (CBD) 20 mg cannabigerol (CBG) (3:4 CBD:CBG) | alpha pinene, limonene, beta-pinene, alpha phellandrene, terpinolene, nerolidol, and nerol | Guarana |
| 2 | 60 mg *Trametes versicolor*, 60 mg *Ganoderma linggzhi*, 60 mg *Grifola frondosa*, 60 mg *Lentinula edodes*, | 10 mg cannabinol (CBN) 15 mg cannabidiol (CBD) (2:3 CBN:CBD) | alpha pinene, limonene, beta-pinene, alpha phellandrene, terpinolene, nerolidol, and nerol | Valerian root |

TABLE 5-continued

| Sample | Mushroom Extract Fraction | Cannabinoid Extract Fraction | Terpene Extract Fraction | Additional Ingredients |
|---|---|---|---|---|
|  | 60 mg *Inonotus obliquus* (1:1:1:1:1 *T. versicolor*: *G. linggzhi*: *G. frondosa*: *L. edodes*: *I. obliquus*) |  |  |  |
| 3 | 50 mg *Hericium ernaceus*; 50 mg *Cordyceps militaris* (1:1 *H. ernaceus*: *C. militaris*) | 10 mg tetra-hydrocannabinol | alpha pinene, limonene, beta-pinene, alpha phellandrene, terpinolene, nerolidol, and nerol | Guarana |
| 4 | 20 mg *Trametes versicolor*, 20 mg *Ganoderma linggzhi*, 20 mg *Grifola frondosa*, 20 mg *Lentinula edodes*, 20 mg *Inonotus obliquus* (1:1:1:1:1 *T. versicolor*: *G. linggzhi*: *G. frondosa*: *L. edodes*: *I. obliquus*) | 10 mg tetra-hydrocannabinol (THC); 2.5 mg cannabinol (CBN) (4:1 THC:CBN) | alpha pinene, limonene, beta-pinene, alpha phellandrene, terpinolene, nerolidol, and nerol | Valerian root |
| 5 | 250 mg *Hericium ernaceus*, 250 mg *Cordyceps militaris* (1:1 *H. ernaceus*: *C. militaris*) | 450 mg cannabidiol (CBD); 600 mg cannabigerol (CBG) (3:4 CBD:CBG) | alpha pinene, limonene, beta-pinene, alpha phellandrene, terpinolene, nerolidol, and nerol. | Guarana |
| 6 | 100 mg *Trametes versicolor*, 100 mg *Ganoderma linggzhi*, 100 mg *Grifola frondosa*, 100 mg *Lentinula edodes*, 100 mg *Inonotus obliquus* (1:1:1:1:1 *T. versicolor*: *G. linggzhi*: *G. frondosa*: *L. edodes*: *I. obliquus*) | 300 mg cannabinol (CBN) 450 mg cannabidiol (CBD) (2:3 CBN:CBD) | alpha pinene, limonene, beta-pinene, alpha phellandrene, terpinolene, nerolidol, and nerol | Valerian root |
| 7 | 150 mg *Hericium ernaceus*; 150 mg *Cordyceps militaris* (1:1 *H. ernaceus*: *C. militaris*) | 15 mg cannabidiol (CBD); 20 mg cannabigerol (CBG) (3:4 CBD:CBG) | alpha pinene, limonene, beta-pinene, alpha phellandrene, terpinolene, nerolidol, and nerol | Guarana, hypromellose, micro-crystalline cellulose, pure inositol, MCT oil, organic tapioca starch |
| 8 | 60 mg *Trametes versicolor*, 60 mg *Ganoderma linggzhi*, 60 mg *Grifola frondosa*, 60 mg *Lentinula edodes*, 60 mg *Inonotus obliquus* (1:1:1:1:1 *T. versicolor*: *G. linggzhi*: *G. frondosa*: *L. edodes*: *I. obliquus*) | 10 mg cannabinol (CBN) 15 mg cannabidiol (CBD) (2:3 CBN:CBD) | alpha pinene, limonene, beta-pinene, alpha phellandrene, terpinolene, nerolidol, and nerol | Valerian root, hypromellose, micro-crystalline cellulose, pure inositol, MCT oil, organic tapioca starch. |
| 9 | 50 mg *Hericium ernaceus*; 50 mg *Cordyceps militaris* (1:1 *H. ernaceus*: *C. militaris*) | 10 mg tetra-hydrocannabinol | alpha pinene, limonene, beta-pinene, alpha phellandrene, terpinolene, nerolidol, and nerol | Guarana, hypromellose, micro-crystalline cellulose, pure inositol, MCT oil, organic tapioca starch. |
| 10 | 20 mg *Trametes versicolor*, 20 mg *Ganoderma linggzhi*, 20 mg *Grifola frondosa*, 20 mg *Lentinula edodes*, 20 mg *Inonotus obliquus* (1:1:1:1:1 *T. versicolor*: *G. linggzhi*: *G. frondosa*: *L. edodes*: *I. obliquus*) | 10 mg tetra-hydrocannabinol (THC); 2.5 mg cannabinol (CBN) (4:1 THC:CBN) | alpha pinene, limonene, beta-pinene, alpha phellandrene, terpinolene, nerolidol, and nerol | Valerian root, hypromellose, micro-crystalline cellulose, pure inositol, MCT oil, organic tapioca starch. |
| 11 | 250 mg *Hericium ernaceus*; 250 mg *Cordyceps militaris* (1:1 *H.ernaceus*: *C. militaris*) | 450 mg cannabidiol (CBD); 600 mg cannabigerol (CBG) (3:4 CBD:CBG) | alpha pinene, limonene, beta-pinene, alpha phellandrene, terpinolene, nerolidol, and nerol. | Guarana, MCT oil |
| 12 | 100 mg *Trametes versicolor*, 100 mg *Ganoderma linggzhi*, 100 mg *Grifola frondosa*, 100 mg *Lentinula edodes*, 100 mg *Inonotus obliquus* | 300 mg cannabinol (CBN) 450 mg cannabidiol (CBN) (2:3 CBN:CBD) | alpha pinene, limonene, beta-pinene, alpha phellandrene, terpinolene, nerolidol, and nerol | Valerian root, MCT oil |

TABLE 5-continued

| Sample | Mushroom Extract Fraction | Cannabinoid Extract Fraction | Terpene Extract Fraction | Additional Ingredients |
|---|---|---|---|---|
| | obliquus (1:1:1:1:1 T. versicolor: G. linggzhi: G. frondosa: L. edodes: I. obliquus) | | | |

Example 2—Effects of Compositions of Example 1 (Sample 1)

This example evaluates the effects of sample 1, as described in Example 1. Sample 1 comprises 1:1 *H. ernaceus: C. militaris* mushroom extract fraction, 3:4 CBD:CBG cannabinoid fraction, a terpene fraction, and guarana. The sample was mixed with a carrier to facilitate administration to patients in this experiment.

Patients were provided with two units (capsules) of sample 1+carrier to measure its effects across key benefit areas. The experiment was conducted as follows: patients were provided the sample dosage to take home. Patients were pre-screened for any health issues or for medications that might interfere with this experiment. Patients were instructed to take only the provided sample and no other medication or supplements. Patients were permitted to take the sample with or without food any time of day. Patients were, then, asked to complete a questionnaire within 24 hours of the dosing, but not until after the effects of the dosage had worn off. Questionnaire responses are provided in Table 6. Visual representations of the results are also provided in FIGS. 8-12. Notably, sample 1 resulted in high alertness, energy and menthal acuity, while providing high levels of mood enhancement.

TABLE 6

Sample 1 Trial Responses.

| How would you rate your physical health? | How would you rate your mental health? | How would you rate your overall sense of calm? | How would you rate your level of anxiety? | How would you rate your ability to relax? | How would you rate your level of stress? | How would you rate your level of physical comfort? | How would you rate your level of emotional comfort? |
|---|---|---|---|---|---|---|---|
| 5 | 8 | 6 | 2 | 5 | 5 | 8 | 6 |
| 9 | 9 | 7 | 7 | 5 | 5 | 9 | 9 |
| 9 | 10 | 10 | 3 | 10 | 1 | 10 | 10 |
| 7 | 7 | 7 | 6 | 7 | 6 | 8 | 8 |
| 8 | 8 | 7 | 6 | 6 | 6 | 8 | 9 |
| 10 | 10 | 10 | 10 | 5 | 10 | 10 | 10 |
| 7 | 6 | 9 | 8 | 8 | 3 | 8 | 9 |
| 8 | 10 | 7 | 6 | 6 | 8 | 9 | 10 |
| 7 | 7 | 8 | 8 | 7 | 9 | 7 | 7 |
| 8 | 7 | 9 | 2 | 7 | 2 | 10 | 9 |
| 8 | 9 | 9 | 1 | 8 | 3 | 10 | 9 |
| 7 | 8 | 8 | 2 | 8 | 2 | 7 | 8 |
| 8 | 8 | 6 | 3 | 6 | 4 | 7 | 8 |
| 7 | 5 | 5 | 5 | 5 | 5 | 5 | 5 |
| 7 | 6 | 7 | 5 | 6 | 4 | 6 | 5 |
| 9 | 9 | 10 | 1 | 10 | 2 | 9 | 10 |
| 6 | 6 | 9 | 3 | 8 | 5 | 7 | 8 |
| 9 | 8 | 5 | 3 | 9 | 6 | 7 | 7 |
| 8 | 9 | 8 | 3 | 8 | 6 | 7 | 8 |
| 7 | 7 | 7 | 4 | 7 | 4 | 7 | 7 |
| 10 | 10 | 8 | 5 | 4 | 8 | 6 | 8 |
| 9 | 9 | 10 | 2 | 9 | 2 | 8 | 8 |
| 8 | 10 | 9 | 1 | 9 | 2 | 10 | 10 |
| 8 | 9 | 7 | 5 | 6 | 6 | 8 | 7 |
| 6 | 8 | 8 | 6 | 5 | 7 | 7 | 7 |
| 8 | 9 | 7 | 6 | 7 | 7 | 7 | 7 |
| 8 | 7 | 8 | 8 | 6 | 8 | 9 | 8 |
| 8 | 8 | 7 | 2 | 6 | 6 | 7 | 8 |
| 9 | 9 | 9 | 2 | 7 | 6 | 9 | 9 |
| 8 | 8 | 7 | 7 | 7 | 8 | 9 | 8 |
| 7 | 7 | 5 | 6 | 4 | 6 | 5 | 5 |
| 8 | 8 | 5 | 5 | 4 | 4 | 7 | 7 |
| 5 | 7 | 6 | 5 | 4 | 5 | 4 | 8 |
| 8 | 9 | 9 | 2 | 9 | 2 | 9 | 9 |
| 9 | 8 | 6 | 5 | 7 | 7 | 7 | 9 |
| 8 | 7 | 10 | 3 | 10 | 3 | 9 | 10 |
| 7 | 8 | 9 | 3 | 8 | 3 | 8 | 8 |
| 7 | 7 | 6 | 4 | 6 | 7 | 7 | 6 |
| 8 | 9 | 8 | 7 | 5 | 6 | 7 | 7 |
| 8 | 7 | 4 | 9 | 6 | 9 | 6 | 6 |
| 8 | 8 | 7 | 4 | 8 | 6 | 7 | 8 |

TABLE 6-continued

Sample 1 Trial Responses.

| How would you rate the CHANGE in your pain level? (Note: selecting "5" indicates no change) | How would you rate your feeling of alertness? | How would you rate your feeling of mental focus or acuity? | How would you rate your ability to make decisions? | How would you rate your energy level? | How would you rate your ability to function normally? | How would you rate your level of mood enhancement? |
|---|---|---|---|---|---|---|
| 8 | 8 | 7 | 8 | 7 | 8 | 9 |
| 9 | 7 | 8 | 7 | 7 | 5 | 7 |
| 5 | 7 | 5 | 7 | | | |
| 7 | 8 | 7 | 7 | 7 | 8 | 8 |
| 7 | 8 | 8 | 8 | 8 | 10 | 9 |
| 10 | 10 | 10 | 10 | 10 | 10 | 10 |
| 6 | 9 | 10 | 9 | 9 | 9 | 10 |
| 7 | 10 | 9 | 10 | 8 | 10 | 10 |
| 10 | 10 | 10 | 10 | 10 | 10 | 10 |
| 7 | 9 | 9 | 9 | 10 | 10 | 10 |
| 8 | 7 | 8 | 8 | 9 | 10 | 9 |
| 5 | 7 | 6 | 7 | 7 | 8 | 7 |
| 9 | 5 | 10 | 10 | 8 | 10 | 10 |
| 8 | 8 | 8 | 9 | 7 | 9 | 9 |
| 6 | 8 | 8 | 8 | 9 | 9 | 8 |
| 6 | 7 | 8 | 8 | 8 | 8 | 8 |
| 8 | 8 | 8 | 8 | 8 | 8 | 6 |
| 6 | 7 | 7 | 6 | 8 | 10 | 6 |
| 7 | 9 | 9 | 9 | 8 | 9 | 9 |
| 8 | 9 | 6 | 9 | 8 | 10 | 8 |
| 5 | 8 | 8 | 8 | 8 | 9 | 3 |
| 7 | 8 | 9 | 9 | 8 | 9 | 9 |
| 5 | 10 | 10 | 10 | 10 | 10 | 10 |
| 8 | 10 | 10 | 10 | 10 | 10 | 9 |
| 10 | 10 | 10 | 10 | 10 | 10 | 10 |
| 6 | 9 | 10 | 10 | 10 | 10 | 10 |
| 6 | 7 | 7 | 8 | 8 | 9 | 7 |
| 8 | 7 | 7 | 7 | 8 | 8 | 8 |
| 6 | 7 | 7 | 7 | 7 | 9 | 7 |
| 7 | 8 | 9 | 9 | 9 | 9 | 9 |
| 8 | 9 | 9 | 9 | 9 | 9 | 9 |
| 8 | 9 | 9 | 9 | 9 | 9 | 8 |
| 7 | 8 | 8 | 7 | 8 | 8 | 9 |
| 5 | 7 | 7 | 7 | 6 | 7 | 5 |
| 7 | 5 | 6 | 5 | 7 | 6 | 7 |
| 5 | 7 | 8 | 8 | 9 | 5 | 8 |
| 5 | 9 | 10 | 9 | 9 | 9 | 9 |
| 9 | 9 | 10 | 10 | 10 | 10 | 10 |
| 6 | 6 | 9 | 9 | 9 | 10 | 10 |
| 6 | 7 | 7 | 7 | 8 | 8 | 8 |
| 6 | 6 | 6 | 6 | 7 | 7 | 7 |
| 7 | 7 | 7 | 10 | 4 | 8 | 8 |
| 5 | 5 | 6 | 6 | 6 | 6 | 6 |
| 7 | 8 | 8 | 8 | 9 | 9 | 8 |
| 5 | 10 | 10 | 10 | 10 | 10 | 10 |
| 7 | 7 | 8 | 8 | 8 | 5 | 6 |

Example 3—Effects of Compositions of Example 1 (Sample 3)

This example evaluates the effects of sample 3, as described in Example 1. Sample 3 comprises 1:1 *H. ernaceus: C. militaris* mushroom extract fraction, a THC cannabinoid fraction, a terpene fraction, and guarana. The sample was mixed with a carrier to facilitate administration to patients in this experiment.

Patients were provided with two units (capsules) of sample 3+carrier to measure its effects across key benefit areas. The experiment was conducted as follows: patients were pre-screened for any health issues or for medications that might interfere with this experiment. Patients were then provided the sample dosage to take home. Patients were instructed to take only the provided sample and no other medication or supplements. Patients were permitted to take the sample with or without food any time of day. Patients were, then, asked to complete a questionnaire within 24 hours of the dosing, but not until after the effects of the dosage had worn off. Questionnaire responses are provided in Table 7. Visual representations of the results are also provided in FIGS. 13-18. Notably, sample 3 resulted in high alertness, energy and menthal acuity, while providing high levels of mood enhancement.

TABLE 7

Sample 3 Trial Responses.

| How would you rate your physical health? | How would you rate your mental health? | How would you rate your level of intoxication? | How would you rate your overall sense of calm? | How would you rate your level of anxiety? | How would you rate your ability to relax? | How would you rate your level of stress? | How would you rate your level of physical comfort? |
|---|---|---|---|---|---|---|---|
| 9 | 10 | 4 | 10 | 1 | 10 | 1 | 10 |
| 8 | 8 | 7 | 7 | 3 | 7 | 3 | 7 |
| 7 | 7 | 7 | 8 | 5 | 8 | 3 | 7 |
| 9 | 10 | 4 | 8 | 5 | 8 | 7 | 9 |
| 8 | 7 | 5 | 9 | 2 | 8 | 1 | 10 |
| 9 | 9 | 8 | 10 | 3 | 10 | 1 | 10 |
| 7 | 9 | 6 | 8 | 3 | 9 | 4 | 8 |
| 8 | 10 | 6 | 10 | 1 | 10 | 1 | 10 |
| 7 | 7 | 7 | 7 | 6 | 8 | 7 | 7 |
| 9 | 9 | 8 | 9 | 2 | 10 | 3 | 10 |
| 7 | 6 | 7 | 8 | 3 | 7 | 4 | 8 |
| 9 | 9 | 7 | 9 | 4 | 9 | 6 | 8 |
| 7 | 8 | 7 | 9 | 2 | 9 | 2 | 9 |
| 8 | 8 | 5 | 8 | 4 | 7 | 3 | 7 |
| 9 | 9 | 4 | 5 | 3 | 6 | 5 | 9 |
| 7 | 7 | 7 | 4 | 8 | 4 | 5 | 8 |
| 8 | 8 | 7 | 7 | 5 | 7 | 2 | 10 |
| 4 | 7 | 7 | 8 | 6 | 3 | 6 | 4 |
| 8 | 9 | 2 | 9 | 2 | 9 | 2 | 9 |
| 9 | 8 | 5 | 8 | 5 | 9 | 3 | 10 |
| 8 | 7 | 9 | 9 | 3 | 8 | 3 | 8 |
| 9 | 8 | 7 | 10 | 3 | 10 | 3 | 9 |
| 7 | 8 | 7 | 8 | 6 | 6 | 7 | 6 |
| 9 | 9 | 6 | 9 | 3 | 6 | 5 | 10 |
| 7 | 8 | 6 | 7 | 4 | 5 | 7 | 6 |

| How would you rate your level of emotional comfort? | How would you rate the CHANGE in your pain level? (Note: selecting "5" indicates no change) | How would you rate your level of feeling of alertness? | How would you rate your feeling of mental focus or acuity? | How would you rate your ability to make decisions? | How would you rate your energy level? | How would you rate ability to function normally? | How would you rate level of mood enhancement? |
|---|---|---|---|---|---|---|---|
| 10 | 10 | 10 | 10 | 10 | 10 | 10 | 10 |
| 7 | 7 | 5 | 6 | 6 | 6 | 6 | 6 |
| 7 | 9 | 6 | 8 | 8 | 8 | 6 | 9 |
| 9 | 7 | 8 | 9 | 8 | 8 | 8 | 7 |
| 8 | 9 | 9 | 10 | 9 | 9 | 9 | 10 |
| 10 | 8 | 9 | 10 | 10 | 10 | 8 | 10 |
| 9 | 8 | 8 | 7 | 9 | 8 | 9 | 9 |
| 10 | 6 | 10 | 10 | 10 | 10 | 9 | 10 |
| 7 | 8 | 8 | 7 | 8 | 8 | 8 | 8 |
| 10 | 10 | 10 | 10 | 10 | 10 | 10 | 10 |
| 7 | 7 | 8 | 7 | 7 | 7 | 9 | 7 |
| 8 | 10 | 7 | 9 | 7 | 9 | 8 | 10 |
| 9 | 8 | 7 | 8 | 8 | 8 | 8 | 9 |
| 7 | 8 | 9 | 9 | 10 | 5 | 9 | 9 |
| 9 | 5 | 7 | 7 | 7 | 8 | 7 | 7 |
| 6 | 5 | 3 | 4 | 5 | 5 | 4 | 7 |
| 8 | 9 | 10 | 10 | 5 | 10 | 8 | 8 |
| 8 | 9 | 8 | 8 | 6 | 9 | 7 | 10 |
| 9 | 6 | 8 | 8 | 8 | 8 | 8 | 8 |
| 10 | 9 | 10 | 10 | 10 | 10 | 10 | 10 |
| 9 | 7 | 8 | 8 | 7 | 7 | 7 | 10 |
| 9 | 10 | 4 | 4 | 10 | 6 | 9 | 10 |
| 8 | 5 | 9 | 8 | 7 | 9 | 6 | 0 |
| 9 | 5 | 7 | 7 | 7 | 6 | 6 | 10 |
| 7 | 8 | 4 | 3 | 5 | 7 | 4 | 6 |

Example 4—Effects of Compositions of Example 1 (Sample 2)

This example evaluates the effects of sample 2 as described in Example 1. Sample 2 comprises a 1:1:1:1:1 *T. versicolor: G. lingzhi: G. frondosa: L. edodes: I. obliquus* mushroom extract fraction, a 2:3 CBN:CBD cannabinoid fraction, a terpene fraction, and valerian root. The sample was mixed with a carrier to facilitate administration to patients in this experiment.

Patients were provided with two units (capsules) of sample 2+carrier to measure its effects across key benefit areas. Patients were pre-screened for any health issues or for medications that might interfere with this experiment The experiment was conducted as follows: patients were provided the sample dosage to take home. Patients were instructed to take only the provided sample and no other medication or supplements. Patients were permitted to take the sample with or without food in the evening just before going to bed. Patients were, then, asked to complete a questionnaire the morning after the dosing. Questionnaire responses are provided in Table 8. Visual representations of the results are also provided in FIGS. 19-27. Notably, sample 2 resulted in improvements to sleep length, quality, without significant after-effects.

TABLE 8

Sample 2 Trial Responses.

| How would you rate your physical health? | How would you rate your mental health? | How would you rate your ability to FALL asleep? | How would you rate your ability to STAY asleep? | How would you rate your overall sense of calm? | How would you rate your level of anxiety? | How would you rate your ability to relax? | How would you rate your level of stress? | How would you rate your level of physical comfort? |
|---|---|---|---|---|---|---|---|---|
| 8 | 8 | 8 | 6 | 7 | 4 | 8 | 5 | 8 |
| 9 | 10 | 10 | 10 | 10 | 1 | 10 | 1 | 10 |
| 10 | 10 | 10 | 10 | 10 | 10 | 10 | 10 | 10 |
| 8 | 8 | 9 | 9 | 6 | 6 | 6 | 6 | 6 |
| 7 | 7 | 3 | 3 | 9 | 3 | 8 | 3 | 9 |
| 8 | 8 | 3 | 6 | 5 | 5 | 5 | 7 | 1 |
| 9 | 7 | 6 | 7 | 9 | 7 | 9 | 8 | 7 |
| 8 | 7 | 7 | 7 | 10 | 2 | 10 | 2 | 10 |
| 6 | 6 | 8 | 8 | 8 | 1 | 7 | 1 | 6 |
| 7 | 9 | 9 | 3 | 8 | 2 | 9 | 4 | 9 |
| 10 | 10 | 10 | 10 | 10 | 6 | 10 | 8 | 8 |
| 9 | 10 | 10 | 10 | 10 | 1 | 10 | 1 | 10 |
| 9 | 8 | 7 | 7 | 8 | 4 | 8 | 4 | 8 |
| 6 | 7 | 6 | 5 | 8 | 6 | 7 | 7 | 7 |

| How would you rate your level of emotional comfort? | How would you rate the CHANGE in your pain level? | How would you rate your level of sedation? | Did you feel your sleep was restful? | Did you feel groggy the next morning? | Please rate your sense of well-being throughout the next day. | How would you COMPARE falling to sleep using the sample with how you usually fall asleep? | How would you compare the quality of sleep using the sample with your usual sleep? | How would you COMPARE how long you slept using the sample with your usual sleep? |
|---|---|---|---|---|---|---|---|---|
| 8 | 6 | 8 | 9 | 5 | 6 | 8 | 8 | 9 |
| 10 | 10 | 10 | 10 | 1 | 10 | 10 | 10 | 10 |
| 10 | 10 | 10 | 10 | 10 | 10 | 10 | 10 | 10 |
| 6 | 6 | 6 | 8 | 1 | 6 | 9 | 8 | 8 |
| 9 | 8 | 7 | 10 | 6 | 8 | 10 | 10 | 10 |
| 5 | 5 | 10 | 8 | 1 | 10 | 10 | 10 | 10 |
| 9 | 8 | 7 | 9 | 3 | 8 | 9 | 9 | 9 |
| 9 | 9 | 10 | 10 | 1 | 8 | 10 | 10 | 10 |
| 7 | 5 | 6 | 7 | 5 | 6 | 8 | 8 | 8 |
| 9 | 5 | 9 | 9 | 3 | 9 | 7 | 8 | 7 |
| 8 | 7 | 9 | 10 | 1 | 9 | 10 | 10 | 10 |
| 10 | 7 | 9 | 10 | 1 | 9 | 10 | 10 | 10 |
| 9 | 6 | 6 | 8 | 2 | 7 | 7 | 9 | 8 |
| 7 | 7 | 8 | 8 | 6 | 7 | 8 | 8 | 8 |

Example 5—Effects of Compositions of Example 1 (Sample 4)

This example evaluates the effects of sample 4 as described in Example 1. Sample 4 comprises a 1:1:1:1:1 *T. versicolor: G. lingzhi: G. frondosa: L. edodes: I. obliquus* mushroom extract fraction, a 4:1 THC:CBN cannabinoid fraction, a terpene fraction, and valerian root. The sample was mixed with a carrier to facilitate administration to patients in this experiment.

Patients were provided with two units (capsules) of sample 4+carrier to measure its effects across key benefit areas. Patients were pre-screened for any health issues or for medications that might interfere with this experiment The experiment was conducted as follows: patients were provided the sample dosage to take home. Patients were instructed to take only the provided sample and no other medication or supplements. Patients were permitted to take the sample with or without food in the evening just before going to bed. Patients were, then, asked to complete a questionnaire the morning after the dosing. Questionnaire responses are provided in Table 9. Visual representations of the results are also provided in FIGS. 28-37. Notably, sample 4 resulted in improvements to sleep length, quality.

TABLE 9

Sample 4 Trial Responses

| How would you rate your physical health? | How would you rate your mental health? | How would you rate your ability to FALL asleep? | How would you rate your ability to STAY asleep? | How would you rate your level of intoxication? | How would you rate your overall sense of calm? | How would you rate your level of anxiety? | How would you rate your ability to relax? | How would you rate your level of stress? | How would you rate your level of physical comfort? |
|---|---|---|---|---|---|---|---|---|---|
| 8 | 8 | 4 | 3 | 6 | 10 | 10 | 10 | 1 | 10 |
| 8 | 8 | 9 | 8 | 7 | 6 | 3 | 8 | 7 | 8 |
| 7 | 7 | 3 | 3 | 7 | 8 | 3 | 9 | 3 | 8 |
| 7 | 8 | 7 | 7 | 6 | 9 | 2 | 9 | 2 | 9 |
| 8 | 7 | 6 | 6 | 6 | 9 | 2 | 10 | 2 | 9 |
| 7 | 7 | 5 | 4 | 4 | 8 | 3 | 9 | 2 | 8 |
| 8 | 7 | 10 | 8 | 3 | 10 | 2 | 10 | 3 | 9 |
| 7 | 6 | 7 | 6 | 6 | 7 | 3 | 8 | 6 | 7 |
| 7 | 9 | 8 | 3 | 7 | 9 | 2 | 9 | 2 | 9 |
| 9 | 10 | 10 | 10 | 10 | 10 | 1 | 10 | 1 | 10 |
| 7 | 7 | 7 | 7 | 6 | 7 | 7 | 6 | 7 | 7 |
| 8 | 8 | 3 | 4 | 2 | 6 | 3 | 5 | 6 | 6 |
| 9 | 9 | 3 | 3 | 8 | 9 | 4 | 9 | 2 | 10 |
| 8 | 8 | 7 | 3 | 3 | 8 | 1 | 9 | 1 | 9 |
| 9 | 9 | 9 | 8 | 7 | 8 | 2 | 8 | 2 | 9 |
| 8 | 8 | 9 | 8 | 1 | 5 | 7 | 7 | 7 | 10 |
| 7 | 7 | 7 | 7 | 8 | 2 | 4 | 8 | 3 | 7 |
| 8 | 8 | 1 | 7 | 8 | 10 | 3 | 9 | 3 | 1 |
| 5 | 7 | 4 | 6 | 3 | 8 | 3 | 4 | 7 | 4 |
| 8 | 9 | 9 | 6 | 6 | 9 | 1 | 10 | 1 | 9 |
| 9 | 8 | 8 | 8 | 5 | 8 | 1 | 9 | 1 | 9 |
| 9 | 8 | 8 | 5 | 8 | 8 | 5 | 8 | 4 | 4 |
| 7 | 8 | 9 | 10 | 7 | 8 | 6 | 9 | 7 | 6 |
| 9 | 9 | 9 | 8 | 3 | 9 | 1 | 10 | 2 | 8 |

| How would you rate your level of emotional comfort? | How would you rate the CHANGE in your pain level? (Note: selecting "5" indicates no change) | How would you rate your level of sedation? | Did you feel your sleep was restful? | Did you feel groggy the next morning? | Please rate your sense of well-being throughout the next day. | How would you COMPARE falling to sleep using the sample with how you usually fall asleep? | How would you compare the quality of sleep using the sample with your usual sleep? | How would you COMPARE how long you slept using the sample with your usual sleep? |
|---|---|---|---|---|---|---|---|---|
| 10 | 10 | 1 | 5 | 1 | 8 | 10 | 10 | 10 |
| 8 | 6 | 6 | 7 | 6 | 6 | 7 | 8 | 8 |
| 8 | 9 | 7 | 10 | 7 | 10 | 5 | 10 | 10 |
| 9 | 9 | 8 | 10 | 2 | 9 | 6 | 9 | 9 |
| 8 | 9 | 5 | 10 | 1 | 9 | 5 | 10 | 10 |
| 7 | 9 | 1 | 9 | 1 | 8 | 9 | 8 | 8 |
| 10 | 8 | 3 | 10 | 1 | 8 | 7 | 10 | 7 |
| 6 | 6 | 4 | 7 | 3 | 6 | 8 | 8 | 6 |
| 8 | 6 | 8 | 6 | 3 | 8 | 8 | 8 | 7 |
| 10 | 8 | 6 | 10 | 1 | 9 | 10 | 10 | 10 |
| 7 | 7 | 7 | 7 | 6 | 7 | 8 | 8 | 8 |
| 6 | 5 | 5 | 2 | 2 | 5 | 3 | 3 | 1 |
| 10 | 10 | 9 | 7 | 4 | 10 | 10 | 10 | 9 |
| 9 | 9 | 6 | 10 | 1 | 9 | 9 | 9 | 9 |
| 9 | 7 | 9 | 9 | 4 | 7 | 9 | 8 | 8 |
| 9 | 5 | 2 | 5 | 6 | 5 | 7 | 8 | 5 |
| 8 | 5 | 8 | 9 | 7 | 7 | 9 | 7 | 6 |
| 9 | 8 | 10 | 10 | 1 | 10 | 5 | 10 | 5 |
| 8 | 10 | 8 | 10 | 1 | 8 | 8 | 10 | 5 |
| 9 | 7 | 8 | 9 | 1 | 7 | 8 | 8 | 8 |
| 9 | 8 | 6 | 9 | 1 | 9 | 10 | 10 | 10 |
| 5 | 10 | 5 | 4 | 10 | 5 | 5 | 10 | 9 |
| 9 | 6 | 8 | 9 | 4 | 8 | 7 | 7 | 8 |
| 9 | 9 | 5 | 9 | 3 | 9 | 9 | 8 | 6 |

Example 6—Effects of Compositions of Example 1

Formulations comprising the compositions described in Example 1 (e.g., a capsule or a sublingual drop) will be provided to consumers together with a questionnaire. The questionnaire will request feedback regarding the therapeutic effects of each sample. An example of the type of questionnaire that will be used is provided in Table B.

Consumers will also receive control formulations comprising no Mushroom Extract Fraction and/or no Cannabinoid Extract Fraction and/or no Terpene Extract Fraction with one or more other ingredients removed or altered. These results are thus expected to identify the effects specific to the compositions described herein.

TABLE 10

Example questionnaire.
Self-Reported Effects of Composition

| Trial Volunteer: | Composition Tested: |
|---|---|
| 1 = Extremely Terrible-10 = Extremely Great | |
| How would you rate the mind high? | 1 2 3 4 5 6 7 8 9 10 |
| How would you rate your physical health? | 1 2 3 4 5 6 7 8 9 10 |
| How would you rate your mental health? | 1 2 3 4 5 6 7 8 9 10 |
| 1 = Extremely Low-10 = Extremely High | |
| How would you rate your level of intoxication? | 1 2 3 4 5 6 7 8 9 10 |
| How would you rate your feeling of calmness? | 1 2 3 4 5 6 7 8 9 10 |
| How would you rate your feeling of alertness? | 1 2 3 4 5 6 7 8 9 10 |
| How would you rate your level of anxiety? | 1 2 3 4 5 6 7 8 9 10 |
| How would you rate your ability to focus? | 1 2 3 4 5 6 7 8 9 10 |
| How would you rate your level of stress? | 1 2 3 4 5 6 7 8 9 10 |
| How would you rate your level of mood enhancement? | 1 2 3 4 5 6 7 8 9 10 |
| How would you rate your energy level? | 1 2 3 4 5 6 7 8 9 10 |
| How would you rate your level of hunger? | 1 2 3 4 5 6 7 8 9 10 |
| How would you rate your level of thirst? | 1 2 3 4 5 6 7 8 9 10 |
| How would you rate your level of physical comfort (pain)? | 1 2 3 4 5 6 7 8 9 10 |
| How would you rate your level of emotional comfort? | 1 2 3 4 5 6 7 8 9 10 |
| How would you rate your ability to function normally? | 1 2 3 4 5 6 7 8 9 10 |
| Over the past six months how often have you experienced a viral infection? | _____days |
| Over the past six months how often have you experienced a bacterial infection? | _____days |
| How would you rate your level of sedation? | 1 2 3 4 5 6 7 8 9 10 |
| 1 = Extremely Brief-10 = Extremely Long | |
| How would you rate the length of your effects? | 1 2 3 4 5 6 7 8 9 10 |
| 1 = Extremely Low-10 = Extremely High | |
| Rate the perceived level of positive effects that you attribute to this sample. | 1 2 3 4 5 6 7 8 9 10 |
| Rate the perceived level of negative effects that you attribute to this sample. | 1 2 3 4 5 6 7 8 9 10 |
| 1 = Extremely Mild-10 = Extremely Severe, Write N/A if this question does not apply. | |
| Rate the Severity of your Obsessive Compulsive Disorder (OCD) | 1 2 3 4 5 6 7 8 9 10 |
| Rate the severity of suicidal thoughts. | 1 2 3 4 5 6 7 8 9 10 |
| Rate the severity of your addiction to alcohol and/or drugs. | 1 2 3 4 5 6 7 8 9 10 |
| Comments: | |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

Additional Embodiments of the Invention

The following embodiments are also envisioned by the present disclosure:

1. A composition comprising:
 a) a Cannabinoid Fraction;
 b) a Mushroom Extract Fraction; and
 c) a Terpene Fraction.

2. The composition of embodiment 1, wherein the Cannabinoid Fraction comprises two cannabinoids selected from the group consisting of: cannabidiol (CBD), cannabigerol (CBG), cannabinol (CBN), and tetrahydrocannabinol (THC).

3. The composition of any one of embodiments 1 and 2, wherein the Mushroom Extract Fraction comprises at least two mushroom extracts selected from the group consisting of; *Hericium* ernaceus, *Cordyceps militaris, Trametes versicolor, Ganoderma lingzhi, Grifola frondosa, Lentinula edodes*, and *Inonotus obliquus*.

4. The composition of any one of embodiments 1-3, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

4.1 The composition of any one of embodiments 1-3, wherein the Terpene Fraction comprises at least two terpenes selected from the group consisting of: alpha pinene, limonene, beta-pinene, alpha phellandrene, terpinolene, nerolidol, and nerol.

5. The composition of any one of embodiments 1-3, wherein the Terpene Fraction comprises alpha pinene, limonene, beta-pinene, alpha phellandrene, terpinolene, nerolidol, and nerol.

6. The composition of any one of embodiments 1-5, said composition comprising a triterpene selected from the group consisting of: ergosterol peroxide; cerevisterol; 3β.5α,9α,-trihydroxy-ergosta-7,22-dien-6-one; inoterpene A; astradoric acid C; betulin; oleanolic acid; ursolic acid; hemicer-amide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

7. The composition of any one of embodiments 1-6, said composition comprising Beta-D-glucans.

8. The composition of any one of embodiments 1-7, said composition comprising valerian root.

8.1 The composition of any one of embodiments 1-7, said composition comprising caffeine.

8.2 The composition of any one of embodiments 1-7, said composition comprising guarana.

9. The composition of any one of embodiments 1-8, said composition comprising starch.

10. The composition of any one of embodiments 1-9, said composition comprising hypromellose, microcrystalline cellulose, inositol, and MCT oil.

11. A composition comprising:
 a) a Cannabinoid Fraction comprising
  i) cannabidiol (CBD);
  ii) cannabigerol (CBG); and b) a Mushroom Extract Fraction comprising
   i) *Hericium ernaceus;*
   ii) *Cordyceps militaris;* and
c) a Terpene Fraction comprising one or more terpenes.

12. The composition of embodiment 11, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

12.1 The composition of embodiment 11, wherein the Terpene Fraction comprises at least two terpenes selected from the group consisting of: alpha pinene, limonene, beta-pinene, alpha phellandrene, terpinolene, nerolidol, and nerol.

13. The composition of embodiment 11, wherein the Terpene Fraction comprises alpha pinene, limonene, beta-pinene, alpha phellandrene, terpinolene, nerolidol, and nerol.

14. The composition of any one of embodiments 11-13, wherein the Cannabinoid Fraction comprises a CBD:CBG ratio of between 2:1 and 1:2 by weight.

15. The composition of any one of embodiments 11-13, wherein the Cannabinoid Fraction comprises a CBD:CBG ratio of about 3:4 by weight.

16. The composition of any one of embodiments 11-13, wherein the Cannabinoid Fraction comprises between 30-50% CBD and 40-70% CBG by weight of the Cannabinoid Fraction.

17. The composition of any one of embodiments 11-16, wherein the Mushroom Extract Fraction comprises a *Hericium ernaceus:Cordyceps militaris* ratio between 2:1 and 1:2 by weight.

18. The composition of any one of embodiments 11-16, wherein the Mushroom Extract Fraction comprises a *Hericium ernaceus:Cordyceps militaris* ratio of about 1:1 by weight.

19. The composition of any one of embodiments 11-16, wherein the Mushroom Extract Fraction comprises between 40-60% *Hericium ernaceus* and 40-60% *Cordyceps militaris* by weight of the Mushroom Extract Fraction.

20. The composition of any one of embodiments 11-19, comprising a Cannabinoid Fraction to Mushroom Extract Fraction ratio between 1:8 to 1:11 by weight.

21. The composition of any one of embodiments 11-19, comprising a Cannabinoid Fraction to Mushroom Extract Fraction ratio of about 7:60 by weight.

22. The composition of any one of embodiments 11-21, comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

23. The composition of any one of embodiments 11-22, said composition comprising Beta-D-glucans.

24. The composition of any one of embodiments 11-23, said composition comprising valerian root.

24.1 The composition of any one of embodiments 11-23, said composition comprising caffeine.

24.2 The composition of any one of embodiments 11-23, said composition comprising guarana.

25. The composition of any one of embodiments 11-24, said composition comprising starch.

26. The composition of any one of embodiments 11-25, said composition comprising hypromellose, microcrystalline cellulose, inositol, and MCT oil.

27. A composition comprising:
a) a Cannabinoid Fraction comprising
   i) about 15 mg cannabidiol (CBD);
   ii) about 20 mg cannabigerol (CBG); and
b) a Mushroom Extract Fraction comprising
   i) about 150 mg *Hericium ernaceus;*
   ii) about 150 mg *Cordyceps militaris;* and
c) a Terpene Fraction comprising alpha pinene, limonene, beta-pinene, alpha phellandrene, terpinolene, nerolidol, and nerol.

28. A composition comprising:
a) a Cannabinoid Fraction comprising
   i) cannabinol (CBN);
   ii) cannabidiol (CBD); and
b) a Mushroom Extract Fraction comprising
   i) *Trametes versicolor,*
   ii) *Ganoderma lingzhi,*
   iii) *Grifola frondosa,*
   iv) *Lentinula edodes,*
   v) *Inonotus obliquus;* and
c) a Terpene Fraction comprising one or more terpenes.

29. The composition of embodiment 28, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

29.1 The composition of embodiment 28, wherein the Terpene Fraction comprises at least two terpenes selected from the group consisting of: alpha pinene, limonene, beta-pinene, alpha phellandrene, terpinolene, nerolidol, and nerol.

30. The composition of embodiment 28, wherein the Terpene Fraction comprises alpha pinene, limonene, beta-pinene, alpha phellandrene, terpinolene, nerolidol, and nerol.

31. The composition of any one of embodiments 28-30, wherein the Cannabinoid Fraction comprises a CBN:CBD ratio between 2:1 and 1:2 by weight.

32. The composition of any one of embodiments 28-30, wherein the Cannabinoid Fraction comprises a CBN:CBD ratio of about 2:3 by weight.

33. The composition of any one of embodiments 28-30, wherein the Cannabinoid Fraction comprises between 30-50% CBN and 50-70% CBD by weight of the Cannabinoid Fraction.

34. The composition of any one of embodiments 28-33, wherein the Mushroom Extract Fraction comprises about equal parts of *Trametes versicolor, Ganoderma lingzhi, Grifola frondosa, Lentinula edodes,* and *Inonotus obliquus* by weight.

35. The composition of any one of embodiments 28-33, wherein the Mushroom Extract Fraction comprises between 10-30% *Trametes versicolor,* 10-30% *Ganoderma lingzhi,* 10-30% *Grifola frondosa,* 10-30% *Lentinula edodes,* and 10-30% *Inonotus obliquus* by weight of the Mushroom Extract Fraction.

36. The composition of any one of embodiments 28-35, comprising a Cannabinoid Fraction to Mushroom Extract Fraction ratio between 1:8 to 1:10 by weight.

37. The composition of any one of embodiments 28-35, comprising a Cannabinoid Fraction to Mushroom Extract Fraction ratio of about 7:60 by weight.

38. The composition of any one of embodiments 28-37, comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6, 23-tetrahydroxy-urs-12-en-28-oic acid); novel (2,3,23-trihydroxy-urs-12-en-28-oic acid); ganoderic acid A; and Lanostanes.

39. The composition of any one of embodiments 28-38, said composition comprising Beta-D-glucans.

40. The composition of any one of embodiments 28-39, said composition comprising valerian root.

40.1 The composition of any one of embodiments 28-39, said composition comprising caffeine.

40.2 The composition of any one of embodiments 28-39, said composition comprising guarana.

41. The composition of any one of embodiments 28-40, said composition comprising starch.

42. The composition of any one of embodiments 28-41, said composition comprising hypromellose, microcrystalline cellulose, inositol, and MCT oil.

43. A composition comprising:
  a) a Cannabinoid Fraction comprising
    i) about 10 mg cannabinol (CBN);
    ii) about 15 mg cannabidiol (CBD); and
  b) a Mushroom Extract Fraction comprising
    i) about 60 mg *Trametes versicolor,*
    ii) about 60 mg *Ganoderma lingzhi,*
    iii) about 60 mg *Grifola frondosa,*
    iv) about 60 mg *Lentinula edodes,*
    v) about 60 mg *Inonotus obliquus*; and
  c) a Terpene Fraction comprising alpha pinene, limonene, beta-pinene, alpha phellandrene, terpinolene, nerolidol, and nerol.

44. A composition comprising:
  a) a Cannabinoid Fraction comprising tetrahydrocannabinol (THC);
  b) a Mushroom Extract Fraction comprising
    i) *Hericium ernaceus;*
    ii) *Cordyceps militaris*; and
  c) a Terpene Fraction comprising one or more terpenes.

45. The composition of embodiment 44, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

45.1 The composition of embodiment 44, wherein the Terpene Fraction comprises at least two terpenes selected from the group consisting of: alpha pinene, limonene, beta-pinene, alpha phellandrene, terpinolene, nerolidol, and nerol.

46. The composition of embodiment 44, wherein the Terpene Fraction comprises alpha pinene, limonene, beta-pinene, alpha phellandrene, terpinolene, nerolidol, and nerol.

47. The composition of any one of embodiments 44-46, wherein the Mushroom Extract Fraction comprises a *Hericium ernaceus:Cordyceps militaris* ratio between 2:1 and 1:2 by weight.

48. The composition of any one of embodiments 44-46, wherein the Mushroom Extract Fraction comprises a *Hericium ernaceus:Cordyceps militaris* ratio of about 1:1 by weight.

49. The composition of any one of embodiments 44-46, wherein the Mushroom Extract Fraction comprises between 40-60% *Hericium ernaceus* and 40-60% *Cordyceps militaris* by weight of the Mushroom Extract Fraction.

50. The composition of any one of embodiments 44-49, comprising a Cannabinoid Fraction to Mushroom Extract Fraction ratio between 1:8 to 1:11 by weight.

51. The composition of any one of embodiments 44-49, comprising a Cannabinoid Fraction to Mushroom Extract Fraction ratio of about 1:10 by weight.

52. The composition of any one of embodiments 44-51, comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6, 23-tetrahydroxy-urs-12-en-28-oic acid); novel (2,3,23-trihydroxy-urs-12-en-28-oic acid); ganoderic acid A; and Lanostanes.

53. The composition of any one of embodiments 44-52, said composition comprising Beta-D-glucans.

54. The composition of any one of embodiments 44-53, said composition comprising valerian root.

54.1 The composition of any one of embodiments 11-23, said composition comprising caffeine.

54.2 The composition of any one of embodiments 11-23, said composition comprising guarana.

55. The composition of any one of embodiments 44-54, said composition comprising starch.

56. The composition of any one of embodiments 44-55, said composition comprising hypromellose, microcrystalline cellulose, inositol, and MCT oil.

57. A composition comprising:
  a) a Cannabinoid Fraction comprising about 10 mg tetrahydrocannabinol (THC);
  b) a Mushroom Extract Fraction comprising
    i) about 50 mg *Hericium ernaceus;*
    ii) about 50 mg *Cordyceps militaris*; and
  c) a Terpene Fraction comprising alpha pinene, limonene, beta-pinene, alpha phellandrene, terpinolene, nerolidol, and nerol.

58. A composition comprising:
  a) a Cannabinoid Fraction comprising
    i) tetrahydrocannabinol (THC);
    ii) cannabinol (CBN); and
  b) a Mushroom Extract Fraction comprising
    i) *Trametes versicolor,*
    ii) *Ganoderma lingzhi,*
    iii) *Grifola frondosa,*
    iv) *Lentinula edodes,*
    v) *Inonotus obliquus*; and
  c) a Terpene Fraction comprising one or more terpenes.

59. The composition of embodiment 58, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

59.1 The composition of embodiment 58, wherein the Terpene Fraction comprises at least two terpenes selected from the group consisting of: alpha pinene, limonene, beta-pinene, alpha phellandrene, terpinolene, nerolidol, and nerol.

60. The composition of embodiment 58, wherein the Terpene Fraction comprises alpha pinene, limonene, beta-pinene, alpha phellandrene, terpinolene, nerolidol, nerol, myrcene, and beta caryophyllene.

61. The composition of any one of embodiments 58-60, wherein the Cannabinoid Fraction comprises a THC:CBN ratio between 6:1 and 2:1 by weight.

62. The composition of any one of embodiments 58-60, wherein the Cannabinoid Fraction comprises a THC:CBN ratio of about 4:1 by weight.

63. The composition of any one of embodiments 58-60, wherein the Cannabinoid Fraction comprises between 70-90% THC and 10-30% CBN by weight of the Cannabinoid Fraction.

64. The composition of any one of embodiments 58-63, wherein the Mushroom Extract Fraction comprises about equal parts of *Trametes versicolor, Ganoderma lingzhi, Grifola frondosa, Lentinula edodes*, and *Inonotus obliquus* by weight.

65. The composition of any one of embodiments 58-63, wherein the Mushroom Extract Fraction comprises between 10-30% *Trametes versicolor,* 10-30% *Ganoderma lingzhi,* 10-30% *Grifola frondosa,* 10-30% *Lentinula edodes,* and 10-30% *Inonotus obliquus* by weight of the Mushroom Extract Fraction.

66. The composition of any one of embodiments 58-65, comprising a Cannabinoid Fraction to Mushroom Extract Fraction ratio between 1:8 to 1:10 by weight.

67. The composition of any one of embodiments 58-65, comprising a Cannabinoid Fraction to Mushroom Extract Fraction ratio of about 1:8 by weight.

68. The composition of any one of embodiments 58-67, comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

69. The composition of any one of embodiments 58-68, said composition comprising Beta-D-glucans.

70. The composition of any one of embodiments 58-69, said composition comprising valerian root.

70.1 The composition of any one of embodiments 58-69, said composition comprising caffeine.

70.2 The composition of any one of embodiments 58-69, said composition comprising guarana.

71. The composition of any one of embodiments 58-70, said composition comprising starch.

72. The composition of any one of embodiments 58-70, said composition comprising hypromellose, microcrystalline cellulose, inositol, and MCT oil.

73. A composition comprising:
a) a Cannabinoid Fraction comprising
i) about 10 mg tetrahydrocannabinol (THC);
ii) about 2.5 mg cannabinol (CBN); and
b) a Mushroom Extract Fraction comprising
i) about 20 mg *Trametes versicolor,*
ii) about 20 mg *Ganoderma lingzhi,*
iii) about 20 mg *Grifola frondosa,*
iv) about 20 mg *Lentinula edodes,*
v) about 20 mg *Inonotus obliquus*; and
c) a Terpene Fraction comprising alpha pinene, limonene, beta-pinene, alpha phellandrene, terpinolene, nerolidol, and nerol.

74. A composition comprising:
a) a Cannabinoid Fraction comprising
i) cannabidiol (CBD);
ii) cannabigerol (CBG); and
b) a Mushroom Extract Fraction comprising
i) *Hericium ernaceus;*
ii) *Cordyceps militaris*; and
c) a Terpene Fraction.

75. The composition of embodiment 74, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

76. The composition of embodiment 74, wherein the Terpene Fraction comprises alpha pinene, limonene, beta-pinene, alpha phellandrene, terpinolene, nerolidol, and nerol.

77. The composition of any one of embodiments 74-76, wherein the Cannabinoid Fraction comprises a CBD:CBG ratio between 2:1 and 1:2 by weight.

78. The composition of any one of embodiments 74-76, wherein the Cannabinoid Fraction comprises a CBD:CBG ratio of about 3:4 by weight.

79. The composition of any one of embodiments 74-76, wherein the Cannabinoid Fraction comprises between 30-50% CBD and 40-70% CBG by weight of the Cannabinoid Fraction.

80. The composition of any one of embodiments 74-79, wherein the Mushroom Extract Fraction comprises a *Hericium ernaceus:Cordyceps militaris* ratio between 2:1 and 1:2 by weight.

81. The composition of any one of embodiments 74-79, wherein the Mushroom Extract Fraction comprises a *Hericium ernaceus:Cordyceps militaris* ratio of about 1:1 by weight.

82. The composition of any one of embodiments 74-79, wherein the Mushroom Extract Fraction comprises between 40-60% *Hericium ernaceus* and 40-60% *Cordyceps militaris* by weight of the Mushroom Extract Fraction.

83. The composition of any one of embodiments 74-82, comprising a Cannabinoid Fraction to Mushroom Extract Fraction ratio between 3:1 to 1:1 by weight.

84. The composition of any one of embodiments 74-82, comprising a Cannabinoid Fraction to Mushroom Extract Fraction ratio of about 21:10 by weight.

85. The composition of any one of embodiments 74-84, comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6,23-tetrahydroxy-urs-12-en-28-oic acid); novel (2,3,23-trihydroxy-urs-12-en-28-oic acid); ganoderic acid A; and Lanostanes.

86. The composition of any one of embodiments 74-85, said composition comprising Beta-D-glucans.

87. The composition of any one of embodiments 74-86, said composition comprising valerian root.

87.1 The composition of any one of embodiments 74-86, said composition comprising caffeine.

87.2 The composition of any one of embodiments 74-86, said composition comprising guarana.

88. The composition of any one of embodiments 74-87, said composition comprising starch.

89. The composition of any one of embodiments 74-88, said composition comprising hypromellose, microcrystalline cellulose, inositol, and MCT oil.

90. A composition comprising:
a) a Cannabinoid Fraction comprising
i) about 450 mg cannabidiol (CBD);
ii) about 600 mg cannabigerol (CBG); and
b) a Mushroom Extract Fraction comprising
i) about 250 mg *Hericium ernaceus*;
ii) about 250 mg *Cordyceps militaris*; and
c) a Terpene Fraction comprising alpha pinene, limonene, beta-pinene, alpha phellandrene, terpinolene, nerolidol, and nerol.

91. A composition comprising:
a) a Cannabinoid Fraction comprising
i) cannabinol (CBN);
ii) cannabidiol (CBD); and
b) a Mushroom Extract Fraction comprising
i) *Trametes versicolor*,
ii) *Ganoderma lingzhi*,
iii) *Grifola frondosa*,
iv) *Lentinula edodes*,
v) *Inonotus obliquus*; and
c) a Terpene Fraction.

92. The composition of embodiment 91, wherein the Terpene Fraction comprises at least two terpenes selected from the group consisting of: alpha pinene, limonene, beta-pinene, alpha phellandrene, terpinolene, nerolidol, nerol, myrcene, and beta caryophyllene.

93. The composition of embodiment 91, wherein the Terpene Fraction comprises alpha pinene, limonene, beta-pinene, alpha phellandrene, terpinolene, nerolidol, and nerol.

94. The composition of any one of embodiments 91-93, wherein the Cannabinoid Fraction comprises a CBN:CBD ratio between 2:1 and 1:2 by weight.

95. The composition of any one of embodiments 91-93, wherein the Cannabinoid Fraction comprises a CBN:CBD ratio of about 2:3 by weight.

96. The composition of any one of embodiments 91-93, wherein the Cannabinoid Fraction comprises between 30-40% CBN and 60-70% CBD by weight of the Cannabinoid Fraction.

97. The composition of any one of embodiments 91-96, wherein the Mushroom Extract Fraction comprises about equal parts of *Trametes versicolor, Ganoderma lingzhi, Grifola frondosa, Lentinula edodes*, and *Inonotus obliquus* by weight.

98. The composition of any one of embodiments 91-96, wherein the Mushroom Extract Fraction comprises between 10-30% *Trametes versicolor*, 10-30% *Ganoderma lingzhi*, 10-30% *Grifola frondosa*, 10-30% *Lentinula edodes*, and 10-30% *Inonotus obliquus* by weight of the Mushroom Extract Fraction.

99. The composition of any one of embodiments 91-98, comprising a Cannabinoid Fraction to Mushroom Extract Fraction ratio between 2:1 to 1:2 by weight.

100. The composition of any one of embodiments 91-98, comprising a Cannabinoid Fraction to Mushroom Extract Fraction ratio of about 3:2 by weight.

101. The composition of any one of embodiments 91-100, comprising a triterpene selected from the group consisting of ergosterol peroxide; cerevisterol; 3β.5α,9α,-trihydroxy-ergosta-7,22-dien-6-one; inoterpene A; astradoric acid C; betulin; oleanolic acid; ursolic acid; hemiceramide; 3,4-dihydro-5-methoxy-2-methyl-2-(4'-methyl-2'-oxo-3'-pentenyl)-9(7H)-oxo-2H-furo[3,4-h]beozopyran; lupeol (2,3,6, 23-tetrahydroxy-urs-12-en-28-oic acid); novel (2,3,23-trihydroxy-urs-12-en-28-oic acid); ganoderic acid A; and Lanostanes.

102. The composition of any one of embodiments 91-101, said composition comprising Beta-D-glucans.

103. The composition of any one of embodiments 91-102, said composition comprising valerian root.

103.1 The composition of any one of embodiments 91-102, said composition comprising caffeine.

103.2 The composition of any one of embodiments 91-102, said composition comprising guarana.

104. The composition of any one of embodiments 91-103, said composition comprising starch.

105. The composition of any one of embodiments 91-104, said composition comprising hypromellose, microcrystalline cellulose, inositol, and MCT oil.

106. A composition comprising:
a) a Cannabinoid Fraction comprising
i) about 300 mg cannabinol (CBN);
ii) about 450 mg cannabidiol (CBD); and
b) a Mushroom Extract Fraction comprising
i) about 100 mg *Trametes versicolor*,
ii) about 100 mg *Ganoderma lingzhi*,
iii) about 100 mg *Grifola frondosa*,
iv) about 100 mg *Lentinula edodes*,
v) about 100 mg *Inonotus obliquus*; and
c) a Terpene Fraction comprising alpha pinene, limonene, beta-pinene, alpha phellandrene, terpinolene, nerolidol, and nerol.

What is claimed is:
1. A capsule comprising:
i. a Cannabinoid Fraction comprising purified cannabidiol (CBD) and purified cannabinol (CBN);
ii. a Mushroom Extract Fraction comprising *Trametes versicolor, Ganoderma* lingzhi, Grifola *frondosa, Lentinula edodes*, and Inonotus obliquus; and
iii. a Terpene Fraction.

2. The capsule of claim 1, wherein the Terpene Fraction comprises:
at least two terpenes selected from the group consisting of: alpha pinene, limonene, beta-pinene, alpha phellandrene, terpinolene, nerolidol, and nerol.

3. The capsule of claim 1, wherein the Terpene Fraction comprises: alpha pinene, limonene, beta-pinene, alpha phellandrene, terpinolene, nerolidol, and nerol.

4. The capsule of claim 1, further comprising valerian root.

5. The capsule of claim 1, comprising from about 10 mg to about 20 mg of CBD.

6. The capsule of claim 1, comprising about 15 mg of CBD.

7. The capsule of claim 1, comprising from about 5 mg to about 15 mg of CBN.

8. The capsule of claim 1, comprising about 10 mg of CBN.

9. The capsule of claim 1, wherein the CBN and CBD are present in a ratio of about 2:3 by weight, respectively.

10. The capsule of claim 1, comprising from about 50 to about 70 mg of each of *Trametes versicolor, Ganoderma* lingzhi, Grifola *frondosa, Lentinula edodes*, and Inonotus obliquus.

11. The capsule of claim 1, comprising about 60 mg of *Trametes versicolor*.

12. The capsule of claim 1, comprising about 60 mg of *Ganoderma* lingzhi.

13. The capsule of claim 1, comprising about 60 mg of Grifola *frondosa*.

14. The capsule of claim 1, comprising about 60 mg of *Lentinula edodes*.

15. The capsule of claim 1, comprising about 60 mg of Inonotus obliquus.

16. The capsule of claim 1, wherein the *Trametes versicolor, Ganoderma* lingzhi, Grifola *frondosa, Lentinula edodes*, and Inonotus obliquus are present in a ratio of about 1:1 by weight, respectively.

17. The capsule of claim 1, wherein the Terpene Fraction comprises alpha pinene, limonene, beta-pinene, alpha phellandrene, terpinolene, nerolidol, and nerol; wherein CBN and CBD are present in a ratio of about 2:3 by weight, respectively and wherein *Trametes versicolor, Ganoderma* lingzhi,, Grifola *frondosa, Lentinula edodes*, and Inonotus obliquus are present in a ratio of about 1:1:1:1:1, by weight, respectively.

18. The capsule of claim 1, further comprising hypromellose, microcrystalline cellulose, inositol, medium chain triglyceride (MCT) oil, and tapioca starch.

19. The capsule of claim 17, further comprising hypromellose, microcrystalline cellulose, inositol, medium chain triglyceride (MCT) oil, and tapioca starch.

\* \* \* \* \*

UNITED STATES PATENT AND TRADEMARK OFFICE
CERTIFICATE OF CORRECTION

PATENT NO. : 12,290,542 B2
APPLICATION NO. : 18/597236
DATED : May 6, 2025
INVENTOR(S) : Parker Berling et al.

It is certified that error appears in the above-identified patent and that said Letters Patent is hereby corrected as shown below:

In the Claims

At Column 87, Line 12:
"lingzhi,, Grifola *frondosa*, *Lentinula edodes*, and Inonotus"
Should read:
-- lingzhi, Grifola *frondosa*, *Lentinula edodes*, and Inonotus --

Signed and Sealed this
Seventeenth Day of June, 2025

Coke Morgan Stewart
*Acting Director of the United States Patent and Trademark Office*